(12) United States Patent
Kloek et al.

(10) Patent No.: US 6,875,595 B2
(45) Date of Patent: Apr. 5, 2005

(54) NEMATODE FATTY ACID DESATURASE-LIKE SEQUENCES

(75) Inventors: Andrew P. Kloek, St. Louis, MO (US); Deryck J. Williams, St. Louis, MO (US); Merry B. McLaird, Brentwood, MO (US); John D. Bradley, St. Louis, MO (US); Jennifer A. Davila-Aponte, St. Louis, MO (US); Siqun Xu, Ballwin, MO (US); Anita M. Frevert, St. Louis, MO (US)

(73) Assignee: Divergence, Inc., St. Louis, MO (US)

( * ) Notice: Subject to any disclaimer, the term of this patent is extended or adjusted under 35 U.S.C. 154(b) by 23 days.

(21) Appl. No.: 10/243,468

(22) Filed: Sep. 13, 2002

(65) Prior Publication Data

US 2003/0180802 A1 Sep. 25, 2003

Related U.S. Application Data

(60) Provisional application No. 60/322,003, filed on Sep. 13, 2001.

(51) Int. Cl.[7] .......................... C12N 9/02; C12N 15/00; C07H 21/04
(52) U.S. Cl. .......................... 435/189; 435/440; 435/4; 435/6; 435/183; 536/23.2
(58) Field of Search ................... 435/189, 440, 435/4, 6, 183; 536/23.2, 23.1; 530/350

(56) References Cited

PUBLICATIONS

GenBank Accession No. AAF63745; GI: 7546993; Peyou–Ndi et al., Apr. 13, 2000.

GenBank Accession No. AW783527; GI: 7798133; McCarter et al., May 10, 2001.

GenBank Accession No. AW871151; GI: 8005204; McCarter, May 10, 2001.

GenBank Accession No. BE579346; GI: 9830288; McCarter, May 9, 2001.

GenBank Accession No. NP_068373; GI: 13375616; Marquardt et al., Aug. 4, 2001.

GenBank Accession No. NP_037534; GI: 11181775; Stohr et al., Jan. 15, 2003.

*Primary Examiner*—Rao Manjunath
*Assistant Examiner*—Yong D. Pak
(74) *Attorney, Agent, or Firm*—Fish & Richardson P.C.

(57) ABSTRACT

Nucleic acid molecules from nematodes encoding fatty acid desaturase polypeptides are described. Fatty acid desaturase-like polypeptide sequences are also provided, as are vectors, host cells, and recombinant methods for production of fatty acid desaturase-like nucleotides and polypeptides. Also described are screening methods for identifying inhibitors and/or activators of fatty acid desaturase-like polypeptides, as well as methods for antibody production.

3 Claims, 13 Drawing Sheets

Figure 1

```
1/1                             31/11
ATG TCT TAT CTT GAC ACA ACC AAA AAT AAT TTA AAC AAT GGG GGA TCC AAT GAT AAT GGC
 M   S   Y   L   D   T   T   K   N   N   L   N   N   G   G   S   N   D   N   G
61/21                           91/31
AAT GCT TTT TGC AAT GAT AAT GAT TTT GTT GGT AAT AAT GCT GAA TCT GTG GTT AGT AAT
 N   A   F   C   N   D   N   D   F   V   G   N   N   A   E   S   V   V   S   N
121/41                          151/51
GTG GCG GCA CCT AAT GTC GAG GAA TTG CGA ATG TCC GTG CCA CCA GAA TGC TTC GAA AAA
 V   A   A   P   N   V   E   E   L   R   M   S   V   P   P   E   C   F   E   K
181/61                          211/71
CCC TTA ATT CGT TCG ATC TCT TAT TTA ATT TTG GAT TTG GTA ATT ATT TCT GGT CTT TAT
 P   L   I   R   S   I   S   Y   L   I   L   D   L   V   I   I   S   G   L   Y
241/81                          271/91
ATG GTT GTT GGA ATT GTT GAA AAT TAT TTG GGA TTT GTT GGA CTT TTA ATT TGG TAT TGG
 M   V   V   G   I   V   E   N   Y   L   G   F   V   G   L   L   I   W   Y   W
301/101                         331/111
GTT CTC GGA ATG TAT TTA TCC TCT TTA TTT TGT ATT GGG CAT GAT TGT GGG CAC GGA ACT
 V   L   G   M   Y   L   S   S   L   F   C   I   G   H   D   C   G   H   G   T
361/121                         391/131
TTT TCT TCC TAT ACT TGG GTG AAT GAT TTG TTT GGG CAT ATT TCT CAT GCT GTT ATT ATG
 F   S   S   Y   T   W   V   N   D   L   F   G   H   I   S   H   A   V   I   M
421/141                         451/151
GTT CCA TTC TGG CCC TGG CAA AAA TCA CAT CGA CAA CAC CAT CAA TAC ACG GCA CAT TTG
 V   P   F   W   P   W   Q   K   S   H   R   Q   H   H   Q   Y   T   A   H   L
481/161                         511/171
GAT AAA GAT AAA GGA CAC CCT TGG GTT ACA GAA GAG GAG TAT GAA TCA ACT AAT TGG ATT
 D   K   D   K   G   H   P   W   V   T   E   E   E   Y   E   S   S   N   W   I
541/181                         571/191
AAA AAA CAT TTT GCC AAA ATT CCT TTA TCT GGA CTT ATT CGT TGG AAC CCA ATA TAC ACA
 K   K   H   F   A   K   I   P   L   S   G   L   I   R   W   N   P   I   Y   T
601/201                         631/211
ATT GCT GGA CTC CCC GAT GGT TCT CAT TTT TGG CCG TGG TCT AAA TTA TTT GAG AAT AAT
 I   A   G   L   P   D   G   S   H   F   W   P   W   S   K   L   F   E   N   N
661/221                         691/231
GTT GAT AGA ATT AAA TGT GTT GTT AGT GTT TCT GCT TGT TTT CTA TGC TCT TTT GTT ATT
 V   D   R   I   K   C   V   V   S   V   S   A   C   F   L   C   S   F   V   I
721/241                         751/251
CTC TAC TAT ATG AAT TAT AAT TTG TGG AAC TTT TTT AAA TAT TAT TAT GTG CCG TTA ATG
 L   Y   Y   M   N   Y   N   L   W   N   F   F   K   Y   Y   Y   V   P   L   M
781/261                         811/271
TTC CAA GGT TTC TGG ATG GTC ATA ATA ACC TTT TTA CAA CAT CAA GAC GAG CAA ATT GAA
 F   Q   G   F   W   M   V   I   I   T   F   L   Q   H   Q   D   E   Q   I   E
841/281                         871/291
GTT TAT GAA GAA GGG ACT TGG GCA TTT ATG AAA GGG CAG TTA CAG ACT GTT GAT AGA TCT
 V   Y   E   E   G   T   W   A   F   M   K   G   Q   L   Q   T   V   D   R   S
901/301                         931/311
TTT GGA TTT GGA ATA GAC AAA GCA TTG CAT CAC ATA ACT GAC GGT CAT GTA GCC CAT CAT
 F   G   F   G   I   D   K   A   L   H   H   I   T   D   G   H   V   A   H   H
961/321                         991/331
TTC TTT TTT ACT CGT ATT CCT CAT TAT AAT TTA CCT AAA GCT ACG GAA GCT GTT AAA AAG
 F   F   F   T   R   I   P   H   Y   N   L   P   K   A   T   E   A   V   K   K
1021/341                        1051/351
GTT TTG CAA AAA TAC CCT GGC GCA TAT AAA CAT AAA AGT GCA TAT GAC TTT TTA ATT AAA
 V   L   Q   K   Y   P   G   A   Y   K   H   K   S   A   Y   D   F   L   I   K
1081/361                        1111/371
TTT TTA TGG TTA AAT ATT AAA TTG GAC TGT CTT GTT GGT AAA GGT AGC GGT TTA CTT AAA
 F   L   W   L   N   I   K   L   D   C   L   V   G   K   G   S   G   L   L   K
1141/381                        1171/391
TAT CGT TCT ACT GTC CAG AAT GAT GAA CAA CTT AAT AAT AAA AAG GAT AAA TAG
 Y   R   S   T   V   Q   N   D   E   Q   L   N   N   K   K   D   K   *
```

Figure 2

```
1/1                                        31/11
ATG TCT TAT ATT GAC ACA ACC AAA AAT AAT    TTA ATA AAC AAT GGT GGA TAC AAT CCC GGC
 M   S   Y   I   D   T   T   K   N   N      L   I   N   N   G   G   Y   N   P   G
61/21                                      91/31
AAT ATT AAT GAC GAT GGC AGC AGT TCT TAT    CGT CTT TTC AAT GAT GAC AGC AAA TCT GAA
 N   I   N   D   D   G   S   S   S   Y      R   L   F   N   D   D   S   K   S   E
121/41                                     151/51
TTT TAT GGT GGC AAT GCT GAA TCT GCG TCT    TCA AAT ATC GGA GTT TTT AGA CAA GTA CCA
 F   Y   G   G   N   A   E   S   A   S      S   N   I   G   V   F   R   Q   V   P
181/61                                     211/71
AAC GTT GAG GAA TTG CGA ATG TCA GTG CCC    CCA GAA TGT TTT GAC AAG CCT TTA ATT CGT
 N   V   E   E   L   R   M   S   V   P      P   E   C   F   D   K   P   L   I   R
241/81                                     271/91
TCA ATT TCT TAT TTA ATT CTG GAT TTG GTA    ATT ATT TCT GGT CTT TAT ATG GTT GTT GGA
 S   I   S   Y   L   I   L   D   L   V      I   I   S   G   L   Y   M   V   V   G
301/101                                    331/111
ATT GTT GAA AAT TAT TTG GGA TTT GTT GGA    CTT TTA ATT TGG TAT TGG GTT CTC GGA ATG
 I   V   E   N   Y   L   G   F   V   G      L   L   I   W   Y   W   V   L   G   M
361/121                                    391/131
TAT TTA TCC TCT TTA TTT TGT ATT GGG CAT    GAT TGT GGG CAC GGA ACT TTT TCT TCC TAT
 Y   L   S   S   L   F   C   I   G   H      D   C   G   H   G   T   F   S   S   Y
421/141                                    451/151
ACT TGG GTG AAT GAT TTG TTT GGG CAT ATT    TCT CAT GCT GTT ATT ATG GTT CCA TTC TGG
 T   W   V   N   D   L   F   G   H   I      S   H   A   V   I   M   V   P   F   W
481/161                                    511/171
CCC TGG CAA AAA TCA CAT CGA CAA CAC CAT    CAA TAC ACG GCA CAT TTG GAT AAA GAT AAA
 P   W   Q   K   S   H   R   Q   H   H      Q   Y   T   A   H   L   D   K   D   K
541/181                                    571/191
GGA CAC CCT TGG GTT ACA GAA GAG GAG TAT    GAA TCA AGT AAT TGG ATT AAA AAA CAT TTT
 G   H   P   W   V   T   E   E   E   Y      E   S   S   N   W   I   K   K   H   F
601/201                                    631/211
GCC AAA ATT CCT TTA TCT GGA CTT ATT CGT    TGG AAC CCA ATA TAC ACG ATT GCT GGA CTC
 A   K   I   P   L   S   G   L   I   R      W   N   P   I   Y   T   I   A   G   L
661/221                                    691/231
CCC GAT GGT TCT CAT TTT TGG CCG TGG TCT    AAA TTA TTT GAA AAT AAT GTT GAT AGA ATT
 P   D   G   S   H   F   W   P   W   S      K   L   F   E   N   N   V   D   R   I
721/241                                    751/251
AAA TGT GTT GTT AGT GTT TCT GCT TGT TTT    CTA TGC TCT TTT GTT ATT CTC TAC TAT ATG
 K   C   V   V   S   V   S   A   C   F      L   C   S   F   V   I   L   Y   Y   M
781/261                                    811/271
AAT TAT AAT TTG TGG AAC TTT TTT AAA TAT    TAT TAT GTG CCG TTA ATG TTC CAA GGT TTC
 N   Y   N   L   W   N   F   F   K   Y      Y   Y   V   P   L   M   F   Q   G   F
841/281                                    871/291
TGG ATG GTC ATA ATA ACC TTT TTA CAA CAC    CAA GAC GAA CAA ATT GAG GTT TAT GAA GAA
 W   M   V   I   I   T   F   L   Q   H      Q   D   E   Q   I   E   V   Y   E   E
901/301                                    931/311
GGG ACT TGG GCA TTT ATG AAA GGG CAG TTA    CAG ACT GTT GAT AGA TCT TTT GGA TTT GGA
 G   T   W   A   F   M   K   G   Q   L      Q   T   V   D   R   S   F   G   F   G
961/321                                    991/331
ATA GAC AAA GCA TTG CAT CAC ATA ACT GAC    GGT CAT GTA GCC CAT CAT TTC TTT TTT ACT
 I   D   K   A   L   H   H   I   T   D      G   H   V   A   H   H   F   F   F   T
1021/341                                   1051/351
CGT ATT CCT CAT TAT AAT TTA CCT AAA GCT    ACG GAA GCT GTT AAA AAG GTT TTG CAA AAA
 R   I   P   H   Y   N   L   P   K   A      T   E   A   V   K   K   V   L   Q   K
1081/361                                   1111/371
TAC CCT GGC GCA TAT AAA CAT AAA AGT GCA    TAT GAC TTT TTA ATT AAA TTT TTA TGG TTA
 Y   P   G   A   Y   K   H   K   S   A      Y   D   F   L   I   K   F   L   W   L
1141/381                                   1171/391
AAT ATT AAA TTG GAC TGT CTT GTT GGT AAA    GGT AGC GGT TTA CTT AAA TAT CGT TCT ACT
 N   I   K   L   D   C   L   V   G   K      G   S   G   L   L   K   Y   R   S   T
1201/401                                   1231/411
GTC CAG AAT GAT GAA CAA CTT AAT AAT AAA    AAG GAT AAA TAG
 V   Q   N   D   E   Q   L   N   N   K      K   D   K   *
```

Figure 3

```
1/1                                             31/11
ATG TCC CTA ATT TCA TCA AAT ACA ATT GTT GAA ACA ACT AAA ACA AAT GGA AAT ACA ATT
 M   S   L   I   S   S   N   T   I   V   E   T   T   K   T   N   G   N   T   I
61/21                                           91/31
TCT GAT TCT AAC AAC AAA ATT AAT TAT TCC TTC CCT AAT TTA AAT GAA CTT CGA AAT GCG
 S   D   S   N   N   K   I   N   Y   S   F   P   N   L   N   E   L   R   N   A
121/41                                          151/51
ATC CCA GCA GAG TGT TTT GAA AAA TCT CTA ATT CGT TCA CTT TCT TAT TTA ATT TTG GAT
 I   P   A   E   C   F   E   K   S   L   I   R   S   L   S   Y   L   I   L   D
181/61                                          211/71
TTT TTA ATT ATT TAT GGA CTT TAT TTG GTT GTT GGG GTT GTT GAG GAC AAC TTT GGG ATT
 F   L   I   I   Y   G   L   Y   L   V   V   G   V   V   E   D   N   F   G   I
241/81                                          271/91
ATT GGA CTT TTG CTT TGG TAT TGG GTA TTA GGT ATG TTT TTA TTC TCT ATA TTC GCT GTT
 I   G   L   L   L   W   Y   W   V   L   G   M   F   L   F   S   I   F   A   V
301/101                                         331/111
GGA CAC GAT TGT GGG CAC GGA ACT TTT TCT TCC TAT ACT TGG GTA AAT GAT TTG TTT GGG
 G   H   D   C   G   H   G   T   F   S   S   Y   T   W   V   N   D   L   F   G
361/121                                         391/131
CAT GTG GCA CAT GCT CCT ACT ATG GTC CCT TAT TGG CCT TGG CAA AAA TCC CAT AGA TTA
 H   V   A   H   A   P   T   M   V   P   Y   W   P   W   Q   K   S   H   R   L
421/141                                         451/151
CAC CAT CAA TAC ACT GCA CAT TTG GAT AAA GAT ATG AGT CAT CCT TGG ATA CCt GAA AAG
 H   H   Q   Y   T   A   H   L   D   K   D   M   S   H   P   W   I   P   E   K
481/161                                         511/171
CTT TAT TTA TCT TTA AAT TGG ATA TCC AAA CAT TAT CTC AAA TTT CCT TTG ACT GGG TTT
 L   Y   L   S   L   N   W   I   S   K   H   Y   L   K   F   P   L   T   G   F
541/181                                         571/191
GTT AGT TGG ATT CCA TTA TAT ACA ATA TTT GGT ATT CCC GAT GGT TCT CAT TTT TGG CCT
 V   S   W   I   P   L   Y   T   I   F   G   I   P   D   G   S   H   F   W   P
601/201                                         631/211
TGG TCT AAA TTA TTT GAA AAC AAT ACT GAT AGA ATT AAA TGT GCT GTT AGT GTT GCT GCT
 W   S   K   L   F   E   N   N   T   D   R   I   K   C   A   V   S   V   A   A
661/221                                         691/231
TGT TTT CTA TGT GCC TAT ATA GCT TTA TAT TGT TCA AAT TAT AAT TTA TGG ATA TTT TTT
 C   F   L   C   A   Y   I   A   L   Y   C   S   N   Y   N   L   W   I   F   F
721/241                                         751/251
AAA TAT TAT TAT ATT CCG GTT ATG TTC CAA GGT TTC TGG TTA GTT TTG ATT ACT TAT TTA
 K   Y   Y   Y   I   P   V   M   F   Q   G   F   W   L   V   L   I   T   Y   L
781/261                                         811/271
CAA CAC CAT GAC GAA GAG ACT GAA GTT TAT GAA GAT GGA ACG TGG GGG TTT GTG AGA GGG
 Q   H   H   D   E   E   T   E   V   Y   E   D   G   T   W   G   F   V   R   G
841/281                                         871/291
CAG TTA CAG ACA GTT GAT AGA TCT TTT GGA TTT GGA ATA GAC AAA GCA TTG CAT AAC ATA
 Q   L   Q   T   V   D   R   S   F   G   F   G   I   D   K   A   L   H   N   I
901/301                                         931/311
ACT GAC GGT CAT GTA GCC CAT CAC CTC TTT TTT ACG CGT ATT CCA CAT TAC AAT TTA CCC
 T   D   G   H   V   A   H   H   L   F   F   T   R   I   P   H   Y   N   L   P
961/321                                         991/331
AAA GCT ACT GAA GCA GTT AAA AGA ATA TTA ACG GAA AAA TAC CCG GGA ACA TAT AAA TAC
 K   A   T   E   A   V   K   R   I   L   T   E   K   Y   P   G   T   Y   K   Y
1021/341                                        1051/351
AAA AAA TCC TAT GAC TTT TTA ATT GAA TTT TTG TGG TTA AAT ATT AAA CTG GAT TAC CTT
 K   K   S   Y   D   F   L   I   E   F   L   W   L   N   I   K   L   D   Y   L
1081/361                                        1111/371
GTT GGA AAA GGT AGT GGT TTA CTT AGA TAT CGA AAT AAT ATC CGG ACT AAT GAC CAA TCT
 V   G   K   G   S   G   L   L   R   Y   R   N   N   I   R   T   N   D   Q   S
1141/381                                        1171/391
AAA ACA ACA AAA AAG AAT AAT TAA gac ttt aat att ctc gat gtt ttt cat ttt gtt gaa
 K   T   T   K   K   N   N   *
1201/401                                        1231/411
ttt tat ttt ttc ttt aat tta aat ata aaa att att tac tta aaa aaa aaa aaa aaa aag
```

Figure 4

```
1/1                                             31/11
gtt taa tta ccc aag ttt gaa acc ttt gcc gtc ccc tgc tcc att ttc ttt tcc tcc tcc
12557-007001
61/21                                           91/31
ttt tca tca cat ttt cgc ctc ctc ATG TCC CCT CCC TGC TCC TTT TCC CCT TCC TCC GCC
                                    M   S   P   P   C   S   F   S   P   S   S   A
121/41                                          151/51
TCC TCT TCC CCT GAC AGT CCC TCA GCA GAA GGC CAA GCC CAG CAA AAT GGC CAA GTT TTG
 S   S   S   P   D   S   P   S   A   E   G   Q   A   Q   Q   N   G   Q   V   L
                                                211/71
181/61
GCC CCC CGT CCA TTG CCC ACG TGG GAG GAA ATC CGT GCC GCG GTG CCC AAA GAG TGT TTT
 A   P   R   P   L   P   T   W   E   E   I   R   A   A   V   P   K   E   C   F
241/81                                          271/91
GAA AAG TCT CTC CTT CGT TCT CTG TAC TAT TTG GCC ATC GAT TTG CTC GTC ATT GGC TTC
 E   K   S   L   L   R   S   L   Y   Y   L   A   I   D   L   L   V   I   G   F
301/101                                         331/111
CTT TAC GCC GTT GTG CCT TTT GTA GAG ACA AAT TTC GGA CTG ATC GGA CTG TTT TTC TGG
 L   Y   A   V   V   P   F   V   E   T   N   F   G   L   I   G   L   F   F   W
361/121                                         391/131
TAC TGC TTG CTC GGC ATG TTT TTG TCC TCT CTG TTT TGC GTT GGC CAT GAC TGC GGC CAC
 Y   C   L   L   G   M   F   L   S   S   L   F   C   V   G   H   D   C   G   H
421/141                                         451/151
GGC ACT TTT TCC GAT TGG ACA TGG GTC AAC GAC ATT TTC GGC CAT ATT TCC CAC GCT TTG
 G   T   F   S   D   W   T   W   V   N   D   I   F   G   H   I   S   H   A   L
481/161                                         511/171
CTA ATG GTG CCC TTT TGG CCA TGG CAA AAA AGC CAC CGT CAA CAT CAC CAA TTC ACT TCT
 L   M   V   P   F   W   P   W   Q   K   S   H   R   Q   H   H   Q   F   T   S
541/181                                         571/191
CAT GTG GAC AAG GAC AAA GGT CAT CCC TGG GTG TTG GAA GAT GAC TAC GAA GGT GGC GGA
 H   V   D   K   D   K   G   H   P   W   V   L   E   D   D   Y   E   G   G   G
601/201                                         631/211
TGG CTG CGA AAA CAT TTT GCT AAG ATT CCC TTG TCC GGA CTG ATC AGG TGG AAT CCC ATT
 W   L   R   K   H   F   A   K   I   P   L   S   G   L   I   R   W   N   P   I
661/221                                         691/231
TAC ACT GTC GCC GGT CTC CCC GAC GGC TCC CAT TTT TGG CCC TTT TCT CGG CTG TTC TCC
 Y   T   V   A   G   L   P   D   G   S   H   F   W   P   F   S   R   L   F   S
721/241                                         751/251
AAC AAT ACA GAG CGT TTC AAA TGT CTG ATC AGT TCC TCA CTT TGT CTT ATC ACT TCT TGG
 N   N   T   E   R   F   K   C   L   I   S   S   S   L   C   L   I   T   S   W
781/261                                         811/271
GCC ATT TTC GTT TTG CTT GAC CAC AGT CCG TGG GCC TTT CTC AAA TAT TAT TAT GTG CCG
 A   I   F   V   L   L   D   H   S   P   W   A   F   L   K   Y   Y   Y   V   P
841/281                                         871/291
CTG ATG TTT CAG GGC TAT TGG ATG GTG ATC ATC ACA TAT TTG CAA CAT CAG GAC GAG CAA
 L   M   F   Q   G   Y   W   M   V   I   I   T   Y   L   Q   H   Q   D   E   Q
901/301                                         931/311
ATC GAG GTG TAC GAG GAG GGC AAT TGG GCA TTT GTC AAG GGA CAG CTG CAG ACC TAC GAT
 I   E   V   Y   E   E   G   N   W   A   F   V   K   G   Q   L   Q   T   Y   D
961/321                                         991/331
CGC GAG TAC GGT TTT GGC ATT GAT CAC GCC ATG CAT CAC ATT ACG GAT GGT CAC GTG GCG
 R   E   Y   G   F   G   I   D   H   A   M   H   H   I   T   D   G   H   V   A
1021/341                                        1051/351
CAC CAT TTC TTC TTC ACC CGA ATC CCT CAT TAT CAT TTG CCT GAG GCA ACC AAA AGC ATT
 H   H   F   F   F   T   R   I   P   H   Y   H   L   P   E   A   T   K   S   I
1081/361                                        1111/371
CGC AAA ATT ATG GAA AAA TAC CCG GGG GCG TAC AAG CGC AAG TCA AAC TAC GAC TTT CTG
 R   K   I   M   E   K   Y   P   G   A   Y   K   R   K   S   N   Y   D   F   L
1141/381                                        1171/391
CTC CAA TTT CTG TGG ATG AAC GTC AAA TTG GAC TGT TTG GTG GGA AAA GGC AGC GGA CTG
 L   Q   F   L   W   M   N   V   K   L   D   C   L   V   G   K   G   S   G   L
1201/401                                        1231/411
TTG AAG TAT CGG ACA ACG GCA CGA AGG GAA GAG AGG CAG CAA AAG GAG GAC taa gaa aca
 L   K   Y   R   T   T   A   R   R   E   E   R   Q   Q   K   E   D   *
1261/421                                        1291/431
gga ggg agg tcc aac gac aga aca gag agg atg aga ggg gaa aag aaa cga gac gga agg
```

Figure 4 (continued)

```
1321/441                            1351/451
gcg aga gac aca gag gaa gga aag gcg aaa aga aaa aga aaa gtg caa ata ttt att aaa 1381/461                            1411/471
caa tta att taa taa atg aaa cac agt tta ttg ctg ttg ttg tta ttt aaa agt gaa tga 1441/481                            1471/491
atg aat acg gtg gaa aaa aaa aaa aaa aag tac tag tcg acg cgt ggc
```

Figure 5

```
1/1                                     31/11
TAT TGT TGC ATG GGG ATG TTC GGG TCA TCA TTG TTT GTG GTT GGC CAT GAT TGT GGA CAT
 Y   C   C   M   G   M   F   G   S   S   L   F   V   V   G   H   D   C   G   H
61/21                                   91/31
GGT ACA TTT TCC GAA TAT ACG TGG GTC AAC GAT TTT TTC GGA CAT ATT GCT CAT GCT TCA
 G   T   F   S   E   Y   T   W   V   N   D   F   F   G   H   I   A   H   A   S
121/41                                  151/51
CTT TTG GTA CCG TAT TGG CCT TGG CAA AAG TCT CAT AGA CTA CAT CAT CAG TAC ACT TCT
 L   L   V   P   Y   W   P   W   Q   K   S   H   R   L   H   H   Q   Y   T   S
181/61                                  211/71
CAT ATT GAC AAT GAC ATG GGA CAT CCC TGG GTG GTC GAA AAA GAT TTC ATG ACA CGT GGT
 H   I   D   N   D   M   G   H   P   W   V   V   E   K   D   F   M   T   R   G
241/81                                  271/91
TGG ATA ATT CGC AAT TTT TCA AAG ATC CCA CTT TCC GGT TTT ATT CGA TGG AGT CCG ATT
 W   I   I   R   N   F   S   K   I   P   L   S   G   F   I   R   W   S   P   I
301/101                                 331/111
TAC ACA ATA GTT GGT CTA CCA GAC GGC AGC CAC TTT TGG CCT TAT AGT AAA CTT TTC AAT
 Y   T   I   V   G   L   P   D   G   S   H   F   W   P   Y   S   K   L   F   N
361/121                                 391/131
AAC AAT CGC GAA CGA GTG AAA TGT GTT GTT AGT GGT TTG GCA TGT GTA TTT TGT GCT GTG
 N   N   R   E   R   V   K   C   V   V   S   G   L   A   C   V   F   C   A   V
421/141                                 451/151
GTG GCC TTT GTT TTA TGT AGT TGT AGT TGG TAT ACA TTC ATC AAA TAT TAT TAC GTT TCG
 V   A   F   V   L   C   S   C   S   W   Y   T   F   I   K   Y   Y   Y   V   S
481/161                                 511/171
TTA TTG TTT CAA GGC TAT TGG CTT GTT ATC ATA ACT TAT CTA CAA CAC AAC GAT TAC AGC
 L   L   F   Q   G   Y   W   L   V   I   I   T   Y   L   Q   H   N   D   Y   S
541/181                                 571/191
ATA GAG GTT TAC GAG GAA GAT TAC TGG AGT TAT GTA ATG GGG CAA GTA CAA ACC ATT GAT
 I   E   V   Y   E   E   D   Y   W   S   Y   V   M   G   Q   V   Q   T   I   D
601/201                                 631/211
CGA GTT TAT GGT TTT GGT ATT GAT ACA CTG CTA CAT CAT ATT ACT GAT GGA CAC GTG GCC
 R   V   Y   G   F   G   I   D   T   L   L   H   H   I   T   D   G   H   V   A
661/221                                 691/231
CAT CAT TTC TTC TTT ACA AAA ATT CCA CAT TAC CAT TTG ATG GAA GCA ACA GCG GCA ATT
 H   H   F   F   F   T   K   I   P   H   Y   H   L   M   E   A   T   A   A   I
721/241                                 751/251
AGA AAT GTT TTG GAA CCT TAT AAG GCA TAT CGA TGT AAA AGC AAT TCC AAT TTT TTA TTG
 R   N   V   L   E   P   Y   K   A   Y   R   C   K   S   N   S   N   F   L   L
781/261                                 811/271
GAT TAT TTG ACG CTC AAT GTA AAG TTA GAA TAT CTT ATT GGT AAA GGC ACT GGG ATC CTT
 D   Y   L   T   L   N   V   K   L   E   Y   L   I   G   K   G   T   G   I   L
841/281                                 871/291
ACT TAT GCT AGA CAA CAA AAA GAG GAA tga tga ttt gtc aag ttt ttt ttt ttt tgt
 T   Y   A   R   Q   Q   K   E   E   *
901/301                                 931/311
aat gtt ttt aaa tca gtt ttg aaa aaa tga gtt tga aac ttt cat cac ttc agt gtt tta 961/321                                 991/331
caa tgt caa cga ttg gtg gca ttt gta ata agg gtt tgc ttt tac tgt tat gag ttc tgg 1021/341                                1051/351
tgt att agt aat aaa agt ttt tat tcg act aaa aaa aaa aaa aaa aaa
```

Figure 6

```
1/1                                              31/11
att tta tta cgt gat tat ata ata gtt ATG TCG TCT ACC ACT CAA ACA AAA ACC CTT TTA
                                    M   S   S   T   T   Q   T   K   T   L   L
61/21                                            91/31
AAA GAA AAT AAA CAA AAA AAA GAA TTT CCA ACA CTT GAA GAA ATA AAA AAG GCT ATA CCA
K   E   N   K   Q   K   K   E   F   P   T   L   E   E   I   K   K   A   I   P
121/41                                           151/51
GCT GAA TGT TGG GAA AAA AAT GCA TTA AAG TCT ATT TCT TAT CTT GTT TTG GAC TAT GCT
A   E   C   W   E   K   N   A   L   K   S   I   S   Y   L   V   L   D   Y   A
181/61                                           211/71
CTT ATA GCT GGT ATG TAT TTT GCT TTA CCA CTT TCT GAA GGT TAT GGT GGT TTT CTT GGT
L   I   A   G   M   Y   F   A   L   P   L   S   E   G   Y   G   G   F   L   G
241/81                                           271/91
TTA TGT GTT TGG TAT TGG TTA ATA GGT ATG TTT GGA TCA TCA CTT TTT ATT GTT GGA CAT
L   C   V   W   Y   W   L   I   G   M   F   G   S   S   L   F   I   V   G   H
301/101                                          331/111
GAT TGT GGG CAT ACA AAC TTT TCA AAC TAT ACA TGG TTA AAT GAT CTT TGT GGT CAT ATT
D   C   G   H   T   N   F   S   N   Y   T   W   L   N   D   L   C   G   H   I
361/121                                          391/131
GCT CAT GCC CCA ATT TTA GCA CCA TAC TGG CCA TGG CAA AAG TCT CAT AGA CAA CAT CAT
A   H   A   P   I   L   A   P   Y   W   P   W   Q   K   S   H   R   Q   H   H
421/141                                          451/151
CAA TAT ACA TCA CAT TTA GAA AAA GAT AAA GGA CAT CCT TGG ACG ACT GAA GAA GAC TGG
Q   Y   T   S   H   L   E   K   D   K   G   H   P   W   T   T   E   E   D   W
481/161                                          511/171
GTT ACT AAA AAT TTC GTG TTT AAA CAT TTT GCA AAA CTT CCA ATT TCT GGT TTA TTT AGA
V   T   K   N   F   V   F   K   H   F   A   K   L   P   I   S   G   L   F   R
541/181                                          571/191
TGG AAT CCA ATT TAT ACT GGT CTT GGT TTA CCC GAT GGA TCA CAT TTT TGG CCT TAT TCA
W   N   P   I   Y   T   G   L   G   L   P   D   G   S   H   F   W   P   Y   S
601/201                                          631/211
AAA CTT TTT ACA ACA ACA ACA GAA CGT ATT CAA TGT GTT ATT TCT GGA TTA GCA TGT CTT
K   L   F   T   T   T   T   E   R   I   Q   C   V   I   S   G   L   A   C   L
661/221                                          691/231
TTC TGT GCT GGA ATT GCT CTT CAC CTT AAT GAT TAT TCA ATT TAT AAC TTT ATA AAA TAT
F   C   A   G   I   A   L   H   L   N   D   Y   S   I   Y   N   F   I   K   Y
721/241                                          751/251
TAT TAT ATT CCA TGT ATG TTC CAA GGA TTT TGG TTA GTT ATT ATT ACA TAT CTT CAA CAT
Y   Y   I   P   C   M   F   Q   G   F   W   L   V   I   I   T   Y   L   Q   H
781/261                                          811/271
CAA TCA GAA ACA ATT GAA GTT TAT GAA GAA GGA AGC TGG AAT TAT GTT AGA GGA CAA CTT
Q   S   E   T   I   E   V   Y   E   E   G   S   W   N   Y   V   R   G   Q   L
841/281                                          871/291
CAA ACA ATT GAT AGA ACT TAT GGA TTT GGT ATT GAT ACA ATT CTT CAT CAT ATA TCT GAT
Q   T   I   D   R   T   Y   G   F   G   I   D   T   I   L   H   H   I   S   D
901/301                                          931/311
GGT CAT GTT GCT CAT CAT TTC TTC TTT ACA AGA ATT CCT CAT TAT CAT TTG ATG AAA GCT
G   H   V   A   H   H   F   F   F   T   R   I   P   H   Y   H   L   M   K   A
961/321                                          991/331
ACC AAA GCA ATT CAA AAT GTT CTT AAA GAT TAT CCA GGA GCA TAT AAA AGA AAG ACA AAT
T   K   A   I   Q   N   V   L   K   D   Y   P   G   A   Y   K   R   K   T   N
1021/341                                         1051/351
TAT GAT TTT GTT TTT GAA TAT CTT AAA TTA AAC ATT ATT CTT GAA TAT CTT ACT GGT AAA
Y   D   F   V   F   E   Y   L   K   L   N   I   I   L   E   Y   L   T   G   K
1081/361                                         1111/371
GGT TCA GGA GTT CTC CAA TAT CCA AAT GCA AAA AAG GCT AAT AAA GCA TAT taa aag ggt
G   S   G   V   L   Q   Y   P   N   A   K   K   A   N   K   A   Y   *
1141/381                                         1171/391
taa tta ata taa ata taa aaa aaa cag tat ata ctg att ctt tca aat aaa ggc aat agt 1201/401
tat aaa aaa aaa aaa aaa aaa
```

Figure 7

```
1/1                              31/11
gtt taa tta ccc aag ttt gag ggt ATG ACG GTT GCT ACT CAG CTT AAC GCC AAG AAG GCG
                                 M   T   V   A   T   Q   L   N   A   K   K   A
61/21                                      91/31
AAT TTG GAG AAA GCA GAT GTA CCG AAC CTC CCC TCA GTG GGT GAC ATC AGA AAG GCT ATT
N   L   E   K   A   D   V   P   N   L   P   S   V   G   D   I   R   K   A   I
121/41                                     151/51
CCC CCA GAG TGT TTT AAG AAG GAT GCC ATA AAA TCT ATT CGA TAT TTA ATT CAG GAT ATT
P   P   E   C   F   K   K   D   A   I   K   S   I   R   Y   L   I   Q   D   I
181/61                                     211/71
CTC ATT CTA GTC GGT TTC TAT ATT GCT CTT CCT TAC GTC GAA CTC TAT CTC GGC TGG ATC
L   I   L   V   G   F   Y   I   A   L   P   Y   V   E   L   Y   L   G   W   I
241/81                                     271/91
GGT CTG TTT GCT TGG TAT TGG GCC ATT GGA ATT GCC GGC TGT TCT CTG TTC ATC ATC GGT
G   L   F   A   W   Y   W   A   I   G   I   A   G   C   S   L   F   I   I   G
301/101                                    331/111
CAT GAC TGC GGA CAC GGC TCT TTC TCC GAC TAC GTG TGG TTG AAT GAC CTG TGT GGA CAC
H   D   C   G   H   G   S   F   S   D   Y   V   W   L   N   D   L   C   G   H
361/121                                    391/131
ATT GCT CAT GCT CCC ATC CTC GCT CCT TAC TGG CCA TGG CAG AAG AGT CAC AGA CAA CAT
I   A   H   A   P   I   L   A   P   Y   W   P   W   Q   K   S   H   R   Q   H
421/141                                    451/151
CAT CAG TAC ACT TCT CAT CTG GAA AAG GAC AAG GGT CAT CCA TGG GTC ACT CAA AAA GAC
H   Q   Y   T   S   H   L   E   K   D   K   G   H   P   W   V   T   Q   K   D
481/161                                    511/171
TTT GAG GAC AGA ACT ACT ATC GAG AGA TAT TTC TCC ATG ATT CCT TTG TCT GGA TGG CTG
F   E   D   R   T   T   I   E   R   Y   F   S   M   I   P   L   S   G   W   L
541/181                                    571/191
AGA TGG AAC CCC ATC TAC ACA GTC GTT GGT CTT TCC GAT GGA AGT CAC TTT TGG CCA TGG
R   W   N   P   I   Y   T   V   V   G   L   S   D   G   S   H   F   W   P   W
601/201                                    631/211
TCT CGT CTG TTC ACA ACG ACT GAA GAT AGA GTA AAA TGT GCC ATC AGC GGA TTG GCT TGT
S   R   L   F   T   T   T   E   D   R   V   K   C   A   I   S   G   L   A   C
661/221                                    691/231
CTT TTC TGT GGT TCA GTT GCC TTC TAT CTG GCT GAC TAT TCT GTC TAC AAC TGG GTC AAA
L   F   C   G   S   V   A   F   Y   L   A   D   Y   S   V   Y   N   W   V   K
721/241                                    751/251
TAT TAC TTC ATT CCT CTT CTC TTC CAA GGT CTT TTC TTG GTT ATC ATC ACC TAT CTG CAA
Y   Y   F   I   P   L   L   F   Q   G   L   F   L   V   I   I   T   Y   L   Q
781/261                                    811/271
CAT CAG AAT GAA GAC ATT GAG GTA TAC GAG AAC GAC GAA TGG TCT TTC GTA AGA GGA CAA
H   Q   N   E   D   I   E   V   Y   E   N   D   E   W   S   F   V   R   G   Q
841/281                                    871/291
ACT CAA ACC ATC GAC AGA TTC TGG GGT TTC GGA CTT GAC ACA ATC ATG CAC CAC ATA ACT
T   Q   T   I   D   R   F   W   G   F   G   L   D   T   I   M   H   H   I   T
901/301                                    931/311
GAC GGT CAT GTC GCC CAT CAC TTC TTC TTC ACA GCC ATT CCT CAC TAC AAC CTC CTA AAA
D   G   H   V   A   H   H   F   F   F   T   A   I   P   H   Y   N   L   L   K
961/321                                    991/331
GCC ACA GAA CCG ATA AAG AAG GTT CTG GAA CCT CTG AAA GAC ACT CCA TAC GGC TAC AAG
A   T   E   P   I   K   K   V   L   E   P   L   K   D   T   P   Y   G   Y   K
1021/341                                   1051/351
AGC AAA GTC AAC TAC GAC TTT TTG TTC GAA TAC TTC AAA TCC AAC TTC CTT TTT GAT TAT
S   K   V   N   Y   D   F   L   F   E   Y   F   K   S   N   F   L   F   D   Y
1081/361                                   1111/371
TTG GTT CCT AAG AGC AAA GGA GTT CTT CAA TAT CGT GTC GGT GTT GAG AAG TCT CGA AAG
L   V   P   K   S   K   G   V   L   Q   Y   R   V   G   V   E   K   S   R   K
1141/381                                   1171/391
ATC CAA TAA tca cat taa aac tcc ttc tgg cgg gta cct ttc ttt ctc act tac caa taa
I   Q   *
1201/401                                   1231/411
atg ttg gtt agt taa aaa aaa aaa aaa aaa aa
```

Figure 8

```
         ....10....20....30....40....50....60
14  MTVATQ.....LNAKKAN....................LEKADVPN......LP: 23
32  MTIATK.....VNTNKKD....................LDTIKVPE......LP: 23
13  MSSTTQ.....TKTLLK.....................ENKQRKE......PP: 21
12  ..........................................................  
8   MSYLDTTKNN.LNNGGSN.....DNGN...AFCNDN...DVVGNNAESVVSNV....AAP: 44
9   MSYIDTTKNNLINNGGYNPGNINDDGSSSYRLFNDDSKSEPYGGNAESASSNIGVFRQVP: 60
10  MSLISS..NTIVETTKTN......GN....TISDS........NNKINYS......FP: 32
11  MSPPCSPSPSSASSSPDS........P......SAEG...QAQQNGQVLAPR.....PLP: 38

...70....80....90...100...110...120
14  SVGDIRKAIPPECFKKDAIKSIRYLIQDILILVGFYIALRYVELYLGWIGLFAWYWAIGI: 83
32  SVAAVKAAIPEHCFVKDPLTSISYLIKDYVLLAGLYFAVPYIEHYLGWIGLLGWYWAMGI: 83
13  TLEEIKKAIPAECWEKNALKSISYLVLDYALIAGMYFALPLSEGYGGFLGLCVNYWLIGM: 81
12  .........................................................YCCMGM:  6
8   NVEELRMSVPPECFEKPLIRSISYLILDLVISGLYMVVGIVENYLGFVGLLIHYMVLGM:104
9   NVEELRMSVPPECFDKPLIRSISYLILDLVISGLYLVVGVVEDNFGIIGLLLWYMVLGM:120
10  NLNELRNAIPAECFEKSLIRSLSYLILDPLILYGLYLVVGVVEDNFGIIGLLLWYMVLGM: 92
11  TWEEIRAAVPKECFEKSLLRSLYYLAIDLLVIGFLYAVVRFVKTNFGLIGLFFMYCLLGM: 98

...130...140...150...160...170...180
14  AGCELFIIGHDCGMGSFSDIVWLNDLCGHIAHAFILAPYWPWQKSHRQHHQYTSHLEKDK:143
32  VGSALFCVGHDCGHGSFSDIENLNDLCGHLAHAFILAPPHPWQKSHRQHHQYTSHVEKDK:143
13  FGSSLFIVGHDCGHTNFSNYTWLNDLCGHIAHAPILAPYHPWQKSHRQHHQYTSHLEKDK:141
12  FGSSLFVVGHDCGHGTFSEITWVNDFPGHIAHASLLVPYWPWQKSHRLHHQYTSHIDNDM: 66
8   YLSSLFCIGHDCGHGTFSSYTWVNDLPGHISHAVIMVPFWPWQKSHRQHHQITAHLDKDK:164
9   YLSSLFCIGHDCGHGTFSSYTWVNDLPGHISHAVIMVPFWPWQKSHRQHHQITAHLDKDM:180
10  FLFSIFAVGHDCGHGTFSSYTWVNDLFGHVAHARTMVPYWPWQKSHRLHHQITAHLDKDN:152
11  FLSSLFCVGHDCGHGTFSDWTWVNDIFGHISHALLMVPFWPWQKSHRQHHQPTSHVDKDK:158

...190...200...210...220...230...240
14  GHPWVTQKDFEDRTTIERYFSMIPLSGWLRWNPIYTVVGUSDGSHFWPWSRLFTTTEDRV:203
32  GHPWVTEEDYNNATAIEKYFAVIPISGWLRWNPIYTIVGLPDGSHFWPYSKLFETTEDRV:203
13  GHPWTTEEDWVTKNFVFKHFAKLPISGLFRWNPIYTGLGLPDGSHFWPYSKLFITTTERI:201
12  GHPWVVEKDFMTRGHIIRNFSKIPLSGFIRWSPIYTIVGLPDGSHFWPYSKLFNNNRERV:126
8   GHPWVTEEEYESSNMIKKHFAKIPLSGLIRWNPIYTEAGLPDGSHFWPWSKLFENNVDRI:224
9   GHPWVTEEEYESSNMIKKHFAKIPLSGLIRWNPIYTEAGLPDGSHFWPWSKLFENNVDRI:240
10  SHPWIPEKLYLSLNMISKHYLKFPLTGFVSWIPLYTFGIPDGSHFWPWSKLFENNTDRI:212
11  GHPWVLEDDYEGGGMLRKHFAKIPLSGLIRWNPIYTVAGLPDGSHFWPFSRLFSNNTERF:218

...250...260...270...280...290...300
14  KCAISGLACLFCGSVAFYLADYSVYNWVKYYFIPLLFQGLFLVIITFLQHQNEDIEVYEN:263
32  KCAVSGVACAICAYIAFVLCDYSVYTFVKYYYIPLLFQGLILVIITYLQHQNEDIEVYEA:263
13  QCVISGLACLFCAGIALHLNDYSIYNFIKYYYIPCMFQGFWLVIITYLQHQSETIEVYEE:261
12  KCVVSGLACVFCAVVAFVLCSCSWYTFIKYYYVSLLFQGIMLVIITILQHNDISIEVYEE:186
8   KCVVSVSACFLCSFVILYYMNYNLWNFPKYYYVPLMFQGFWMVIITFLQHQDEQIEVYEE:284
9   KCVVSVSACFLCSFVILYYMNYNLWNFPKYYYVPLMFQGFWMVIITFLQHQDEQIEVYEE:300
10  KCAVSVAACFLCAYIALYCSNYNLWIFFKYYYIPVMFQGFWLVLITYLQHHDEETEVYED:272
11  KCLISSSLCLITSWAIFVLLDHSPWAFLKYYVPLMFQGYMMVIITYLQHQDEQIEVYEE:278

...310...320...330...340...350...360
14  DEWSFVRGQTQTIDRFWGFGLDTIMNHITDGHVAHHFFFTAIPHYNLLKATEPIKKVLEP:323
32  DEWGFVRGQTQTIDRHWGFGLDNIMHNITNGHVAHHFFFTKIPMYHLLEATPAIKKALEP:323
13  GSHNYVRGQLQTIDRTYGFGIDTILHHISITDGHVAHHFFFTKIPMYHLMKATKAIQNVLK:320
12  DYWSYVMGQVQTIDRVYGFGIDTLLHHITDGHVAHHFFFTKIPHYHLMEATAAIRNVLEP:246
8   GTWAFHKGQLQTVDRSFGFGIDKALHHITDGHVAHHFFFTRIPHYNLPKATEAVKKVL...:342
9   GTWAFHKGQLQTVDRSFGFGIDKALHHITDGHVAHHFFFTRIPHYNLPKATEAVKKVL...:358
10  GTWGFVRGQLQTVDRSFGFGIDKALHNITDGHVAHHLFFTRIPHYNLPKATEAVKRILT..:331
11  GNWAFVRGQLQTYDREYGFGIDHAMHHITDGHVAHHFFFTRIPHYHLPEATKSIRKLM...:336

...370...380...390...400...410
14  LKDTEYGYKSXVNIDFLPEYFKSNPLFDYLVPKSKGVLQTRVGVE.....KSRKIQ.:374
32  LKDTQYGYIKREVNINWFFKYLHYNVTLDYLTHKAKGVLQIRSGVE...AAKAKKAQ.:376
13  ..DYPGAIKRKTNIDFVPEYIKLNEILEYLTGKGSGVLQIPN.AK.....KANKAI.:368
12  ....YKAYRCKSNSNFLLDYLTLNVKLEYLIGKQTGILTYAR........QQKEE.:289
8   .QKYPGAYKHKSATDFLIKFLWNLNIKLDCLVGKGSGLLKYRSTVQ.NDEQLNNKKDK:397
9   .QKYPGAYKHKSATDFLIKFLWNLNIKLDCLVGKGSGLLKYRSTVQ.NDEQLNNKKDK:413
10  .EKYPGTYKYKKSYDFLIEFLWNLNIKLDYLVGKGSGLLRYANNIRTNDQSKTTKKNN:387
11  .EKYPGAYKRKSNIDFLLQFLMHNVKLDCLVGKGSGLLKYRTTAR..REERQQKED.:389
```

NEMATODE FATTY ACID DESATURASE-LIKE SEQUENCES

RELATED APPLICATION INFORMATION

This application claims priority to provisional application Ser. No. 60/322,003, filed Sep. 13, 2001.

BACKGROUND

Nematodes (derived from the Greek word for thread) are active, flexible, elongate, organisms that live on moist surfaces or in liquid environments, including films of water within soil and moist tissues within other organisms. While only 20,000 species of nematode have been identified, it is estimated that 40,000 to 10 million actually exist. Some species of nematodes have evolved as very successful parasites of both plants and animals and are responsible for significant economic losses in agriculture and livestock and for morbidity and mortality in humans (Whitehead (1998) *Plant Nematode Control*. CAB International, New York).

Nematode parasites of plants can inhabit all parts of plants, including the roots, developing flower buds, leaves, and stems. Plant parasites are classified on the basis of their feeding habits into the broad categories: migratory ectoparasites, migratory endoparasites, and sedentary endoparasites. Sedentary endoparasites, which include the root knot nematodes (*Meloidogyne*) and cyst nematodes (*Globodera* and *Heterodera*) induce feeding sites and establish long-term infections within roots that are often very damaging to crops (Whitehead, supra). It is estimated that parasitic nematodes cost the horticulture and agriculture industries in excess of $78 billion worldwide a year, based on an estimated average 12% annual loss spread across all major crops. For example, it is estimated that nematodes cause soybean losses of approximately $3.2 billion annually worldwide (Barker et al. (1994) *Plant and Soil Nematodes: Societal Impact and Focus for the Future*. The Committee on National Needs and Priorities in Nematology. Cooperative State Research Service, US Department of Agriculture and Society of Nematologists). Several factors make the need for safe and effective nematode controls urgent. Continuing population growth, famines, and environmental degradation have heightened concern for the sustainability of agriculture, and new government regulations may prevent or severely restrict the use of many available agricultural anthelmintic agents.

The situation is particularly dire for high value crops such as strawberries and tomatoes where chemicals have been used extensively to control soil pests. The soil fumigant methyl bromide has been used effectively to reduce nematode infestations in a variety of these specialty crops. It is however regulated under the U.N. Montreal Protocol as an ozone-depleting substance and is scheduled for elimination in 2005 in the United States (Carter (2001) *Califonia Agriculture*, 55(3):2). It is expected that strawberry and other commodity crop industries will be significantly impacted if a suitable replacement for methyl bromide is not found. Presently there are a very small array of chemicals available to control nematodes and they are frequently inadequate, unsuitable, or too costly for some crops or soils (Becker (1999) *Agricultural Research Magazine* 47(3):22–24; U.S. Pat. No. 6,048,714). The few available broad-spectrum nematicides such as Telone (a mixture of 1,3-dichloropropene and chloropicrin) have significant restrictions on their use because of toxicological concerns (Carter (2001) *California Agriculture*, Vol. 55(3):12–18).

Fatty acids are a class of natural compounds that have been investigated as alternatives to the toxic, non-specific organophosphate, carbamate and fumigant pesticides (Stadler et al. (1994) *Planta Medica* 60(2):128–132; U.S. Pat. Nos. 5,192,546; 5,346,698; 5,674,897; 5,698,592; 6,124,359). It has been suggested that fatty acids derive their pesticidal effects by adversely interfering with the nematode cuticle or hypodermis via a detergent (solubilization) effect, or through direct interaction of the fatty acids and the lipophilic regions of target plasma membranes (Davis et al. (1997) *Journal of Nematology* 29(4S):677–684). In view of this general mode of action it is not surprising that fatty acids are used in a variety of pesticidal applications including as herbicides (e.g., SCYTHE by Dow Agrosciences is the C9 saturated fatty acid pelargonic acid), as bactericides and fungicides (U.S. Pat. Nos. 4,771,571; 5,246,716) and as insecticides (e.g., SAFER INSECTICIDAL SOAP by Safer, Inc.).

The phytotoxicity of fatty acids has been a major constraint on their general use in agricultural applications (U.S. Pat. No. 5,093,124) and the mitigation of these undesirable effects while preserving pesticidal activity is a major area of research. The esterification of fatty acids can significantly decrease their phytotoxicity (U.S. Pat. Nos. 5,674,897; 5,698,592; 6,124,359). Such modifications can however lead to dramatic loss of nematicidal activity as is seen for linoleic, linolenic and oleic acid (Stadler et al. (1994) *Planta Medica* 60(2):128–132) and it may be impossible to completely decouple the phytotoxicity and nematicidal activity of pesticidal fatty acids because of their non-specific mode of action. Perhaps not surprisingly, the nematicidal fatty acid pelargonic acid methyl ester (U.S. Pat. Nos. 5,674,897; 5,698,592; 6,124,359) shows a relatively small "therapeutic window" between the onset of pesticidal activity and the observation of significant phytotoxicity (Davis et al. (1997) *J Nematol* 29(4S):677–684). This is the expected result if both the phytotoxicity and the nematicidial activity derive from the non-specific disruption of plasma membrane integrity. Similarly the rapid onset of pesticidal activity seen with many nematicidal fatty acids at therapeutic concentrations (U.S. Pat. Nos. 5,674,897; 5,698,592; 6,124,359) suggests a non-specific mechanism of action, possibly related to the disruption of membranes, action potentials and neuronal activity.

Ricinoleic acid, the major component of castor oil, provides another example of the unexpected effects esterification can have on fatty acid activity. Ricinoleic acid has been shown to have an inhibitory effect on water and electrolyte absorption using everted hamster jejunal and ileal segments (Gaginella et al. (1975) *J Pharmacol Exp Ther* 195(2):355–61) and to be cytotoxic to isolated intestinal epithelial cells (Gaginella et al. (1977) *J Pharmacol Exp Ther* 201(1):259–66). These features are likely the source of the laxative properties of castor oil, which is given as a purgative in humans and livestock, e.g., as a deworming agent. In contrast, the methyl ester of ricinoleic acid is ineffective at suppressing water absorption in the hamster model (Gaginella et al. (1975) *J Pharmacol Exp Ther* 195(2):355–61).

The macrocyclic lactones (e.g., avermectins and milbemycins) and delta-toxins from *Bacillus thuringiensis* (*Bt*) are chemicals that in principle provide excellent specificity and efficacy and should allow environmentally safe control of plant parasitic nematodes. Unfortunately, in practice, these two approaches have proven less effective for agricultural applications against root pathogens. Although certain avermectins show exquisite activity against plant parasitic nematodes these chemicals are hampered by poor bioavailability due to their light sensitivity, degradation by soil microorganisms and tight binding to soil particles (Lasota & Dybas (1990) *Acta Leiden* 59(1-2):217–225; Wright & Perry (1998) Musculature and Neurobiology. In: The Physiology and Biochemistry of Free-Living and Plant-parasitic Nematodes (eds R. N. Perry & D. J. Wright), CAB International 1998). Consequently, despite years of research and extensive use against animal parasitic nematodes, mites and insects (plant and animal applications), macrocyclic lactones (e.g., avermectins and milbemycins) have never been commercially developed to control plant parasitic nematodes in the soil.

*Bt* delta-toxins must be ingested to affect their target organ, the brush border of midgut epithelial cells (Marroquin et al. (2000) *Genetics.* 155(4):1693–1699). Consequently they are not anticipated to be effective against the dispersal, non-feeding, juvenile stages of plant parasitic nematodes in the field. These juvenile stages only commence feeding when a susceptible host has been infected. Thus, *Bt* delta-toxins nematicides may need to penetrate the cuticle in order to be effective. In addition, soil mobility of a relatively large 65–130 kDa protein—the size of typical *Bt* delta-toxins—is expected to be poor and delivery in planta is likely to be constrained by the exclusion of large particles by the feeding tube of certain plant parasitic nematodes such as *Heterodera* (Atkinson et al. (1998) Engineering resistance to plant-parasitic nematodes. In: The Physiology and Biochemistry of Free-Living and Plant-parasitic Nematodes (eds R. N. Perry & D. J. Wright), CAB International 1998).

Many plant species are known to be highly resistant to nematodes. The best documented of these include marigolds (*Tagetes* spp.), rattlebox (*Crotalaria spectabilis*), chrysanthemums (*Chrysanthemum* spp.), castor bean (*Ricinus communis*), margosa (*Azardiracta indica*), and many members of the family *Asteraceae* (family *Compositae*) (Hackney & Dickerson. (1975) *J Nematol* 7(1):84–90). The active principle(s) for this nematicidal activity has not been discovered in all of these examples and no plant-derived products are sold commercially for control of nematodes. In the case of the *Asteraceae*, the photodynamic compound alpha-terthienyl has been shown to account for the strong nematicidal activity of the roots. Castor beans are plowed under as a green manure before a seed crop is set. However, a significant drawback of the castor plant is that the seed contains toxic compounds (such as ricin) that can kill humans, pets, and livestock and is also highly allergenic.

There remains an urgent need to develop environmentally safe, target-specific ways of controlling plant parasitic nematodes. In the specialty crop markets, economic hardship resulting from nematode infestation is highest in strawberries, bananas, and other high value vegetables and fruits. In the high-acreage crop markets, nematode damage is greatest in soybeans and cotton. There are however, dozens of additional crops that suffer from nematode infestation including potato, pepper, onion, citrus, coffee, sugarcane, greenhouse ornamentals and golf course turf grasses.

Nematode parasites of vertebrates (e.g., humans, livestock and companion animals) include gut roundworms, hookworms, pinworms, whipworms, and filarial worms. They can be transmitted in a variety of ways, including by water contamination, skin penetration, biting insects, or by ingestion of contaminated food.

In domesticated animals, nematode control or "de-worming" is essential to the economic viability of livestock producers and is a necessary part of veterinary care of companion animals. Parasitic nematodes cause mortality in animals (e.g., heartworm in dogs and cats) and morbidity as a result of the parasites' inhibiting the ability of the infected animal to absorb nutrients. Parasite-induced nutrient deficiency results in diseased livestock and companion animals (i.e., pets), as well as in stunted growth. For instance, in cattle and dairy herds, a single untreated infection with the brown stomach worm can permanently stunt an animal's ability to effectively convert feed into muscle mass or milk.

Two factors contribute to the need for novel anthelmintics and vaccines for control of parasitic nematodes of animals. First, some of the more prevalent species of parasitic nematodes of livestock are building resistance to the anthelmintic drugs available currently, meaning that these products will eventually lose their efficacy. These developments are not surprising because few effective anthelmintic drugs are available and most have been used continuously. Presently a number of parasitic species has developed resistance to most of the anthelmintics (Geents et al. (1997) Parasitology Today 13:149–151; Prichard (1994) Veterinary Parasitology 54:259–268). The fact that many of the anthelmintic drugs have similar modes of action complicates matters, as the loss of sensitivity of the parasite to one drug is often accompanied by side resistance—that is, resistance to other drugs in the same class (Sangster & Gill (1999) Parasitology Today Vol. 15(4):141–146). Secondly, there are some issues with toxicity for the major compounds currently available.

Human infections by nematodes result in significant mortality and morbidity, especially in tropical regions of Africa, Asia, and the Americas. The World Health Organization estimates 2.9 billion people are infected with parasitic nematodes. While mortality is rare in proportion to total infections (180,000 deaths annually), morbidity is tremendous and rivals tuberculosis and malaria in disability adjusted life year measurements. Examples of human parasitic nematodes include hookworm, filarial worms, and pinworms. Hookworm is the major cause of anemia in millions of children, resulting in growth retardation and impaired cognitive development. Filarial worm species invade the lymphatics, resulting in permanently swollen and deformed limbs (elephantiasis) and invade the eyes causing African Riverblindness. *Ascaris lumbricoides*, the large gut roundworm infects more than one billion people worldwide and causes malnutrition and obstructive bowl disease. In developed countries, pinworms are common and often transmitted through children in daycare.

Even in asymptomatic parasitic infections, nematodes can still deprive the host of valuable nutrients and increase the ability of other organisms to establish secondary infections. In some cases, infections can cause debilitating illnesses and can result in anemia, diarrhea, dehydration, loss of appetite, or death.

While public health measures have nearly eliminated one tropical nematode (the water-borne Guinea worm), cases of other worm infections have actually increased in recent decades. In these cases, drug intervention provided through foreign donations or purchased by those who can afford it remains the major means of control. Because of the high rates of reinfection after drug therapy, vaccines remain the best hope for worm control in humans. There are currently no vaccines available.

Until safe and effective vaccines are discovered to prevent parasitic nematode infections, anthelmintic drugs will continue to be used to control and treat nematode parasitic infections in both humans and domestic animals. Finding effective compounds against parasitic nematodes has been complicated by the fact that the parasites have not been amenable to culturing in the laboratory. Parasitic nematodes are often obligate parasites (i.e., they can only survive in their respective hosts, such as in plants, animals, and/or humans) with slow generation times. Thus, they are difficult to grow under artificial conditions, making genetic and molecular experimentation difficult or impossible. To circumvent these limitations, scientists have used *Caenorhabidits elegans* as a model system for parasitic nematode discovery efforts.

*C. elegans* is a small free-living bacteriovorous nematode that for many years has served as an important model system for multicellular animals (Burglin (1998) *Int. J. Parasitol.*, 28(3): 395–411). The genome of *C. elegans* has been completely sequenced and the nematode shares many general developmental and basic cellular processes with vertebrates (Ruvkin et al. (1998) *Science* 282: 2033–41). This, together with its short generation time and ease of culturing, has made it a model system of choice for higher eukaryotes (Aboobaker et al. (2000) *Ann. Med.* 32: 23–30).

Although *C. elegans* serves as a good model system for vertebrates, it is an even better model for study of parasitic nematodes, as *C. elegans* and other nematodes share unique biological processes not found in vertebrates. For example, unlike vertebrates, nematodes produce and use chitin, have gap junctions comprised of innexin rather than connexin and contain glutamate-gated chloride channels rather than glycine-gated chloride channels (Bargmann (1998) *Science* 282: 2028–33). The latter property is of particular relevance given that the avermectin class of drugs is thought to act at glutamate-gated chloride receptors and is highly selective for invertebrates (Martin (1997) *Vet. J.* 154:11–34).

A subset of the genes involved in nematode specific processes will be conserved in nematodes and absent or significantly diverged from homologues in other phyla. In other words, it is expected that at least some of the genes associated with functions unique to nematodes will have restricted phylogenetic distributions. The completion of the *C. elegans* genome project and the growing database of expressed sequence tags (ESTs) from numerous nematodes facilitate identification of these "nematode specific" genes. In addition, conserved genes involved in nematode-specific processes are expected to retain the same or very similar functions in different nematodes. This functional equivalence has been demonstrated in some cases by transforming *C. elegans* with homologous genes from other nematodes (Kwa et al. (1995) *J. Mol. Biol.* 246:500–10; Redmond et al. (2001) *Mol. Biochem. Parasitol.* 112:125–131). This sort of data transfer has been shown in cross phyla comparisons for conserved genes and is expected to be more robust among species within a phylum. Consequently, *C. elegans* and other free-living nematode species are likely excellent surrogates for parasitic nematodes with respect to conserved nematode processes.

Many expressed genes in *C. elegans* and certain genes in other free-living nematodes can be "knocked out" genetically by a process referred to as RNA interference (RNAi), a technique that provides a powerful experimental tool for the study of gene function in nematodes (Fire et al. (1998) *Nature* 391(6669):806–811; Montgomery et al. (1998) *Proc. Natl. Acad Sci USA* 95(26):15502–15507). Treatment of a nematode with double-stranded RNA of a selected gene can destroy expressed sequences corresponding to the selected gene thus reducing expression of the corresponding protein. By preventing the translation of specific proteins, their functional significance and essentiality to the nematode can be assessed. Determination of essential genes and their corresponding proteins using *C. elegans* as a model system will assist in the rational design of anti-parasitic nematode control products.

SUMMARY

The invention features nucleic acid molecules encoding *Meloidogyne incognita*, *Heterodera glycines*, *Dirofilaria immitis*, *Strongyloides stercoralis* and *Rhabditella axei* fatty acid desaturases and other nematode fatty acid desaturase-like proteins. *M. incognita* is a Root Knot Nematode that causes substantial damage to several crops, including cotton, tobacco, pepper, and tomato. *H. glycines*, referred to as Soybean Cyst Nematode, is a major pest of soybean. *D. immitis* (dog heartworm) and *S. stercoralis* (human threadworm) are mammalian parasites. *R. axei* is a free-living nematode that serves as a model for parasitic nematodes. In part, the fatty acid desaturase-like nucleic acids and polypeptides of the invention allow for the identification of a nematode species, and for the identification of compounds that bind to or alter the activity of fatty acid desaturase-like polypeptides. Such compounds may provide a means for combating diseases and infestations caused by nematodes, particularly those caused by *M. incognita* (e.g., in tobacco, cotton, pepper, or tomato plants), *H. glycines* (e.g., in soybeans), *D. immitis* (e.g., in dogs) and *S. stercoralis* (e.g., in humans).

The invention is based, in part, on the identification of cDNAs encoding *M. incognita* fatty acid desaturases (SEQ ID NO: 1, SEQ ID NO: 2 and SEQ ID NO: 3). These 1194, 1242 and 1260 nucleotide cDNAs have 1191, 1239 and 1161 nucleotide open reading frames encoding 397, 413 and 387 amino acid polypeptides (SEQ ID NO: 8, SEQ ID NO: 9 and SEQ ID NO: 10) respectively.

The invention is also based, in part, on the identification of a cDNA encoding *H. glycines* fatty acid desaturase (SEQ ID NO: 4). This 1488 nucleotide cDNA has a 1167 nucleotide open reading frame encoding a 389 amino acid polypeptide (SEQ ID NO: 11).

The invention is also based, in part, on the identification of a partial cDNA fragment encoding *D. immitis* fatty acid desaturase (SEQ ID NO: 5). This 1068 nucleotide cDNA has a 867 nucleotide open reading frame encoding a 289 amino acid polypeptide (SEQ ID NO: 12).

The invention is also based, in part, on the identification of a cDNA encoding *S. stercoralis* fatty acid desaturase (SEQ ID NO: 6). This 1221 nucleotide cDNA has a 1104 nucleotide open reading frame encoding a 368 amino acid polypeptide (SEQ ID NO: 13).

The invention is also based, in part, on the identification of a cDNA encoding *R. axei* fatty acid desaturase (SEQ ID NO: 7). This 1233 nucleotide cDNA has a 1122 nucleotide open reading frame encoding a 374 amino acid polypeptide (SEQ ID NO: 14).

In one aspect, the invention features novel nematode fatty acid desaturase-like polypeptides. Such polypeptides include purified polypeptides having the amino acid sequences set forth in SEQ ID NO: 8, 9, 10, 11, 12, 13 and 14. Also included are polypeptides having an amino acid sequence that is at least about 70%, 75%, 80%, 85%, 90%, 95%, or 98% identical to SEQ ID NO: 8, 9, 10, 11, 12, 13 or 14. The purified polypeptides can be encoded by a nematode gene, e.g., a nematode gene other than a *C. elegans* gene. For example, the purified polypeptide has a sequence other than SEQ ID NO: 32 (*C. elegans* fatty acid desaturase). The purified polypeptides can further include a heterologous amino acid sequence, e.g., an amino-terminal or carboxy-terminal sequence. Also featured are purified polypeptide fragments of the aforementioned fatty acid desaturase-like polypeptides, e.g., a fragment of at least about 20, 30, 40, 50, 75, 100, 125, 150, 200, 250, 300, 325, 350, 375, 395, 400 amino acids. Non-limiting examples of such fragments include: fragments from about amino acid 1 to 50, 1 to 75, 1 to 92, 1 to 96, 1 to 100, 1 to 125, 1 to 399, 51 to 100, 92 to 150, 96 to 150, 92 to 400, 200 to 300, and 1 to 380 of SEQ ID NO: 8, 9, 10, 11, 12, 13 and 14. The polypeptide or fragment thereof can be modified, e.g., processed, truncated, modified (e.g. by glycosylation, phosphorylation, acetylation, myristylation, prenylation, palmitoylation, amidation, addition of glycerophosphatidyl inositol), or any combination of the above. These various polypeptide fragments can be used for a variety of purposes, including for the eliciting of antibodies directed against a fatty acid desaturase-like polypeptide.

In another aspect, the invention features novel isolated nucleic acid molecules encoding nematode fatty acid desaturase-like polypeptides. Such isolated nucleic acid molecules include nucleic acids comprising, consisting of or consisting essentially of the nucleotide sequence set forth in SEQ ID NO: 1, 2, 3, 4, 5, 6 and 7. Also included are isolated nucleic acid molecules having the same sequence as or encoding the same polypeptide as a nematode fatty acid desaturase-like gene (other than *C. elegans* fatty acid desaturase-like genes).

Also featured are: 1) isolated nucleic acid molecules having a strand that hybridizes under low stringency conditions to a single stranded probe of the sequences of SEQ ID NO: 1, 2, 3, 4, 5, 6 or 7 or their complements and, optionally, encodes polypeptides of between 375 and 425 amino acids and preferably have Δ12 fatty acid desaturase activity; 2) isolated nucleic acid molecules having a strand that hybridizes under high stringency conditions to a single stranded probe of the sequence of SEQ ID NO: 1, 2, 3, 4, 5, 6 and/or 7 or their complements and, optionally, encodes polypeptides of between 375 and 425 amino acids and preferably have Δ12 fatty acid desaturase activity; 3) isolated nucleic acid fragments of a fatty acid desaturase-like nucleic acid molecule, e.g., a fragment of SEQ ID NO: 1, 2, 3, 4, 5, 6 or 7 that is about 230, 435, 450, 500, 600, 700, 800, 900, 1000, 1200, 1400, 1450 or more nucleotides in length or ranges between such lengths; and 4) oligonucleotides that are complementary to a fatty acid desaturase-like nucleic acid molecule or a fatty acid desaturase-like nucleic acid complement, e.g., an oligonucleotide of about 10, 15, 18, 20, 22, 24, 28, 30, 35, 40, 50, 60, 70, 80, or more nucleotides in length. Exemplary oligonucleotides are oligonucleotides which anneal to a site located between nucleotides about 1 to 24, 1 to 48, 1 to 60, 1 to 120, 24 to 48, 24 to 60, 49 to 60, 61 to 180, 145 to 165, 165 to 185, 1260 to 1280, 1281 to 1300, 1301 to 1320, 1321 to 1340, 1341 to 1360, 1361 to 1380, 1381 to 1400, 1401 to 1420, 1421 to 1456 of SEQ ID NO: 1, 2, 3, 4, 5, 6 or 7. Such nucleic acid fragments are useful for detecting the presence of fatty acid desaturase-like mRNA. Nucleic acid fragments include the following non-limiting examples: nucleotides about 1 to 200, 100 to 300, 200 to 400, 300 to 500, 400 to 600, 500 to 700, 600 to 800, 700 to 900, 800 to 1000, 900 to 1100, 1000 to 1200, 1100 to 1300, 1200 to 1400, 1300 to 1456 of SEQ ID NO: 1, 2, 3, 4, 5, 6 or 7. Also within the invention are nucleic acid molecules that hybridize under stringent conditions to nucleic acid molecules comprising SEQ ID NO: 1, 2, 3, 4, 5, 6 or 7 and comprise 3,000, 2,000, 1,000 or fewer nucleotides and preferably encode a polypeptide having Δ12 fatty acid desaturase activity and/or have a sequence corresponding to that of a naturally occurring nematode. The isolated nucleic acid can further include a heterologous promoter operably linked to the fatty acid desaturase-like nucleic acid molecule.

A molecule featured herein can be from a nematode of the class *Araeolaimida, Ascaridida, Chromadorida, Desmodorida, Diplogasterida, Monhysterida, Mononchida, Oxyurida, Rhigonematida, Spirurida, Enoplia, Desmoscolecidae, Rhabditida,* or *Tylenchida*. Alternatively, the molecule can be from a species of the class Rhabditida, particularly a species other than *C. elegans*.

In another aspect, the invention features a vector, e.g., a vector containing an aforementioned nucleic acid. The vector can further include one or more regulatory elements, e.g., a heterologous promoter. The regulatory elements can be operably linked to the fatty acid desaturase-like nucleic acid molecules in order to express a fatty acid desaturase-like nucleic acid molecule. In yet another aspect, the invention features a transgenic cell or transgenic organism having in its genome a transgene containing an aforementioned fatty acid desaturase-like nucleic acid molecule and a heterologous nucleic acid, e.g., a heterologous promoter.

In still another aspect, the invention features an antibody, e.g., an antibody, antibody fragment, or derivative thereof that binds specifically to an aforementioned polypeptide. Such antibodies can be polyclonal or monoclonal antibodies. The antibodies can be modified, e.g., humanized, rearranged as a single-chain, or CDR-grafted. The antibodies may be directed against a fragment, a peptide, or a discontinuous epitope from a fatty acid desaturase-like polypeptide.

In another aspect, the invention features a method of screening for a compound that binds to a nematode fatty acid desaturase-like polypeptide, e.g., an aforementioned polypeptide. The method includes providing the nematode polypeptide; contacting a test compound to the polypeptide; and detecting binding of the test compound to the nematode polypeptide. In one embodiment, the method further includes contacting the test compound to a mammalian or plant fatty acid desaturase-like polypeptide; and detecting binding of the test compound to the mammalian or plant fatty acid desaturase-like polypeptide. A test compound that binds the nematode fatty acid desaturase-like polypeptide with at least 2-fold, 5-fold, 10-fold, 20-fold, 50-fold, or 100-fold affinity greater relative to its affinity for the mammalian (e.g., a human) or plant fatty acid desaturase-like polypeptide can be identified.

Alternatively, the compounds can bind to the mammalian or plant fatty acid desaturase with affinity similar to that of the nematode fatty acid desaturase, but not be significantly detrimental to a plant and/or animal.

The invention also features methods for identifying compounds that alter the activity of a nematode fatty acid desaturase-like polypeptide. The method includes contacting the test compound to the nematode fatty acid desaturase-like polypeptide and detecting a fatty acid desaturase-like activity. A decrease in the level of fatty acid desaturase-like activity of the polypeptide relative to the level of fatty acid desaturase-like activity of the polypeptide in the absence of the test compound is an indication that the test compound is an inhibitor of the fatty acid desaturase-like activity. In still another embodiment, the method further includes contacting a nematode fatty acid desaturase polypeptide with a test compound such as an allosteric inhibitor, a substrate analog, other analogs, or other types of inhibitors that prevent binding of the fatty acid desaturase-like polypeptide to other molecules or proteins ("fatty acid desaturase-like polypeptide binding partners"). A change in activity or fatty acid desaturase-like polypeptide binding of proteins normally bound by the fatty acid desaturase is an indication that the test compound is an inhibitor of the fatty acid desaturase-like activity or is an inhibitor of the interaction of the fatty acid desaturase-like polypeptide with one of its binding partners. Such inhibitory compounds are potentially selective agents for reducing the viability, growth, development or reproduction of a nematode expressing a fatty acid desaturase-like polypeptide, e.g., *M. incognita, H. glycines, D. immitis, S. stercoralis* or *R. axei*. These methods can also include contacting the test compound with a plant or mammalian (e.g., as human) fatty acid desaturase-like polypeptide; and detecting a fatty acid desaturase-like activity of the plant or mammalian fatty acid desaturase-like polypeptide. A compound that decreases nematode fatty acid desaturase activity to a greater extent than it decreases a plant or mammalian fatty acid desaturase-like polypeptide activity is a candidate selective inhibitor of nematode viability, growth or reproduction. A desirable compound can exhibit 2-fold, 5-fold, 10-fold, 20-fold, 50-fold, 100-fold or greater selective activity against the nematode polypeptide. Any suitable assay can be used to measure fatty acid desaturase activity, including that of Banas et al. (*Physiology, Biochemistry and Molecular Biology of Plant Lipids*, Williams et al., eds., Kluwer Academic, Dordrecht, Netherlands, 1996, pages 57–59).

Another featured method is a method of screening for a compound that alters an activity of a fatty acid desaturase-like polypeptide or alters binding or regulation of other polypeptides by fatty acid desaturase. Thus, the activity of the fatty acid desaturase can be measured directly by monitoring the substrate or product of the fatty acid desaturase or indirectly by measuring the activity (e.g., monitoring the substrate or product) of an enzyme that acts downstream of fatty acid desaturase. Thus, the methods of the invention include providing a fatty acid desaturase polypeptide; contacting a test compound to the polypeptide; and detecting a fatty acid desaturase-like activity of the polypeptide or the activity of polypeptides bound or regulated by the fatty acid desaturase, wherein a change in activity of the fatty acid desaturase-like polypeptide or other downstream polypeptides relative to the fatty acid desaturase-like activity of the polypeptide or downstream polypeptides in the absence of the test compound is an indication that the test compound alters the activity of the polypeptide(s). Similarly, the method includes providing the polypeptide; contacting a test compound to the polypeptide; and detecting a fatty acid desaturase-like activity or the resulting unsaturated fatty acid products, wherein a change in activity of fatty acid desaturase-like polypeptides or the resulting unsaturated fatty acid products relative to the fatty acid desaturase-like activity of the polypeptide or the level of fatty acid products in the absence of the test compound is an indication that the test compound alters the activity of the polypeptide(s).

The methods of the invention can include contacting the test compound to a plant or mammalian (e.g., a human) fatty acid desaturase-like polypeptide and measuring the fatty acid desaturase-like activity of the plant or mammalian fatty acid desaturase-like polypeptide or other polypeptides affected or regulated by the fatty acid desaturase or the resulting unsaturated fatty acid products. A test compound that alters the activity of the nematode fatty acid desaturase-like polypeptide (or the level of fatty acid products) at a given concentration and that does not substantially alter the activity of the plant or mammalian fatty acid desaturase-like polypeptide, downstream polypeptides, or level of fatty acid products at the same given concentration can be identified. Thus, the methods of the invention can be used to identify candidate compounds that are relatively selective for one or more nematode fatty acid desaturase-like polypeptides relative to one or more mammalian and or plant fatty acid desaturase-like polypeptides. An additional method includes screening for both binding to a fatty acid desaturase-like polypeptide and for an alteration in the activity of a fatty acid desaturase-like polypeptide.

The methods of the invention include the identification of compounds that inhibit both nematode and plant fatty acid desaturase-like polypeptides. Such compounds can be useful for treatment of prevention of nematode infection of plants because plants are often not significantly impaired by inhibition of the activity of a fatty acid desaturase-like polypeptide. Moreover, such inhibitors can be administered to a mammal for treatment or prevention of infection by a nematode.

Yet another featured method is a method of screening for a compound that alters the viability or fitness of a transgenic cell or organism (e.g., a nematode). The transgenic cell or organism has a transgene that expresses a fatty acid desaturase-like polypeptide. The method includes contacting a test compound to the transgenic cell or organism and detecting changes in the viability or fitness of the transgenic cell or organism. This alteration in viability or fitness can be measured relative to an otherwise identical cell or organism that does not harbor the transgene.

The invention also features compounds that are relatively selective inhibitors of one or more nematode fatty acid desaturase-like polypeptides relative to one or more plant or animal fatty acid desaturase-like polypeptides. The compounds can have a $K_i$ for a nematode fatty acid desaturase that is 10-fold, 100-fold, 1,000-fold or more lower than for a plant or animal fatty acid desaturase-like polypeptides, e.g., a host plant or host animal of the nematode. The invention further features relatively non-selective inhibitors as well as completely non-selective inhibitors.

Also featured is a method of screening for a compound that alters the expression of a nematode nucleic acid encoding a fatty acid desaturase-like polypeptide or nucleic acid encoding a nematode fatty acid desaturase-like polypeptide, e.g., a nucleic acid encoding a *M. incognita, H. glycines, D. immitis, S. stercoralis* or *R. axei* fatty acid desaturase-like polypeptide. The method includes contacting a cell, e.g., a nematode cell, with a test compound and detecting expression of a nematode nucleic acid encoding a fatty acid desaturase-like polypeptide, e.g., by hybridization to a probe complementary to the nematode mRNA encoding an fatty acid desaturase-like polypeptide or by contacting polypeptides isolated from the cell with a compound, e.g., antibody that binds a fatty acid desaturase-like polypeptide.

In yet another aspect, the invention features a method of treating a disorder (e.g., an infection) caused by a nematode, e.g., *M. incognita, H. glycines, D. immitis* or *S. stercoralis*, in a subject, e.g., a host plant or host animal. The method includes administering to the subject an effective amount of an inhibitor of a fatty acid desaturase-like polypeptide activity or an inhibitor of expression of a fatty acid desaturase-like polypeptide. Non-limiting examples of such inhibitors include: an antisense nucleic acid (or PNA) to a fatty acid desaturase-like nucleic acid, an antibody to a fatty acid desaturase-like polypeptide, an analog of a natural substrate of a fatty acid desaturase, a fatty acid, or a small molecule identified as a fatty acid desaturase-like polypeptide inhibitor, e.g., an inhibitor identified by a method described herein.

In another aspect, methods for desaturating fatty acids to Δ12 fatty acids are provided. Such methods can include the steps of: (a) providing a cell that harbors a fatty acid desaturase polypeptide; and (b) growing the cell under conditions in which the fatty acid desaturase polypeptide desaturates a fatty acid to produce a corresponding Δ12 unsaturated fatty acid.

In still another aspect, methods of inhibiting nematode (e.g., *M. incognita, H. glycines, D. immitis, S. stercoralis* or *R. axei*) Δ12 fatty acid desaturase(s) are provided. Such methods can include the steps of: (a) providing a nematode that expresses a Δ12 fatty acid desaturase-like enzyme; (b) contacting the nematode with fatty acid analogs or other compounds that inhibit the enzyme. Also provided are methods of rescuing the effect of the inhibitor. Such methods comprise the steps of: (a) inhibiting the enzyme and (b) providing Δ12 unsaturated fatty acids exogenously.

In another aspect, methods of reducing the viability or fecundity or slowing the growth or development or inhibiting the infectivity of a nematode using a fatty acid analog or inhibitor of a fatty acid desaturase are provided. Such methods comprise the steps of (a) providing a nematode that expresses a Δ12 fatty acid desaturase; (b) contacting the nematode with specific inhibitory fatty acid analogs or inhibitors of a Δ12 fatty acid desaturase; (c) reducing the viability or fecundity of the nematode. Also provided are methods of rescuing the effect of the fatty acid desaturase inhibitors or other inhibitors. Such methods can involve contacting the nematode with Δ12 unsaturated fatty acids exogenously.

In another aspect, methods of inhibiting a Δ12 fatty acid desaturase using RNA interference methods are provided. Such methods comprise the steps of (a) providing a nematode that contains a Δ12 fatty acid desaturase like gene; (b) contacting the nematode with double stranded RNA (dsRNA). Such methods can be used to reduce viability or fecundity, to slow growth or development, or to inhibit infectivity. In another aspect, methods of rescuing the effect of RNA interference by supplying specific Δ12 unsaturated fatty acids are provided.

The methods of the invention include a method for identifying an inhibitor of a fatty acid desaturase-like polypeptide, the method comprising: (a) providing a cell expressing a fatty acid desaturase-like polypeptide; (b) contacting the cell with a test compound; (c) measuring the fatty acid desaturase-like polypeptide activity of the cell, wherein a change in fatty acid desaturase-like polypeptide activity of the cell relative to the fatty acid desaturase-like polypeptide activity of the cell in the absence of the test compound is an indication that the test compound alters the activity of the fatty acid desaturase-like polypeptide.

The methods of the invention further include a method for identifying an inhibitor of a fatty acid desaturase-like polypeptide, the method comprising: (a) providing a nematode expressing a fatty acid desaturase-like polypeptide; (b) contacting the nematode with a test compound; (c) measuring the fatty acid desaturase-like polypeptide activity of the nematode, wherein a change in fatty acid desaturase-like polypeptide activity of the nematode relative to the fatty acid desaturase-like polypeptide activity of the nematode in the absence of the test compound is an indication that the test compound alters the activity of the fatty acid desaturase-like polypeptide.

Another method for identifying an inhibitor of a fatty acid desaturase-like polypeptide comprises: (a) providing a cell expressing a fatty acid desaturase-like polypeptide; (b) contacting the cell with a test compound; (c) measuring the viability of the cell in the presence of the test compound; and (d) comparing the viability of the cell in the presence of the test compound to the viability of the cell in the presence of the test compound and a product of the fatty acid desaturase-like polypeptide, wherein greater viability in the presence of the test compound and the product compared to viability in the presence of the test compound is an indication that the test compound alters the activity of the fatty acid desaturase-like polypeptide. The invention features a method for identifying an inhibitor of a fatty acid desaturase-like polypeptide, the method comprising: (a) providing a nematode expressing a fatty acid desaturase-like polypeptide; (b) contacting the nematode with a test compound; (c) measuring the viability or the fecundity of the nematode in the presence of the test compound; and (d) comparing the viability or fecundity of the nematode in the presence of the test compound to the viability or fecundity of the nematode in the presence of the test compound and a product of the fatty acid desaturase-like polypeptide, wherein greater viability or fecundity in the presence of the test compound and the product compared to viability or fecundity in the presence of the test compound is an indication that the test compound alters the activity of the fatty acid desaturase-like polypeptide. In preferred embodiments the product is linoleic acid.

The invention also features inhibitors identified by the screening methods disclosed herein.

The invention features a method for reducing the viability, growth, or fecundity of a nematode, the method comprising exposing the nematode to an agent that inhibits the activity of a fatty acid desaturase-like polypeptide (e.g., a Δ12 fatty acid desaturase) and a method for protecting a plant from a nematode infection, the method comprising applying to the plant or to seeds of the plant an inhibitor of a nematode fatty acid desaturase-like polypeptide. The invention also features a method for protecting a mammal from a nematode infection, the method comprising administering to the mammal an inhibitor of a nematode fatty acid desaturase-like polypeptide (e.g., a Δ12 fatty acid desaturase). In preferred embodiments the inhibitor does not significantly inhibit the activity of a fatty acid desaturase-like polypeptide expressed by the plant or at least does not do so to the extent that the growth of the plant is impaired.

A "purified polypeptide", as used herein, refers to a polypeptide that has been separated from other proteins, lipids, and nucleic acids with which it is naturally associated. The polypeptide can constitute at least 10, 20, 50 70, 80 or 95% by dry weight of the purified preparation.

An "isolated nucleic acid" is a nucleic acid, the structure of which is not identical to that of any naturally occurring nucleic acid, or to that of any fragment of a naturally occurring genomic nucleic acid spanning more than three separate genes. The term therefore covers, for example: (a) a DNA which is part of a naturally occurring genomic DNA molecule but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of different (i) DNA molecules, (ii) transfected cells, or (iii) cell clones in a DNA library such as a cDNA or genomic DNA library. Isolated nucleic acid molecules according to the present invention further include molecules produced synthetically, as well as any nucleic acids that have been altered chemically and/or that have modified backbones.

Although the phrase "nucleic acid molecule" primarily refers to the physical nucleic acid molecule and the phrase "nucleic acid sequence" refers to the sequence of the nucleotides in the nucleic acid molecule, the two phrases can be used interchangeably.

The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example, by column chromatography, polyacrylamide gel electrophoresis, or HPLC analysis.

The "percent identity" of two amino acid sequences or of two nucleic acids is determined using the algorithm of Karlin and Altschul (1990) *Proc. Natl. Acad. Sci. USA* 87:2264–68, modified as in Karlin and Altschul (1993) *Proc. Natl. Acad. Sci. USA* 90:5873–77. Such an algorithm is incorporated into the BLASTN and BLASTX programs (version 2.0 and 2.1) of Altschul et al. (1990). *J. Mol. Biol.* 215:403–10. BLAST nucleotide searches can be performed with the BLASTN program, score=100, wordlength=12 to obtain nucleotide sequences homologous to the nucleic acid molecules of the invention. BLAST protein searches can be performed with the BLASTX program, score=50, wordlength=3 to obtain amino acid sequences homologous to the protein molecules of the invention. Where gaps exist between two sequences, Gapped BLAST can be utilized as described in Altschul et al. (1997) *Nucleic Acids Res.* 25:3389–3402. When utilizing BLAST and Gapped BLAST programs for the determination of percent identity of amino acid sequences or nucleotide sequences, the default parameters of the respective programs can be used. The programs are available on the Internet at: www.ncbi.nlm.nih.gov.

As used herein, the term "transgene" means a nucleic acid sequence (encoding, e.g., one or more subject polypeptides), which is partly or entirely heterologous, i.e., foreign, to the transgenic plant, animal, or cell into which it is introduced, or, is homologous to an endogenous gene of the transgenic plant, animal, or cell into which it is introduced, but which is designed to be inserted, or is inserted, into the plant's genome in such a way as to alter the genome of the cell into which it is inserted (e.g., it is inserted at a location which differs from that of the natural gene or its insertion results in a knockout). A transgene can include one or more transcriptional regulatory sequences and other nucleic acid sequences, such as introns, that may be necessary for optimal expression of the selected nucleic acid, all operably linked to the selected nucleic acid, and may include an enhancer sequence.

As used herein, the term "transgenic cell" refers to a cell containing a transgene.

As used herein, a "transgenic plant" is any plant in which one or more, or all, of the cells of the plant includes a transgene. The transgene can be introduced into the cell, directly or indirectly by introduction into a precursor of the cell, by way of deliberate genetic manipulation, such as by T-DNA mediated transfer, electroporation, or protoplast transformation. The transgene may be integrated within a chromosome, or it may be extrachromosomally replicating DNA.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as a leaf, root, seed, or stem.

As used herein, the terms "hybridizes under stringent conditions" and "hybridizes under high stringency conditions" refer to conditions for hybridization in 6× sodium chloride/sodium citrate (SSC) buffer at about 45° C., followed by two washes in 0.2×SSC buffer, 0.1% SDS at 60° C. or 65° C. As used herein, the term "hybridizes under low stringency conditions" refers to conditions for hybridization in 6×SSC buffer at about 45° C., followed by two washes in 6×SSC buffer, 0.1% (w/v) SDS at 50° C.

A "heterologous promoter", when operably linked to a nucleic acid sequence, refers to a promoter which is not naturally associated with the nucleic acid sequence.

As used herein, an agent with "anthelmintic activity" is an agent, which when tested, has measurable nematode-killing activity or results in reduced fertility or sterility in the nematodes such that fewer viable or no offspring result, or compromises the ability of the nematode to infect or reproduce in its host, or interferes with the growth or development of a nematode. In the assay, the agent is combined with nematodes, e.g., in a well of microtiter dish having agar media or in the soil containing the agent. Staged adult nematodes are placed on the media. The time of survival, viability of offspring, and/or the movement of the nematodes are measured. An agent with "anthelminthic activity" can, for example, reduce the survival time of adult nematodes relative to unexposed similarly staged adults, e.g., by about 20%, 40%, 60%, 80%, or more. In the alternative, an agent with "anthelminthic activity" may also cause the nematodes to cease replicating, regenerating, and/or producing viable progeny, e.g., by about 20%, 40%, 60%, 80%, or more.

As used herein, the term "binding" refers to the ability of a first compound and a second compound that are not covalently linked to physically interact. The apparent dissociation constant for a binding event can be 1 mM or less, for example, 10 nM, 1 nM, 0.1 nM or less.

As used herein, the term "binds specifically" refers to the ability of an antibody to discriminate between a target ligand and a non-target ligand such that the antibody binds to the target ligand and not to the non-target ligand when simultaneously exposed to both the given ligand and non-target ligand, and when the target ligand and the non-target ligand are both present in molar excess over the antibody.

As used herein, the term "altering an activity" refers to a change in level, either an increase or a decrease in the activity, (e.g., an increase or decrease in the ability of the polypeptide to bind or regulate other polypeptides or molecules) particularly a fatty acid desaturase-like or fatty acid desaturase activity (e.g., the ability to introduce a double bond at the $\Delta 12$ position of a fatty acid). The change can be detected in a qualitative or quantitative observation. If a quantitative observation is made, and if a comprehensive analysis is performed over a plurality of observations, one skilled in the art can apply routine statistical analysis to identify modulations where a level is changed and where the statistical parameter, the p value, is, for example, less than 0.05.

In part, the nematode fatty acid desaturase proteins and nucleic acids described herein are novel targets for anti-nematode vaccines, pesticides, and drugs. Inhibition of these molecules can provide means of inhibiting nematode metabolism, growth, viability, fecundity, development, infectivity and/or the nematode life-cycle.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 depicts the cDNA sequence of a *M. incognita* fatty acid desaturase (SEQ ID NO: 1), its corresponding encoded amino acid sequence (SEQ ID NO: 8).

FIG. 2 depicts the cDNA sequence of a second *M. incognita* fatty acid desaturase (SEQ ID NO: 2), its corresponding encoded amino acid sequence (SEQ ID NO: 9).

FIG. 3 depicts the cDNA sequence of a third *M. incognita* fatty acid desaturase (SEQ ID NO: 3), its corresponding encoded amino acid sequence (SEQ ID NO: 10).

FIG. 4 depicts the cDNA sequence of a *H. glycines* fatty acid desaturase (SEQ ID NO: 4), its corresponding encoded amino acid sequence (SEQ ID NO: 11).

FIG. 5 depicts the partial cDNA sequence of a *D. immitis* fatty acid desaturase (SEQ ID NO: 5), its corresponding encoded amino acid sequence (SEQ ID NO: 12).

FIG. 6 depicts the cDNA sequence of a *S. stercoralis* fatty acid desaturase (SEQ ID NO: 6), its corresponding encoded amino acid sequence (SEQ ID NO: 13).

FIG. 7 depicts the cDNA sequence of a *R. axei* fatty acid desaturase (SEQ ID NO: 7), its corresponding encoded amino acid sequence (SEQ ID NO: 14).

FIG. 8 depicts an alignment of the sequences of *M. incognita, H. glycines, D. immitis, S. stercoralis* and *R. axei* fatty acid desaturase-like polypeptides (SEQ ID NO: 8, 9, 10, 11, 12, 13 and 14) and a *C. elegans* Δ12 fatty acid desaturase polypeptide (SEQ ID NO: 32 (lower sequence)).

DETAILED DESCRIPTION

Figure 9:
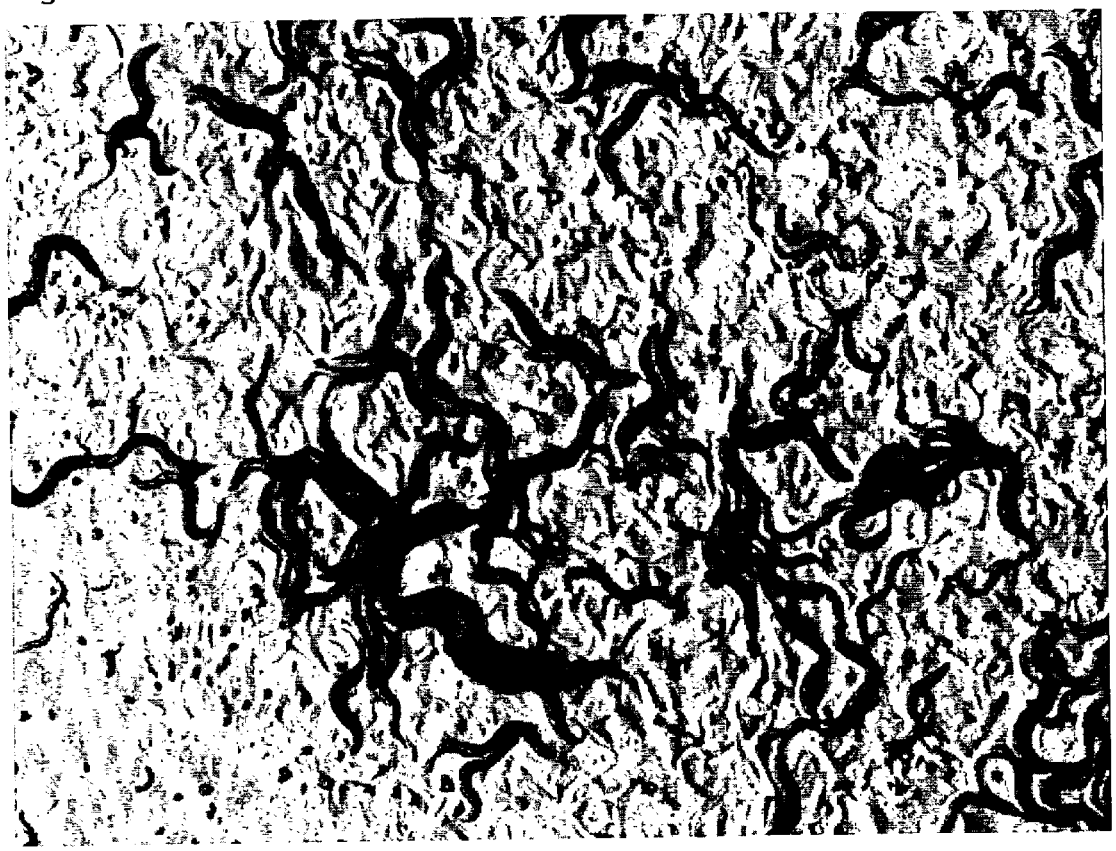
FIG. 9 is a photograph of *C. elegans* grown on oleic acid.

Described below is the identification of *M. incognita, H. glycines, D. immitis, S. stercoralis* and *R. axei* fatty acid desaturase cDNAs (SEQ ID NO: 1, 2, 3, 4, 5, 6 and 7) and the polypeptides they encode (SEQ ID NO: 8, 9, 10, 11, 12, 13 and 14). The fatty acid desaturases are Δ12 fatty acid desaturases. Also described below are experiments demonstrating that the fatty acid desaturase is essential for nematode viability. Also described below are inhibitors of the fatty acid desaturase. Certain sequence information for the fatty acid desaturase genes described herein is summarized in Table 1, below.

TABLE 1 cDNAs Identified

| Species | cDNA | Polypeptide | Figure |
|---|---|---|---|
| *M. incognita* | SEQ ID NO: 1 | SEQ ID NO: 8 | FIG. 1 |
| *M. incognita* | SEQ ID NO: 2 | SEQ ID NO: 9 | FIG. 2 |
| *M. incognita* | SEQ ID NO: 3 | SEQ ID NO: 10 | FIG. 3 |
| *H. glycines* | SEQ ID NO: 4 | SEQ ID NO: 11 | FIG. 4 |
| *D. immitis* | SEQ ID NO: 5 | SEQ ID NO: 12 | FIG. 5 |
| *S. stercoralis* | SEQ ID NO: 6 | SEQ ID NO: 13 | FIG. 6 |
| *R. axei* | SEQ ID NO: 7 | SEQ ID NO: 14 | FIG. 7 |

Unsaturated fatty acids are essential to the proper functioning of biological membranes. At physiological temperatures, polar glycerolipids that contain only saturated fatty acids cannot form the liquid-crystalline bilayer that is the fundamental structure of biological membranes. The introduction of an appropriate number of double bonds (a process referred to as desaturation) into the fatty acids of membrane glycerolipids decreases the temperature of the transition from the gel to the liquid-crystalline phase and provides membranes with necessary fluidity. Fluidity of the membrane is important for maintaining the barrier properties of the lipid bilayer and for the activation and function of certain membrane bound enzymes. There is also evidence that unsaturation confers some protection to ethanol and oxidative stress, suggesting that the degree of unsaturation of membrane fatty acids has importance beyond temperature adaptation. Unsaturated fatty acids are also precursors of polyunsaturated acids (PUFAs) arachidonic and eicosapentaenoic acids in animals, which are important sources of prostaglandins. These molecules are local hormones that alter the activities of the cells in which they are synthesized and in adjoining cells, mediating processes in reproduction, immunity, neurophysiology, thermobiology, and ion and fluid transport.

The ability of cells to modulate the degree of unsaturation in their membranes is primarily determined by the action of fatty acid desaturases. Desaturase enzymes introduce unsaturated bonds at specific positions in their fatty acyl chain substrates, using molecular oxygen and reducing equivalents from NADH (or NADPH) to catalyze the insertion of double bonds. In many systems, the reaction uses a short electron transport chain consisting of NAD(P)H, cytochrome b5 reductase, and cytochrome b5, to shuttle electrons from NAD(P)H and the carbon-carbon single bond to oxygen, forming water and a double bond (C═C). Many eukaryotic desaturases are endoplasmic reticulum (ER) bound non-heme diiron-oxo proteins which contain three conserved histidine-rich motifs and two long stretches of hydrophobic residues. These hydrophobic alpha helical domains are thought to position the protein with its bulk exposed to the cytosolic face of the ER and to organize the active site histidines to appropriately coordinate the active diiron-oxo moiety.

While most eukaryotic organisms, including mammals, can introduce a double bond into an 18-carbon fatty acid at the Δ9 position, mammals are incapable of inserting double bonds at the Δ12 or Δ15 positions. For this reason, linoleate (18:2 Δ9,12) and linolenate (18:3 Δ9,12,15) must be obtained from the diet and, thus, are termed essential fatty acids. These dietary fatty acids come predominately from plant sources, since flowering plants readily desaturate the Δ12 and the Δ15 positions. Certain animals, including some insects and nematodes, can synthesize de novo all their component fatty acids including linoleate and linolenate (Watts and Browse (2002) *Proc Natl Acad Sci USA*, 99(9):5854–9; Borgeson et al. (1990) *Biochim Biophys Acta.* 1047(2):135–40; Cripps et al. (1990) *Arch Biochem Biophys.* 278(1):46–51). The nematode *C. elegans*, for example, can synthesize de novo a broad range of polyunsaturated fatty acids including arachidonic acid and eicosapentaenoic acids, a feature not shared by either mammals or flowering plants (Tanaka et al. (1999) *Eur J. Biochem.* 263(1):189–95).

The *C. elegans* desaturase gene fat-2 has been expressed in *S. cerevisiae* and shown to be a Δ12 fatty acid desaturase. This enzyme introduces a double bond between the 12$^{th}$ and the 13$^{th}$ carbons (from the carboxylate end) and can convert the mono-unsaturated oleate (18:1 Δ9) and palmitoleate (16:1Δ9) to the di-unsaturated linoleate (18:2Δ9,12) and 16:2 Δ9,12 fatty acids, respectively.

The nematode Δ12 enzymes are potentially good targets for anti-nematode compounds for several reasons. Firstly, the enzymes appear to be phylogenetically diverged from their homologs in plants, having less than 40% pairwise sequence identity at the amino acid level and phylogenetic analyses demonstrate clustering of nematode Δ12 and ω-3 desaturases away from homologs in plants. Experiments with both transgenic *Arabidopsis* and soybeans reveal that plants can tolerate significant reductions in Δ12 fatty acid desaturase activity, suggesting that inhibitors of desaturases would likely not be toxic to plants (Singh et al. (2000) *Biochem. Society Trans.* 28: 940–942; Lee et al. (1998) *Science* 280:915–918). In addition, as mentioned above, mammals are thought not to have Δ12 fatty acid desaturases. Thus, inhibitors of the enzyme are likely to be non-toxic to mammals. Importantly, as detailed herein, a fatty acid desaturase of nematodes has been shown to be essential to their viability, both through inhibitor and RNA-mediated interference studies. Thus, Δ12 fatty acid desaturases could serve as ideal targets for anti-nematode control, as inhibitors of the enzyme could specifically target nematodes while leaving their animal and plant hosts unharmed.

Numerous analogs of fatty acids exist and some may act as specific inhibitors of enzymes such as desaturases that act on fatty acids, a fact that could be exploited for development of anti-nematode compounds. Sterculic acid, a cyclopropenoid fatty acid analog of oleic acid, is a potent inhibitor of Δ9 fatty acid desaturases (Schmid & Patterson (1998) *Lipids* 23(3):248–52; Waltermann & Steinbuchel (2000) *FEMS Microbiol Lett.* 190(1):45–50). It has also been speculated that cyclopropenoid analogs of linoleic acid may similarly inhibit Δ12 fatty acid desaturases (Dulayymi et al. (1997) *Tetrahedron* 53(3):1099–1110). It is worth noting however that malvalate, a Δ8 cyclopropene fatty acid, seems to be equally inhibitory to Δ9 desaturases in some systems, (Schmid & Patterson (1998) *Lipids* 23(3):248–52), demonstrating how difficult it is to predict inhibitory profiles for some fatty acid analogs. Thia fatty acid analogs (i.e., sulfur containing fatty acids) are also potential inhibitors of fatty acid desaturases (Skrede et al. (1997) *Biochim Biophys Acta* 1344(2):115–131; Hovik et al. (1997) *Biochim Biophys Acta* 1349(3):251–256) as are tran fatty acids (Choi et al. (2001) *Biochem Biophys Res Commun* 284(3):689–93). However, the specificity and pesticidal activity of these analogs is again difficult to predict (Beach et al. (1989) *Mol Biochem Parasitol* 35(1):57–66).

Certain fatty acids are also specific receptor antagonists (Yagaloff (1995) *Prostaglandins Leukot Essent Fatty Acids* 52(5):293–7).

Other analogs of linoleic acid that may also be specific Δ12 inhibitors include the epoxy fatty acid (vernolic acid), the acetylenic fatty acid (crepenynic acid), 12-oxo-9(Z)-octadecenoic acid methyl ester or the hydroxy fatty acids (ricinoleic and ricinelaidic acid). Inhibitors that interfere with Δ12 fatty acid desaturase activity are expected to be toxic to nematodes. Importantly, fatty acid analogs such as ricinoleic, ricinelaidic, vernolic and crepenynic acid methyl esters do not appear to be toxic (or are very much less toxic) to at least some plants and are predicted not to be toxic (or are very much less toxic) to at least some animals, including mammals. Such fatty acid analogs could potentially be used in the development of nematode control agents.

Although previously expressed in plants, fatty acid analogs such as crepenynate, ricinoleate and vernolate acids were not thought to be specific inhibitors of the endogenous plant Δ12 desaturase (Broun & Somerville (1997) *Plant. Physiol.* 113:933–942; Singh et al. (2000) *Biochem. Society Trans.* 28(6): 940–942). Changes in the ratio of oleate to linoleate in plants expressing the genes for these analogs was instead attributed to a negative interaction between the enzymes involved (Singh et al. (2001) *Planta* 212: 872–879). Addition of ricinoleate exogenously to *Neurospora crassa* results in a significant decrease in oleate (C18:1) and an increase in linolenate (C18:3) again providing no indication that compounds like ricinoleate were in fact specific Δ12 desaturase inhibitors (Goodrich-Tanrikulu et al. (1996) *Appl Microbiol Biotechnol.* 46(4):382–7).

We made the surprising discovery that methyl esters of certain fatty acid analogs (e.g., ricinoleate, vernolate) are nematicidal and have activity consistent with that of specific inhibitors of nematode Δ12 desaturases. The fatty acid methyl esters show significantly enhanced activity over other eighteen carbon fatty acid esters such as oleate, elaidate and linoleate. In contrast to short chain seemingly non-specific pesticidal fatty acid esters such as laurate and pelargonate, the fatty acid analogs that are predicted Δ12 desaturase inhibitors show dramatically reduced phytoxicity and can therefore be used effectively while minimizing undesirable damage to non-target organisms.

Fatty acid-based analogs or other types of inhibitors may be supplied to plants exogenously, through sprays for example. It is also possible to provide inhibitors through a host organism or an organism on which the nematode feeds. For example, a host cell that does not naturally produce an inhibitor of the *M. incognita, H. glycines, D. immitis* and *S. stercoralis* fatty acid desaturase-like polypeptides can be transformed with enzymes capable of making inhibitory analogs and provided with appropriate precursor chemicals exogenously. Alternatively, the active inhibitors and precursors can be made endogenously by the expression of the appropriate enzymes. In addition, yeast or other organisms can be modified to produce inhibitors. Nematodes that feed on such organisms would then be exposed to the inhibitors.

In one embodiment, transgenic cells and/or organisms could be generated that produce enzymes active on fatty acids (e.g., desaturating, hydroxylating, conjugating, and/or epoxygenating enzymes). Such enzymes may be expressed, for example, in plants, vertebrates, and/or nematodes. These enzymes may produce fatty acids, analogs, or other inhibitors that can then act as specific inhibitors for other enzymes such as a fatty acid desaturase (e.g., a Δ12 epoxygenase from *Crepis palaestina* produces vernolic acid, a Δ12 desaturase inhibitor, in transgenic *Arabidopsis*) (Singh et. al. (2000) *Biochem. Society Trans.* 28:940–942; Lee et al. (1998) *Science* 280:915–918).

More generally, a recombinant expression vector capable of expressing an enzyme active on fatty acids could be transformed into a host cell of an organism that is parasitized by a parasitic nematode, (*M. incognita, H. glycines, D. immitis* or *S. stercoralis*, for example). Fatty acid analogs that act as inhibitors of *M. incognita, H. glycines, D. immitis* or *S. stercoralis* Δ12 fatty acid desaturases, for example, can then be produced in the host cell or organism. In this manner, Δ12 fatty acid desaturases from feeding parasitic nematodes (e.g., *M. incognita, H. glycines, D. immitis* or *S. stercoralis*) could be rendered inactive by the fatty acid analog.

In another embodiment, a recombinant expression vector harboring a Δ12 fatty acid desaturase-like polypeptide from, for example, *M. incognita, H. glycines, D. immitis, S. stercoralis* or *R. axei*, can be used to produce a recombinant fatty acid desaturase polypeptide that is functional in a cell, plant or animal, and that can desaturate fatty acids that are normally produced by the cell, plant or animal or that are provided exogenously to the cell, plant or animal to the corresponding Δ12 fatty acid. In this way, a cell, plant or animal can be produced that has a higher proportion of Δ12 unsaturated fatty acids than an otherwise similar cell, plant, or animal lacking the recombinant fatty acid desaturase polypeptide. In this way, a cell, plant or animal that has increased resistance to a Δ12 fatty acid desaturase inhibitor can be produced.

A recombinant Δ12 fatty acid desaturase, e.g., a *M. incognita, H. glycines, D. immitis, S. stercoralis* or *R. axei* fatty acid desaturase, may also be useful for producing lipids having a higher proportion of Δ12 unsaturated fatty acids, whether by means of recombinant expression in a cell or in an industrial process using purified nematode Δ12 fatty acid desaturase polypeptide. Such lipids are useful as food oils, as nutritional supplements, and as chemical feedstocks, for example.

The following examples are therefore to be construed as merely illustrative, and not limitative of the remainder of the disclosure in any way whatsoever. All of the publications cited herein are hereby incorporated by reference in their entirety.

EXAMPLES

TBLASTN searches of a database of nematode EST sequences (McCarter et al. (1999) Washington University Nematode EST Project) with *C. elegans* Δ12 fatty acid desaturase (FAT-2) gene sequence (GenBank® Accession No: AAF63745: ID No: 7546993) identified two EST's (AW783527 and AW871151) that are predicted to encode at least a portion of a Δ12 Fatty Acid Desaturase-like enzymes (Δ12 FAT) in one nematode species, *M. incognita*.

Full Length Δ12 Fatty Acid Desaturase-Like cDNA Sequences

The plasmid clone corresponding to the *M. incognita* EST sequence AW783527 was obtained from the Genome Sequencing Center (St. Louis, Mo.). This plasmid clone was designated Div249. The cDNA insert in the plasmid was sequenced in its entirety. Unless otherwise indicated, all nucleotide sequences determined herein were sequenced with an automated DNA sequencer (such as model 373 from Applied Biosystems, Inc.) using processes well known to those skilled in the art. Primers used for sequencing are listed in Table 1 (see below). Partial sequence data for the *M. incognita* Δ12 FAT was obtained from Div249, including nucleotide sequence for codons 90–397 and additional 3' untranslated sequence. The clone lacked the first 89 codons of the *M. incognita* Δ12 FAT, as well as the 5' untranslated region.

The following methods were used to obtain the full-length nematode Δ12 FAT gene and to determine its complete sequence. First, RNA was obtained from plant parasitic nematodes, which are maintained on greenhouse pot cultures depending on nematode preference. Root Knot Nematodes (*Meloidogyne* sp) were propagated on Rutgers tomato (Burpee). Total RNA was isolated using the TRIZOL reagent (Gibco BRL). Briefly, 2 ml of packed worms were combined with 8 ml TRIZOL reagent and solubilized by vortexing. Following 5 minutes of incubation at room temperature, the samples are divided into smaller volumes and spun at 14,000×g for 10 minutes at 4° C. to remove insoluble material. The liquid phase was extracted with 200 μl of chloroform, and the upper aqueous phase was removed to a fresh tube. The RNA was precipitated by the addition of 500 μl of isopropanol and centrifuged to pellet. The aqueous phase was carefully removed, and the pellet was washed in 75% ethanol and spun to re-collect the RNA pellet. The supernatant was carefully removed, and the pellet was air dried for 10 minutes. The RNA pellet was resuspended in 50 μl of DEPC-H$_2$O and analyzed by spectrophotometry at 260 and 280 nm to determine yield and purity. Yields could be 1–4 mg of total RNA from 2 ml of packed worms.

To obtain the missing 5' sequence of the *M. incognita* Δ12 FAT gene, the 5' RACE technique was applied, and SL1 PCR was performed using first strand cDNA from *M. incognita* as a template. Briefly, SL1 PCR utilizes the observation, that unlike most eukaryotic mRNAs, many nematode mRNA molecules contain a common leader sequence (5' ggg ttt aat tac cca agt ttg a 3'; SEQ ID NO: 17) transpliced to their 5' ends. If this sequence is present on the 5' end of a cDNA, that cDNA can be amplified using PCR with a primer that binds to the SL1 transpliced leader and a gene-specific primer near the 3' end of the cDNA.

Briefly, following the instructions provided by Life Technologies cDNA synthesis kit, first strand cDNA synthesis was performed on total nematode RNA using SuperScript™ II Reverse Transcriptase and an oligo-dT primer (which anneals to the natural poly A tail found on the 3' end of all eukaryotic mRNA). RNase H was then used to degrade the original mRNA template. Following degradation of the original mRNA template, the first strand cDNA was directly PCR amplified without further purification using Taq DNA polymerase, a gene specific primer (FAT10, SEQ ID NO: 19) designed from known sequence that anneals to a site located within the first strand cDNA molecule, and the SL1 primer, which is homologous the 5' end of the cDNA of interest. Amplified PCR products were then cloned into a suitable vector for DNA sequence analysis. This procedure was performed to obtain clone Div864. This clone contained codons 1–120 in addition to 5' untranslated sequences. Taken together, clones Div249 and Div864 contain sequences comprising the complete open reading frame of the Δ12 FAT gene from *M. incognita*.

To obtain the complete Δ12 fatty acid desaturase gene from *M. incognita* on one clone, primers FAT30 and FAT31 were designed to amplify the complete open reading frame. Following PCR amplification, several independent clones were obtained. DNA sequence analysis revealed that two very similar but distinct fatty acid desaturase genes had been identified. Along with the gene sequence reported for SEQ ID NO: 1 (1191 nucleotide ORF, 397 amino acid polypeptide, FIG. 1), we also identified SEQ ID NO: 2 (1239 nucleotide ORF, 413 amino acid polypeptide, FIG. 2). The two genes are very similar and are identical in the regions homologous to primers FAT30 and FAT31. Clones containing sequences identical to SEQ ID NO: 1 included Div1456 and Div1459. Clones containing sequences identical to SEQ ID NO: 2 included Div1458 and Div1463. While cloning the first two *M. incognita* Δ12 fatty acid desaturase genes, a third Δ12 fatty acid desaturase gene fragment from *M. incognita* was obtained by PCR amplification using the FAT10/SL1 primer combination, resulting in clone Div866. This clone contains codons 1–108 of the third *M. incognita* Δ12 fatty acid desaturase gene. In order to obtain the complete gene sequence, a gene-specific primer (FAT23, SEQ ID NO: 23) designed to a known sequence that anneals to a site located within the first strand cDNA molecule, and an oligo dT primer, which is homologous to the 3' end of the cDNA of interest were used. Amplified PCR products were then cloned into a suitable vector for DNA sequence analysis. This procedure was performed to obtain clone Div2727. This clone contains codons 96–387 in addition to 3' untranslated sequences. Taken together, clones Div866 and Div2727 contain sequences comprising the complete open reading of the third Δ12 fatty acid desaturase gene from *M. incognita*. The gene sequence reported for SEQ ID NO: 3 (1161 nucleotide ORF, 387 amino acid polypeptide, FIG. 3) is very similar to the first two *M. incognita* Δ12 fatty acid desaturase genes. The first two predicted Δ12 fatty acid desaturase polypeptides (SEQ ID NO: 8 and 9) are approximately 92% identical to each other and approximately 57% and 56% identical to the *C. elegans* fatty acid desaturase (SEQ ID NO: 32), respectively, and are approximately 69% and 70% identical to the third *M. incognita* predicted Δ12 fatty acid desaturase polypeptide (SEQ ID NO: 10), respectively. The third predicted Δ12 FAT polypeptide (SEQ ID NO: 10) is approximately 51% identical to the *C. elegans* Δ12 fatty acid desaturase (SEQ ID NO: 32) and 69% similar.

In order to obtain the *H. glycines* Δ12 fatty acid desaturase gene, the 5' RACE technique was applied, and SL1 PCR was performed using first strand cDNA from *H. glycines* as a template (cDNA synthesis explained above). The first strand cDNA was directly PCR amplified using the SL1 primer and a gene specific degenerate primer (FAT33, SEQ ID NO: 24) designed to anneal to region of strong homology shared across many nematode desaturase genes. Amplified PCR products were then cloned into a suitable vector for DNA sequence analysis. This procedure was performed to obtain clone Div1870. This clone contained codons 1–193 in addition to 5' untranslated sequences. To obtain the 3' sequence of the gene, the 3' RACE technique was applied. The first strand cDNA was directly PCR amplified using a gene specific primer (FAT44, SEQ ID NO: 25) designed from known sequence that anneals within the first strand cDNA molecule of interest, and an oligo dT primer, which is homologous to the 3' end of the cDNA of interest. This procedure was performed to generate clone Div2724, which contains codons 144–389 in addition to 3' untranslated sequences. Taken together, clones Div1870 and Div2724 contain sequences comprising the complete open reading frame of the Δ12 fatty acid desaturase gene of *H. glycines*. The predicted Δ12 fatty acid desaturase polypeptide reported for SEQ ID NO: 11, (1167 nucleotide ORF, 389 amino acid polypeptide, FIG. 4) is approximately 56% identical and 73% similar to the *C. elegans* fatty acid desaturase (SEQ ID NO: 32).

In an attempt to obtain the *D. immitis* Δ12 fatty acid desaturase gene, first strand cDNA, using *D. immitis* cDNA as a template (cDNA synthesis described above), was directly PCR amplified, using a gene-specific degenerate primer (FAT35, SEQ ID NO: 26) designed to anneal to a region of strong homology shared across many nematode desaturase genes, and another gene-specific degenerate primer (FT05, SEQ ID NO: 27), which was predicted to be homologous to a region near the 5' end of the cDNA of interest. Amplified PCR products were then cloned into a suitable vector for DNA sequence analysis. This procedure was performed to obtain clone Div3228, which contains codons 1–224, which correspond to codons 78–301 of the *C. elegans* fatty acid desaturase (SEQ ID NO: 32). To acquire the missing 3' sequence of *D. immitis* Δ12 fatty acid desaturase, the 3' RACE technique was applied using a gene-specific primer (FAT12, SEQ ID NO: 28) designed to a known sequence that anneals to a site located within the first strand cDNA molecule, and an oligo dT primer, which is homologous to the 3' end of the cDNA of interest. Amplified PCR products were then cloned into a suitable DNA vector for sequence analysis. This procedure was performed to obtain the clone Div3230, which contained the codons 196–289, which correspond to codons 273–376 of the *C. elegans* fatty acid desaturase (SEQ ID NO: 32), in addition to 3' untranslated sequences. Taken together, clones Div3228 and Div3230 comprise approximately 80% of the complete *D. immitis* Δ12 FAT open reading frame. The 5' end sequence of this gene has yet to be completed. The partial Δ12 fatty acid desaturase polypeptide sequence reported for SEQ ID NO: 12 (867 nucleotide ORF, 289 amino acid polypeptide, FIG. 5) is 62% identical and 75% similar to the *C. elegans* fatty acid desaturase (SEQ ID NO: 32).

Plasmid clone, Div3013, corresponding to the *S. stercoralis* EST sequence (GenBank® Identification No: 9830288) was obtained from the Genome Sequencing Center (St. Louis, Mo.). The cDNA insert in the plasmid was sequenced in its entirety. Full sequence data for the *S. stercoralis* Δ12 fatty acid desaturase was obtained from Div3013, including nucleotide sequence for codons 1–368, (the full open reading frame) and additional 5' and 3' untranslated sequences. The predicted gene sequence reported for SEQ ID NO: 6 (1104 nucleotide ORF, 368 amino acid polypeptide, FIG. 6) is approximately 61% identical and 76% similar to the *C. elegans* fatty acid desaturase (SEQ ID NO: 32).

In order to obtain the sequence of the *R. axei* Δ12 fatty acid desaturase gene, first strand cDNA from *R. axei* was directly PCR amplified, using a gene-specific degenerate primer (FAT35, SEQ ID NO: 26) designed to anneal to region of strong homology shared across many nematode desaturase genes, and another gene-specific degenerate primer (FAT34, SEQ ID NO: 29) designed to anneal to region of strong homology shared across many nematode desaturase genes near the 3' end of the cDNA of interest. Amplified PCR products were then cloned into a suitable DNA vector for sequence analysis. This procedure was performed to obtain the clone Div1843, which contained the codons 185–301 (an internal fragment missing both the 5' and 3' ends of the gene). In order to obtain the missing 5' sequence of the *R. axei* Δ12 fatty acid desaturase gene, the 5' RACE technique was applied and SL1 PCR was performed using first strand cDNA from *R. axei* as a template (cDNA synthesis described above). The first strand cDNA was directly PCR amplified using a gene specific primer (FAT40, SEQ. ID. NO. 30) designed from the known sequence of clone Div1843, that anneals to a site located within the cDNA of interest, and the SL1 primer, which is homologous to the 5' end of many nematode cDNAs. Amplified PCR products were then cloned into a suitable vector for DNA sequence analysis. This procedure was performed to obtain the clone Div2026, which contained the codons 1–199, in addition to 5' untranslated sequences. To obtain the missing 3' sequence of the gene, the 3' RACE technique was applied using a gene specific primer (FAT42, SEQ ID NO: 31) designed from the known sequence of clone Div1843, that anneals to a site located within the cDNA of interest, and an oligo dT primer, which is homologous to the 3' end of the cDNA of interest. Amplified PCR products were then cloned into a suitable vector for DNA sequence analysis. This procedure was performed to obtain clone Div2149. This clone contained codons 246–374 in addition to 3' untranslated sequences. Taken together, clones Div1843, Div2149, and Div2026 contain sequences comprising the complete open reading frame of the Δ12 FAT gene from *R. axei*. The predicted Δ12 fatty acid desaturase polypeptide gene sequence reported for SEQ ID NO: 7, (1122 nucleotide ORF, 374 amino acid polypeptide, FIG. 7) is approximately 71% identical and 82% similar to *C. elegans* fatty acid desaturase (SEQ ID NO: 32).

TABLE 2

Primers Employed in Cloning

| Name | Sequence | SEQ ID NO: | Homology to |
|---|---|---|---|
| T7 | Gtaatacgactcactatagggc | 15 | vector polylinker primer |
| T3 | Aattaaccctcactaaaggg | 16 | vector polylinker primer |
| SL1 | Gggtttaattacccaagtttga | 17 | nematode transpliced leader |
| Oligo dT | gagagagagagagagagagaactagtctcgagtttttttttttttttttt | 18 | universal primer to poly A tail |
| FAT10 | 5' aag ttc cgt gcc cac aat c 3' | 19 | Mi Δ12 FAT (codons 115–120)* |
| FAT11 | 5' gcc aaa aat gag aac cat cg 3' | 20 | Mi Δ12 FAT (codons 206–211)* |
| FAT30 | 5' atg tct tat ctt gac aca ac 3' | 21 | Mi Δ12 FAT (codons 1–6)* |
| FAT31 | 5' cta ttt atc ctt ttt att at 3' | 22 | Mi Δ12 FAT (codons 392–397)* |
| FAT23 | tctatattcgctgttggacacg | 23 | Mi Δ12 FAT (codons 96–102) |
| FAT33 | gtrtadatnggrttcca | 24 | Ce Δ12 FAT (codons 174–179) |
| FAT44 | ctggtactgcttgctcggca | 25 | Hg Δ12 FAT (codons 92–97) |
| FAT35 | aaraaraartgrtgngcnacrtg | 26 | Ce Δ12 FAT (codons 295–301)# |
| FT05 | atgggnatgttyggntc | 27 | Ce Δ12 FAT (codons 81–85)# |
| FT12 | gtacaaaccattgatcgag | 28 | Di Δ12 FAT (codons 196–201) |
| FAT34 | gayggntctcayttytggccntgg | 29 | Ce Δ12 FAT (codons 185–192)# |
| FAT40 | ctctatcttcagtcgttgtg | 30 | Ra Δ12 FAT (codons 179–202) |
| FAT42 | ggttatcatcacctatctgc | 31 | Ra Δ12 FAT (codons 246–251) |

*codon numbering is based on SEQ ID NO:1.
codon numbering is based on SEQ ID NO:32

Characterization of M. incognita, H. glycines, D. immitis, S. stercoralis and R. axei Δ12 Fatty Acid Desaturase Genes.

The similarity between the Δ12 fatty acid desaturase proteins from M. incognita, H. glycines, D. immitis, S. stercoralis and R. axei from C. elegans is presented as a multiple alignment generated by the ClustalX multiple alignment program as described below (FIG. 8).

The similarity between M. incognita, H. glycines, D. immitis, S. stercoralis and R. axei Δ12 fatty acid desaturase-like sequences and other sequences was also investigated by comparison to sequence databases using BLASTP analysis against nr (a non-redundant protein sequence database available on the Internet at www.ncbi.nlm.nih.gov) and TBLASTN analysis against dbest (an EST sequence database available on the Internet at www.ncbi.nlm.nih.gov; top 500 hits; E=1e-4). The "Expect (E) value" is the number of sequences that are predicted to align by chance to the query sequence with a score S or greater given the size of the database queried. This analysis was used to determine the potential number of plant and vertebrate homologs for each of the nematode fatty acid desaturase-like polypeptides described above. While M. incognita (SEQ ID NO:1, 2 and SEQ ID NO:3), H. glycines (SEQ ID NO:4), D. immitis (SEQ ID NO:5), S. stercoralis (SEQ ID NO:6) and R. axei (SEQ ID NO:7) fatty acid desaturase-like cDNA sequences had numerous plant hits, they had no vertebrate hits in nr or dbest having sufficient sequence similarity to meet the threshold E value of 1e-4 (this E value approximately corresponds to a threshold for removing sequences having a sequence identity of less than about 25% over approximately 100 amino acids). Accordingly, the M. incognita, H. glycines, D. immitis, S. stercoralis and R. axei fatty acid desaturase-like enzymes of this invention do not appear to share significant sequence similarity with the more common vertebrate fatty acid desaturase enzymes such as the Δ6 fatty acid desaturase of Homo sapiens (a member of the FAD family of desaturases, GenBank Accession No. NP_068373), the Δ5 fatty acid desaturase of Homo sapiens (also a member of the FAD family, GenBank Accession No. NP_037534) or other mammalian fatty acid desaturases.

On the basis of the lack of similarity to vertebrates, the D. immitis and S. stercoralis fatty acid desaturase-like enzymes (e.g., Δ12 fatty acid desaturase) are useful targets of inhibitory compounds selective for some nematodes over their hosts (e.g., humans, animals). While at least some plants have fatty acid desaturases that are somewhat homologous to those in parasitic nematodes, including M. incognita and H. glycines, other criteria make them promising targets for the control of plant parasitic nematodes, including the fact that at least in some cases, plants can tolerate significant reductions in fatty acid desaturase activity while, as demonstrated below, nematodes can not.

Functional predictions were made using four iterations of PSI-BLAST with the default parameters on the nr database. PSI-BLAST searches and multiple alignment construction with CLUSTALX demonstrated that the C. elegans gene (GenBank® Accession No: AAF63745) was a member of the fatty acid desaturase family. Reciprocal blast searches and phylogenetic trees confirm that the nucleotide sequences in M. incognita, H. glycines, D. immitis, S. stercoralis and R. axei do encode orthologs of the C. elegans gene and therefore are also likely fatty acid desaturase proteins with the same activity. Protein localizations were predicted using the TargetP server available on the Internet at: www.cbs.dtu.dk/services/TargetP. The M. incognita fatty acid desaturase (SEQ ID NO: 8, 9 and SEQ ID NO:10), H. glycines (SEQ ID NO: 11), D. immitis (SEQ ID NO:12), S. stercoralis (SEQ ID NO:13) and R. axei (SEQ ID NO:14) polypeptides are likely to be cytoplasmic. In addition, they are predicted to have four transmembrane regions, consistent with the model that they are membrane bound.

RNA Mediated Interference (RNAi)

A double stranded RNA (dsRNA) molecule can be used to inactivate a Δ12 fatty acid desaturase (Δ12 FAT) gene in a cell by a process known as RNA mediated-interference (Fire et al. (1998) Nature 391:806–811, and Gönczy et al. (2000) Nature 408:331–336). The dsRNA molecule can have the nucleotide sequence of a Δ12 FAT nucleic acid described herein or a fragment thereof. The dsRNA molecule can be delivered to nematodes via direct injection, or by soaking nematodes in aqueous solution containing concentrated dsRNA, or by raising bacteriovorous nematodes on E. coli genetically engineered to produce the dsRNA molecule.

RNAi by injection: To examine the effect of inhibiting Δ12 FAT activity, a Δ12 dsRNA was injected into the nematode, basically as described in Mello et al. (1991) *EMBO J.* 10:3959–3970. Briefly, a plasmid was constructed that contains a portion of the *C. elegans* Δ12 FAT gene sequence, specifically a fragment 651 nucleotides long, containing the entire first exon and terminating just before the conserved intron splice junction between the first exon and first intron. This construct encodes approximately the first 217 amino acids of the *C. elegans* Δ12 FAT gene. Primers were used to specifically amplify this sequence as a linear dsDNA. Single-stranded RNAs were transcribed from these fragments using T7 RNA polymerase and SP6 RNA polymerase (the RNAs correspond to the sense and antisense RNA strands). RNA was precipitated and resuspended in RNAse free water. For annealing of ssRNAs to form dsRNAs, ssRNAs were combined, heated to 95° for two minutes then allowed to cool from 70° to room temperature over 1.5–2.5 hours.

DsRNA was injected into the body cavity of 15–20 young adult *C. elegans* hermaphrodites. Worms were typically immobilized on an agarose pad and injected with 2–5 μl of dsRNA at a concentration of 1 mg/ml. Injections were performed with visual observation using a Zeiss Axiovert compound microscope equipped with 10× and 40×DIC objectives, for example. Needles for microinjection were prepared using a Narishige needle puller, stage microman- ipulator (Leitz) and a $N_2$-powered injector (Narishige) set at 10–20 p.s.i. After injection, 200 μl of recovery buffer (0.1% salmon sperm DNA, 4% glucose, 2.4 mM KCl, 66 mM NaCl, 3 mM $CaCl_2$, 3 mM HEPES, pH 7.2) were added to the agarose pad and the worms were allowed to recover on the agarose pad for 0.5–4 hours. After recovery, the worms were transferred to NGM agar plates seeded with a lawn of *E. coli* strain OP50 as a food source. The following day and for 3 successive days thereafter, 7 individual healthy injected worms were transferred to new NGM plates seeded with OP50. The number of eggs laid per worm per day and the number of those eggs that hatch and reach fertile adulthood were determined. As a control, Green Fluorescent Protein (GFP) dsRNA was produced and injected using similar methods. GFP is a commonly used reporter gene originally isolated from jellyfish and is widely used in both prokaryotic and eukaryotic systems. The GFP gene is not present in the wild-type *C. elegans* genome and, therefore, GFP dsRNA does not trigger an RNAi phenotype in wild-type *C. elegans*. The *C. elegans* Δ12 FAT RNAi injection phenotype presented as a strongly reduced F1 hatch-rate, with the few surviving individuals arrested in an early larval stage.

RNAi by feeding: *C. elegans* can be grown on lawns of *E. coli* genetically engineered to produce double stranded RNA (dsRNA) designed to inhibit Δ12 FAT expression. Briefly, *E. coli* were transformed with a genomic fragment of a portion of the *C. elegans* Δ12 FAT gene sequence, specifically a fragment 651 nucleotides long, containing the entire first exon and terminating just before the conserved intron splice junction between the first exon and first intron. This construct encodes approximately the first 217 amino acids of the *C. elegans* Δ12 FAT gene. The 651 nucleotide genomic fragment was cloned into an *E. coli* expression vector between opposing T7 polymerase promoters. The clone was then transformed into a strain of *E. coli* that carries an IPTG-inducible T7 polymerase. As a control, *E. coli* was transformed with a gene encoding the Green Fluorescent Protein (GFP). Feeding RNAi was initiated from *C. elegans* eggs or from *C. elegans* L4s. When feeding RNAi was started from *C. elegans* eggs at 23° C. on NGM plates containing IPTG and *E. coli* expressing the *C. elegans* Δ12 FAT or GFP dsRNA, the *C. elegans* Δ12 FAT RNAi feeding phenotype presented as partially sterile F1 individuals and dead F2 embryos. When feeding RNAi was started from *C. elegans* L4 larvae at 23° C. on NGM plates containing IPTG and *E. coli* expressing the *C. elegans* Δ12 FAT or GFP dsRNA, the *C. elegans* RNAi feeding phenotype presented as partially sterile $P_0$ individuals with developmentally arrested, sterile F1 nematodes.

*C. elegans* cultures grown in the presence of *E. coli* expressing dsRNA and those injected with dsRNA from the Δ12 FAT gene were strongly impaired indicating that the fatty acid desaturase-like gene provides an essential function in nematodes and that dsRNA from the fatty acid desaturase-like gene is lethal when ingested by or injected into *C. elegans*.

Rescue of *C. elegans* Δ12 FAT RNAi Feeding Phenotype by Linoleic Acid Methyl Ester The *C. elegans* Δ12 fatty acid desaturase (Fat2 protein) converts the mono-unsaturated oleic acid to the di-unsaturated fatty acid linoleic acid. The Δ12 FAT RNAi prevents expression of the Δ12 fatty acid desaturase, which is predicted to cause a decrease in levels of linoleic acid in the nematode, leading to arrested development and death. Addition of 3 mM linoleic acid methyl ester to the NGM media used for the RNAi experiment brings about a partial rescue of the Δ12 FAT RNAi feeding phenotype. Addition of 3 mM oleic acid methyl ester does not rescue the Δ12 FAT RNAi feeding phenotype (see Table 3 below).

TABLE 3

*C. elegans* Δ12 FAT RNAi feeding phenotypes (starting with *C. elegans* L4 larvae as the $P_0$ animal)

| Fatty Acid Added | $P_0$ phenotype | F1 phenotype | F2 phenotype |
| --- | --- | --- | --- |
| None | Severely reduced egg laying (almost sterile) | Developmentally arrested and sterile | NA |
| Oleic Acid Methyl Ester | Severely reduced egg laying (almost sterile) | Developmentally arrested and sterile | NA |
| Linoleic Acid Methyl Ester | Reduced egg laying | Moderately delayed development and moderately reduced egg laying | Slightly delayed development |

Inhibitor Studies

Figure 10:
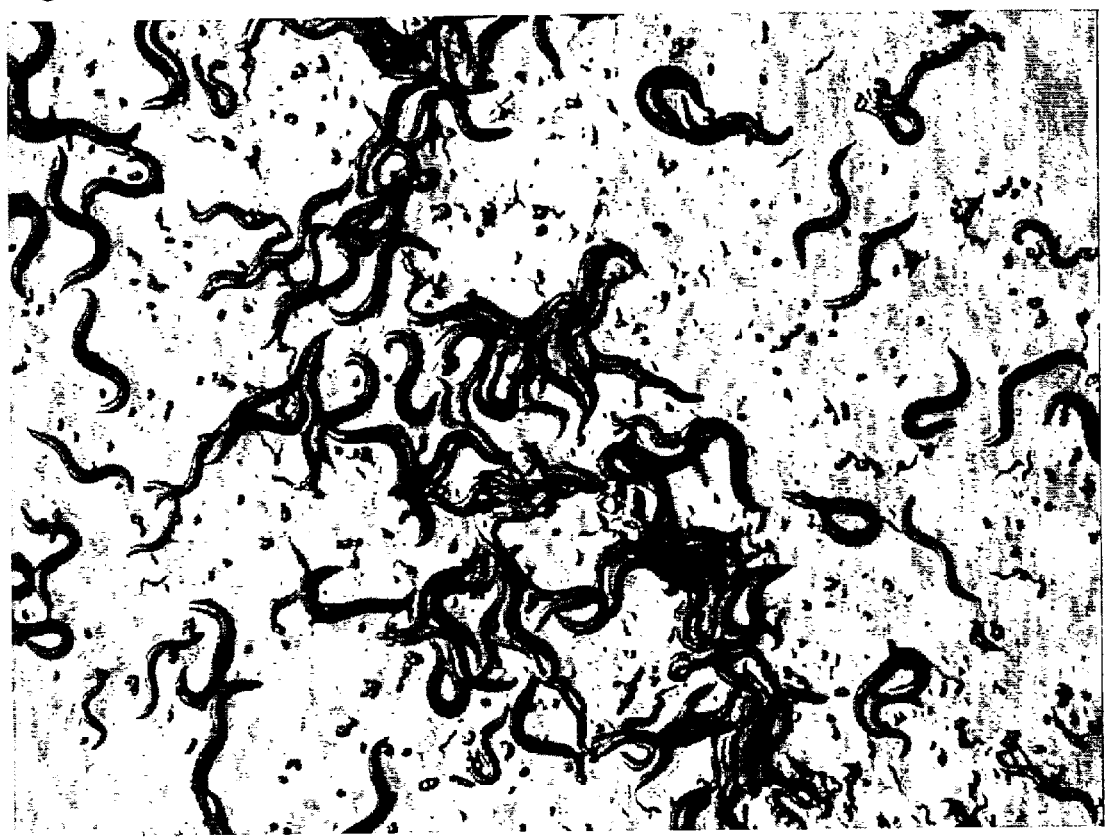
FIG. 10 is a photograph of *C. elegans* grown on linoleic acid.
Figure 11:
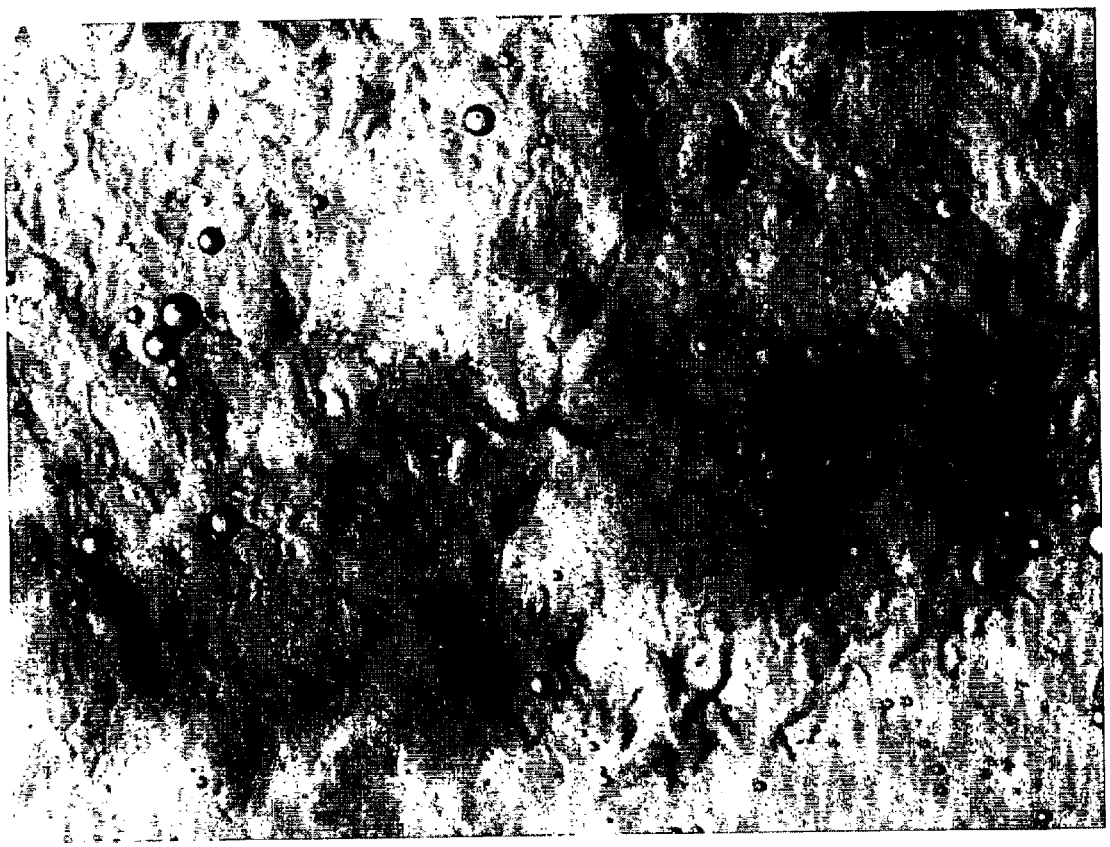
FIG. 11 is a photograph of *C. elegans* grown on ricinoleic acid.
Figure 12:
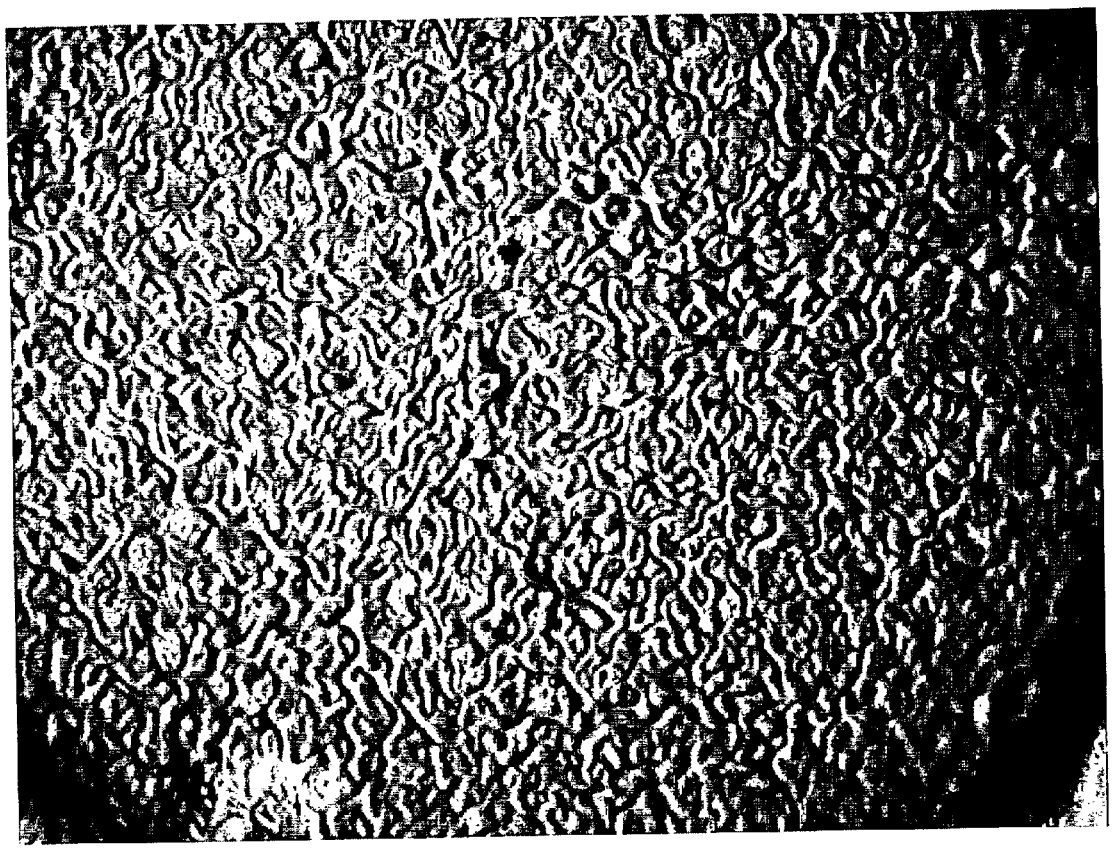
FIG. 12 is a photograph of *C. elegans* grown on vernolic acid.

Vernolic acid and ricinoleic acid are naturally occurring plant-produced fatty acid homologs that we predict to be specific inhibitors of Δ12 FAT enzymes. The addition of these compounds to living cultures of *C. elegans* is expected to mimic the effects of the Δ12 FAT RNAi experiments since, in each case, the phenotype observed should derive from the inhibition of the nematode Δ12 FAT. To explore this possibility, *C. elegans* cultures were started from eggs on NGM plates containing their *E. coli* food source and one of either 3 mM ricinoleic acid methyl ester or 3 mM vernolic acid methyl ester. Total eggs layed and hatch-rates of F1 and F2 individuals were followed and compared to nematode cultures grown in the presence of control fatty acids oleic acid methyl ester and linoleic acid methyl ester. *C. elegans* L4 larvae were added to NGM plates containing OP50 *E. coli* and one of the following methyl esters: oleic acid, linoleic acid, ricinoleic acid, vernolic acid or none. *C. elegans* L4 larvae growing on plates containing ricinoleic acid (FIG. 11) or vernolic acid (FIG. 12) methyl esters developed to mature adults more slowly than those on control plates containing oleic acid (FIG. 9) or linoleic acid (FIG. 10) and produced very few embryos (eggs). Of the embryos that hatched, the young larvae displayed severe arrested phenotypes and did not develop to adults (FIGS. 11 and 12). *C. elegans* cultures growing on plates containing no fatty acid methyl esters or oleic acid or linoleic acid methyl esters exhibited no dramatic lifecycle impairments (FIGS. 9 and 10).

Identification of Additional Fatty Acid Desaturase-Like Sequences

A skilled artisan can utilize the methods provided in the example above to identify additional nematode fatty acid desaturase-like sequences, e.g., fatty acid desaturase-like sequences (including Δ12 fatty acid desaturase sequences) from nematodes other than *M. incognita, H. glycines, D. immitis, S. stercoralis, R. axei* and/or *C. elegans*. In addition, nematode fatty acid desaturase-like sequences can be identified by a variety of methods including computer-based database searches, hybridization-based methods, and functional complementation.

Database Identification A nematode fatty acid desaturase-like sequence can be identified from a sequence database, e.g., a protein or nucleic acid database using a sequence disclosed herein as a query. Sequence comparison programs can be used to compare and analyze the nucleotide or amino acid sequences. One such software package is the BLAST suite of programs from the National Center for Biotechnology Institute (NCBI; Altschul et al. (1997) *Nuc. Acids Research* 25:3389–3402). A fatty acid desaturase-like sequence of the invention can be used to query a sequence database, such as nr, dbest (expressed sequence tag (EST) sequences), and htgs (high-throughput genome sequences), using a computer-based search, e.g., FASTA, BLAST, or PSI-BLAST search. Homologous sequences in other species (e.g., humans and animals) can be detected in a PSI-BLAST search of a database such as nr (E value=10, H value=1e-2, using, for example, four iterations; http://www.ncbi.nlm.nih.gov/). Sequences so obtained can be used to construct a multiple alignment, e.g., a ClustalX alignment, and/or to build a phylogenetic tree, e.g., in ClustalX using the Neighbor-Joining method (Saitou et al. (1987) *Mol. Biol. Evol.* 4:406–425) and bootstrapping (1000 replicates; Felsenstein (1985) *Evolution* 39:783–791). Distances maybe corrected for the occurrence of multiple substitutions [$D_{CORR}$=-ln(1-D-D$^2$/5) where D is the fraction of amino acid differences between two sequences] (Kimura (1983) *The Neutral Theory of Molecular Evolution*, Cambridge University Press).

The aforementioned search strategy can be used to identify fatty acid desaturase-like sequences in nematodes of the following non-limiting, exemplary genera:

Plant Parasitic Nematode Genera Include:

Afrina, Anguina, Aphelenchoides, Belonolaimus, Bursaphelenchus, Cacopaurus, Cactodera, Criconema, Criconemoides, Cryphodera, Ditylenchus, Dolichodorus, Dorylaimus, Globodera, Helicotylenchus, Hemicriconemoides, Hemicycliophora, Heterodera, Hirschmanniella, Hoplolaimus, Hypsoperine, Longidorus, Meloidogyne, Mesoanguina, Nacobbus, Nacobbodera, Panagrellus, Paratrichodorus, Paratylenchus, Pratylenchus, Pterotylench us, Punctodera, Radopholus, Rhadinaphelenchus, Rotylenchulus, Rotylenchus, Scutellonema, Subanguina, Thecavermiculatus, Trichodorus, Turbatrix, Tylenchorhynchus, Tylenchulus, Xiphinema.

Animal and Human Parasitic Nematode Genera Include:

Acanthocheilonema, Aelurostrongylus, Ancylostoma, Angiostrongylus, Anisakis, Ascaris, Ascarops, Bunostomum, Brugia, Capillaria, Chabertia, Cooperia, Crenosoma, Cyathostome species (Small Strongyles), Dictyocaulus, Dioctophyma, Dipetalonema, Dirofiliaria, Dracunculus, Draschia, Elaneophora, Enterobius, Filaroides, Gnathostoma, Gonylonema, Habronema, Haemonchus, Hyostrongylus, Lagochilascaris, Litomosoides, Loa, Mammomonogamus, Mansonella, Muellerius, Metastrongylid, Necator, Nematodirus, Nippostrongylus, Oesophagostomum, Ollulanus, Onchocerca, Ostertagia, Oxyspirura, Oxyuris, Parafilaria, Parascaris, Parastrongyloides, Parelaphostrongylus, Physaloptera, Physocephalus, Protostrongylus, Pseudoterranova, Setaria, Spirocerca, Stephanurus, Stephanofilaria, Strongyloides, Strongylus, Spirocerca, Syngamus, Teladorsagia, Thelazia, Toxascaris, Toxocara, Trichinella, Trichostrongylus, Trichuris, Uncinaria, and Wuchereria.

Particularly Preferred Nematode Genera Include:

Plant parasitic: Anguina, Aphelenchoides, Belonolaimus, Bursaphelenchus, Ditylenchus, Dolichodorus, Globodera, Heterodera, Hoplolaimus, Longidorus, Meloidogyne, Nacobbus, Pratylenchus, Radopholus, Rotylenchus, Tylenchulus, Xiphinema.

Animal & Human parasitic: Ancylostoma, Ascaris, Brugia, Capillaria, Cooperia, Cyathostome species, Dictyocaulus, Dirofiliaria, Dracunculus, Enterobius, Haemonchus, Necator, Nematodirus, Oesophagostomum, Onchocerca, Ostertagia, Oxyspirura, Oxyuris, Parascaris, Strongyloides, Strongylus, Syngamus, Teladorsagia, Thelazia, Toxocara, Trichinella, Trichostrongylus, Trichuris, and Wuchereria.

Particularly Preferred Nematode Species Include:

Plant parasitic: *Anguina tritici, Aphelenchoides fragariae, Belonolaimus longicaudatus, Bursaphelenchus xylophilus, Ditylenchus destructor, Ditylenchus dipsaci, Dolichodorus heterocephalous, Globodera pallida, Globodera rostochiensis, Globodera tabacum, Heterodera avenae, Heterodera cardiolata, Heterodera carotae, Heterodera cruciferae, Heterodera glycines, Heterodera major, Heterodera schachtii, Heterodera zeae, Hoplolaimus tylenchiformis, Longidorus sylphus, Meloidogyne acronea, Meloidogyne arenaria, Meloidogyne chitwoodi, Meloidogyne exigua, Meloidogyne graminicola, Meloidogyne hapla, Meloidogyne incognita, Meloiclogynejavanica, Meloidogyne nassi, Nacobbus batatiformis, Pratylenchus brachyurus, Pratylenchus coffeae, Pratylenchus penetrans, Pratylenchus scribneri, Pratylenchus zeae, Radopholus similis, Rotylenchus reniformis, Tylenchulus semipenetrans, Xiphinema americanum.*

Animal & Human parasitic: *Ancylostoma braziliense, Ancylostoma caninum, Ancylostoma ceylanicum, Ancylostoma duodenale, Ancylostoma tubaeforme, Ascaris suum, Ascaris lumbrichoides, Brugia malayi, Capillaria bovis, Capillaria plica, Capillaria feliscati, Cooperia oncophora, Cooperia punctata, Cyathostome species, Dictyocaulus filaria, Dictyocaulus viviparus, Dictyocaulus arnfieldi, Dirofiliaria immitis, Dracunculus insignis, Enterobius vermicularis, Haemonchus contortus, Haemonchus placei, Necator americanus, Nematodirus helvetianus, Oesophagostomum racliatum, Onchocerca volvulus, Onchocerca cervicalis, Ostertagia ostertagi, Ostertagia circumcincta, Oxyuris equi, Parascaris equorum, Strongyloides stercoralis, Strongylus vulgaris, Strongylus edentatus, Syngamus trachea, Teladorsagia circumcincta, Toxocara cati, Trichinella spiralis, Trichostrongylus axei, Trichostrongylus colubriformis, Trichuris vulpis, Trichuris suis, Trichurs trichiura,* and *Wuchereria bancrofti.*

Further, a fatty acid desaturase-like sequence can be used to identify additional fatty acid desaturase-like sequence homologs within a genome. Multiple homologous copies of a fatty acid desaturase-like sequence can be present. For example, a nematode fatty acid desaturase-like sequence can be used as a seed sequence in an iterative PSI-BLAST search (default parameters, substitution matrix=Blosum62, gap open=11, gap extend=1) of a nonredundant database such as wormpep (E value=1e-2, H value=1e-4, using, for example 4 iterations) to determine the number of homologs in a database, e.g., in a database containing the complete genome of an organism. A nematode fatty acid desaturase-like sequence can be present in a genome along with 1, 2, 3, 4, 5, 6, 8, 10, or more homologs.

Hybridization Methods A nematode fatty acid desaturase-like sequence can be identified by a hybridization-based method using a sequence provided herein as a probe. For example, a library of nematode genomic or cDNA clones can be hybridized under low stringency conditions with the probe nucleic acid. Stringency conditions can be modulated to reduce background signal and increase signal from potential positives. Clones so identified can be sequenced to verify that they encode fatty acid desaturase-like sequences.

Another hybridization-based method utilizes an amplification reaction (e.g., the polymerase chain reaction (PCR)). Oligonucleotides, e.g., degenerate oligonucleotides, are designed to hybridize to a conserved region of a fatty acid desaturase-like sequence. The oligonucleotides are used as primers to amplify a fatty acid desaturase-like sequence from template nucleic acid from a nematode, e.g., a nematode other than *M. incognita*, and/or *C. elegans*. The amplified fragment can be cloned and/or sequenced.

Complementation Methods A nematode fatty acid desaturase-like sequence can be identified from a complementation screen for a nucleic acid molecule that restores fatty acid desaturase-like activity to a cell lacking a fatty acid desaturase-like activity. Routine methods can be used to construct strains (i.e., nematode, yeast, bacterial strains) that lack fatty acid desaturase activity. For example, a nematode strain mutated at the fatty acid desaturase gene locus can be grown (i.e., rescued) on supplements such as Δ12 unsaturated fatty acids. Such a strain can be transformed with nematode cDNAs predicted to encode fatty acid desaturases. Strains can be identified in which fatty acid desaturase activity is restored by selecting for those transgenic lines that exhibit growth in the absensce of supplemental Δ12 unsaturated fatty acids. The plasmid harbored by the rescued strain can be recovered to identify and/or characterize the inserted nematode cDNA that provides fatty acid desaturase-like activity when expressed. Similarly, a bacterial and/or yeast strain can be used as a selection system, whereby the Δ12 fatty acid desaturase gene(s) can be mutated using, for example, phage transduction (Clark et al. (1983) *Biochem.* 22:5897–5902; Simon et al. (1980) *J. Bacteriology* 142:621–632). The mutant cell line can be sustained on exongenous unsaturated fatty acids. A strain lacking Δ12 fatty acid desaturase gene(s) can be transformed with a plasmid library expressing nematode cDNAs. Strains can be identified in which fatty acid desaturase activity is restored, i.e., that can grow in the absence of exogenous fatty acids. In still another embodiment, a microorganism (i.e., a yeast strain) that naturally does not contain a Δ12 fatty acid desaturase can be transformed with plasmids expressing nematode genes. Transformed strains that exhibit Δ12 fatty acid desaturase activity can be identified using, GC analysis to measure fatty acid composition. Those clones that convert oleic acid to linoleic acid can be selected, for example (Sakurdani et al. (1999) *Eur. J. Biochem.* 261:812–820.

Full-length cDNA and Sequencing Methods The following methods can be used, e.g., alone or in combination with another method described herein, to obtain full-length nematode fatty acid desaturase-like genes and determine their sequences.

Plant parasitic nematodes are maintained on greenhouse pot cultures depending on nematode preference. Root Knot Nematodes (*Meloidogyne* sp) are propagated on Rutgers tomato (Burpee), while Soybean Cyst Nematodes (*Heterodera* sp) are propagated on soybean. Total nematode RNA is isolated using the TRIZOL reagent (Gibco BRL). Briefly, 2 ml of packed worms are combined with 8 ml TRIZOL reagent and solubilized by vortexing. Following 5 minutes of incubation at room temperature, the samples are divided into smaller volumes and spun at 14,000×g for 10 minutes at 4° C. to remove insoluble material. The liquid phase is extracted with 200 μl of chloroform, and the upper aqueous phase is removed to a fresh tube. The RNA is precipitated by the addition of 500 μl of isopropanol and centrifuged to pellet. The aqueous phase is carefully removed, and the pellet is washed in 75% ethanol and spun to re-collect the RNA pellet. The supernatant is carefully removed, and the pellet is air dried for 10 minutes. The RNA pellet is resuspended in 50 μl of DEPC-$H_2O$ and analyzed by spectrophotometry at λ 260 and 280 nm to determine yield and purity. Yields can be 1–4 mg of total RNA from 2 ml of packed worms.

Full-length cDNAs can be generated using 5' and 3' RACE techniques in combination with EST sequence information. The molecular technique 5' RACE (Life Technologies, Inc., Rockville, Md.) can be employed to obtain complete or near-complete 5' ends of cDNA sequences for nematode fatty acid desaturase-like cDNA sequences. Briefly, following the instructions provided by Life Technologies, first strand cDNA is synthesized from total nematode RNA using Murine Leukemia Virus Reverse Transcriptase (M-MLV RT) and a gene specific "antisense" primer, e.g., designed from available EST sequence. RNase H is used to degrade the original mRNA template. The first strand cDNA is separated from unincorporated dNTPs, primers, and proteins using a GlassMAX Spin Cartridge. Terminal deoxynucleotidyl transferase (TdT) is used to generate a homopolymeric dC tailed extension by the sequential addition of dCTP nucleotides to the 3' end of the first strand cDNA. Following addition of the dC homopolymeric extension, the first strand cDNA is directly amplified without further purification using Taq DNA polymerase, a gene specific "antisense" primer designed from available EST sequences to anneal to a site located within the first strand cDNA molecule, and a deoxyinosine-containing primer that anneals to the homopolymeric dC tailed region of the cDNA in a polymerase chain reaction (PCR). 5' RACE PCR amplification products are cloned into a suitable vector for further analysis and sequencing.

The molecular technique, 3' RACE (Life Technologies, Inc., Rockville, Md.), can be employed to obtain complete or near-complete 3' ends of cDNA sequences for nematode fatty acid desaturase-like cDNA sequences. Briefly, following the instructions provided by Life Technologies (Rockville, Md.), first strand cDNA synthesis is performed on total nematode RNA using SuperScript™ Reverse Transcriptase and an oligo-dT primer that anneals to the polyA tail. Following degradation of the original mRNA template with RNase H, the first strand cDNA is directly PCR amplified without further purification using Taq DNA polymerase, a gene specific primer designed from available EST sequences to anneal to a site located within the first strand cDNA molecule, and a "universal" primer which contains sequence identity to 5' end of the oligo-dT primer.

3' RACE PCR amplification products are cloned into a suitable vector for further analysis and sequencing.

Nucleic Acid Variants

Isolated nucleic acid molecules of the present invention include nucleic acid molecules that have an open reading frame encoding a fatty acid desaturase-like polypeptide. Such nucleic acid molecules include molecules having: the sequences recited in SEQ ID NO: 1, 2, 3, 4, 5, 6 and/or 7; and sequences coding for the fatty acid desaturase-like proteins recited in SEQ ID NO: 8, 9, 10, 11, 12, 13 and/or 14. These nucleic acid molecules can be used, for example, in a hybridization assay to detect the presence of a *M. incognita, H. glycines, D. immitis, S. stercoralis* or *R. axei* nucleic acid in a sample.

The present invention includes nucleic acid molecules such as those shown in SEQ ID NO: 1, 2, 3, 4, 5, 6 and/or 7 that may be subjected to mutagenesis to produce single or multiple nucleotide substitutions, deletions, or insertions. Nucleotide insertional derivatives of the nematode gene of the present invention include 5' and 3' terminal fusions as well as intra-sequence insertions of single or multiple nucleotides. Insertional nucleotide sequence variants are those in which one or more nucleotides are introduced into a predetermined site in the nucleotide sequence, although random insertion is also possible with suitable screening of the resulting product. Deletion variants are characterized by the removal of one or more nucleotides from the sequence. Nucleotide substitution variants are those in which at least one nucleotide in the sequence has been removed and a different nucleotide inserted in its place. Such a substitution may be silent (e.g., synonymous), meaning that the substitution does not alter the amino acid defined by the codon. Alternatively, substitutions are designed to alter one amino acid for another amino acid (e.g., non-synonymous). A non-synonymous substitution can be conservative or non-conservative. A substitution can be such that activity, e.g., fatty acid desaturase-like activity, is not impaired. A conservative amino acid substitution results in the alteration of an amino acid for a similar acting amino acid, or amino acid of like charge, polarity, or hydrophobicity, e.g., an amino acid substitution listed in Table 3 below. At some positions, even conservative amino acid substitutions can disrupt the activity of the polypeptide.

TABLE 4

Conservative Amino Acid Replacements

| For Amino Acid | Code | Replace with any of . . . |
|---|---|---|
| Alanine | Ala | Gly, Cys, Ser |
| Arginine | Arg | Lys, His |
| Asparagine | Asn | Asp, Glu, Gln, |
| Aspartic Acid | Asp | Asn, Glu, Gln |
| Cysteine | Cys | Met, Thr, Ser |
| Glutamine | Gln | Asn, Glu, Asp |
| Glutamic Acid | Glu | Asp, Asn, Gln |
| Glycine | Gly | Ala |
| Histidine | His | Lys, Arg |
| Isoleucine | Ile | Val, Leu, Met |
| Leucine | Leu | Val, Ile, Met |
| Lysine | Lys | Arg, His |
| Methionine | Met | Ile, Leu, Val |
| Phenylalanine | Phe | Tyr, His, Trp |
| Proline | Pro |  |
| Serine | Ser | Thr, Cys, Ala |
| Threonine | Thr | Ser, Met, Val |
| Tryptophan | Trp | Phe, Tyr |
| Tyrosine | Tyr | Phe, His |
| Valine | Val | Leu, Ile, Met |

The current invention also embodies splice variants of nematode fatty acid desaturase-like sequences.

Another aspect of the present invention embodies a polypeptide-encoding nucleic acid molecule that is capable of hybridizing under conditions of low stringency (or high stringency) to the nucleic acid molecule put forth in SEQ ID NO: 1, 2, 3, 4, 5, 6 and/or 7 or their complements.

The nucleic acid molecules that encode for fatty acid desaturase-like polypeptides may correspond to the naturally occurring nucleic acid molecules or may differ by one or more nucleotide substitutions, deletions, insertions, and/or additions. Thus, the present invention extends to genes and any functional mutants, derivatives, parts, fragments, naturally occurring polymorphisms, homologs or analogs thereof or non-functional molecules. Such nucleic acid molecules can be used to detect polymorphisms of fatty acid desaturase genes or fatty acid desaturase-like genes, e.g., in other nematodes. As mentioned below, such molecules are useful as genetic probes; primer sequences in the enzymatic or chemical synthesis of the gene; or in the generation of immunologically interactive recombinant molecules. Using the information provided herein, such as the nucleotide sequence SEQ ID NO: 1, 2, 3, 4, 5, 6 and/or 7, a nucleic acid molecule encoding a fatty acid desaturase-like molecule may be obtained using standard cloning and a screening techniques, such as a method described herein.

Nucleic acid molecules of the present invention can be in the form of RNA, such as mRNA, or in the form of DNA, including, for example, cDNA and genomic DNA obtained by cloning or produced synthetically. The DNA may be double-stranded or single-stranded. The nucleic acids may be in the form of RNA/DNA hybrids. Single-stranded DNA or RNA can be the coding strand, also referred to as the sense strand, or the non-coding strand, also known as the anti-sense strand.

Expression of Fatty Acid Desaturase-Like Polypeptides

One embodiment of the present invention includes a recombinant nucleic acid molecule, which includes at least one isolated nucleic acid molecule depicted in SEQ ID NO: 1, 2, 3, 4, 5, 6 and/or 7, inserted in a vector capable of delivering and maintaining the nucleic acid molecule into a cell. The DNA molecule may be inserted into an autonomously replicating factor (suitable vectors include, for example, pGEM3Z and pcDNA3, and derivatives thereof). The vector nucleic acid may be a bacteriophage DNA such as bacteriophage lambda or M13 and derivatives thereof. The vector may be either RNA or DNA, single- or double-stranded, prokaryotic, eukaryotic, or viral. Vectors can include transposons, viral vectors, episomes, (e.g., plasmids), chromosomes inserts, and artificial chromosomes (e.g. BACs or YACs). Construction of a vector containing a nucleic acid described herein can be followed by transformation of a host cell such as a bacterium. Suitable bacterial hosts include, but are not limited to, *E. coli*. Suitable eukaryotic hosts include yeast such as *S. cerevisiae*, other fungi, vertebrate cells, invertebrate cells (e.g., insect cells), plant cells, human cells, human tissue cells, and whole eukaryotic organisms. (e.g., a transgenic plant or a transgenic animal). Further, the vector nucleic acid can be used to generate a virus such as vaccinia or baculovirus.

The present invention also extends to genetic constructs designed for polypeptide expression. Generally, the genetic construct also includes, in addition to the encoding nucleic acid molecule, elements that allow expression, such as a promoter and regulatory sequences. The expression vectors may contain transcriptional control sequences that control transcriptional initiation, such as promoter, enhancer, operator, and repressor sequences. A variety of transcriptional control sequences are well known to those in the art and may be functional in, but are not limited to, a bacterium, yeast, plant, or animal cell. The expression vector can also include a translation regulatory sequence (e.g., an untranslated 5' sequence, an untranslated 3' sequence, a poly A addition site, or an internal ribosome entry site), a splicing sequence or splicing regulatory sequence, and a transcription termination sequence. The vector can be capable of autonomous replication or it can integrate into host DNA.

In an alternative embodiment, the DNA molecule is fused to a reporter gene such as β-glucuronidase gene, β-galactosidase (lacZ), chloramphenicol-acetyltransferase gene, a gene encoding green fluorescent protein (and variants thereof), or red fluorescent protein firefly luciferase gene, among others. The DNA molecule can also be fused to a nucleic acid encoding a polypeptide affinity tag, e.g. glutathione S-transferase (GST), maltose E binding protein, protein A, FLAG tag, hexa-histidine, or the influenza HA tag. The affinity tag or reporter fusion joins the reading frames of SEQ ID NO: 1, 2, 3, 4, 5, 6 and/or 7 to the reading frame of the reporter gene encoding the affinity tag such that a translational fusion is generated. Expression of the fusion gene results in translation of a single polypeptide that includes both a nematode fatty acid desaturase-like region and a reporter protein or affinity tag. The fusion can also join a fragment of the reading frame of SEQ ID NO: 1, 2, 3, 4, 5, 6 and/or 7. The fragment can encode a functional region of the fatty acid desaturase-like polypeptides, a structurally intact domain, or an epitope (e.g., a peptide of about 8, 10, 20, or 30 or more amino acids). A nematode fatty acid desaturase-like nucleic acid that includes at least one of a regulatory region (e.g., a 5' regulatory region, a promoter, an enhancer, a 5' untranslated region, a translational start site, a 3' untranslated region, a polyadenylation site, or a 3' regulatory region) can also be fused to a heterologous nucleic acid. For example, the promoter of a fatty acid desaturase-like nucleic acid can be fused to a heterologous nucleic acid, e.g., a nucleic acid encoding a reporter protein.

Suitable cells to transform include any cell that can be transformed with a nucleic acid molecule of the present invention. A transformed cell of the present invention is also herein referred to as a recombinant or transgenic cell. Suitable cells can either be untransformed cells or cells that have already been transformed with at least one nucleic acid molecule. Suitable cells for transformation according to the present invention can either be: (i) endogenously capable of expressing the fatty acid desaturase-like protein or; (ii) capable of producing such protein after transformation with at least one nucleic acid molecule of the present invention.

In an exemplary embodiment, a nucleic acid of the invention is used to generate a transgenic nematode strain, e.g., a transgenic *C. elegans* strain. To generate such a strain, nucleic acid linked to a *C. elegans* promoter is injected into the gonad of a nematode, thus generating a heritable extra-chromosomal array containing the nucleic acid (see, e.g., Mello et al. (1991) *EMBO J.* 10:3959–3970). The transgenic nematode can be propagated to generate a strain harboring the transgene. To identify specific inhibitors of the *M. incognita, H. glycines, D. immitis, S. stercoralis* or *R. axei* Δ12 FAT2, the *C. elegans* Δ12 FAT gene can be "knocked out" by continuous growth on *E. coli* engineered to produce dsRNA homologous to the *C. elegans* Δ12 FAT gene (described earlier). Nematodes of the strain can be used in screens to identify inhibitors specific for a *M. incognita, H. glycines, D. immitis, S. stercoralis* or *R. axei* fatty acid desaturase-like gene.

In another embodiment, a nucleic acid of the invention can be cloned behind a yeast-specific transcription promoter can be used to generate a transgenic yeast strain, such as *Saccharomyces cerevisiae*. The *S. cerevisiae* strain can be transformed using the lithium acetate procedure (Ito et al. (1983) *J. Bacteriology* 153:163–168; Sakuradani (1999) *Eur J. Biochem.* 261:812–820). Such a strain can be used to identify inhibitors specific for a *M. incognita, H. glycines, D. immitis, S. stercoralis* or *R. axei* fatty acid desaturase-like polypeptide.

Production of Fatty Acid Desaturase-Like Polypeptide Substrates and Inhibitors

In still another embodiment, a nucleic acid of the invention can be used to generate a transgenic plant such as *Arabidopsis thaliana*, a model legume *Medicago truncatula*, or any plant of interest, e.g., a nematode host. For example, the fatty acid desaturase like-gene can be cloned into a vector under the control of the cauliflower mosaic virus (CaMV) 35S promoter/nopaline synthase terminator cassette (Baulcombe et al. (1986) *Nature* 321:446–449) which can then be introduced into an *Agrobacterium* strain by the freeze thaw method. *Agrobacterium*-mediated transformation can be accomplished by the planta-vacuum-infiltration method (Bouchez et al. (1993) *C.R. Acad. Sci. Paris* 316:1188–1193) and transformed transgeneic plant lines can be selected (Spychalla et al. (1997) *Proc. Natl. Acad. Sci.* 94:1142–1147). Such a plant line can be used to identify inhibitors specific for *M. incognita, H. glycines, D. immitis, S. stercoralis* or *R. axei* fatty acid desaturase-like polypeptides or other plant fatty acid desaturase-like polypeptides. Fatty acid desaturase can be expressed in soybean and/or soybean somatic embryos using, for example, particle bombardment method of transformation (Finer et al. (1991) *In Vitro Cell. Dev. Biol.* 27:175–182; Cahoon et al. (1999) *Proc. Natl. Acad. Sci. USA* 96: 12935–12940). It is also desirable to generate plants with increased resistance to inhibitors of fatty acid desaturase-like polypeptides by providing the plant with a transgene expressing a fatty acid desaturase. A transformed cell that harbors a *M. incognita* fatty acid desaturase polypeptide may naturally produce products of Δ12 fatty acid desaturases (e.g. linoleic acid). In this circumstance, the cell may produce a higher proportion of Δ12-desaturated fatty acids than an otherwise similar cell lacking the *M. incognita, H. glycines, D. immitis, S. stercoralis* or *R. axei* fatty acid desaturase polypeptide.

If the host cell does not naturally produce a substrate for fatty acid desaturase, one or more substrates can be provided exogenously to cells transformed with an expressible fatty acid desaturase polynucleotide (e.g., by topical application (Spychalla et al. (1997) *Proc. Natl. Acad. Sci. USA* 94:1142–1147)), or fatty acid desaturase can be co-expressed in cells together with one or more cloned genes that encode polypeptides that can produce substrate compounds from precursor compounds in such cells.

A transformed cell may also be engineered that harbors a polypeptide that produces inhibitors of the Δ12 fatty acid desaturase-like gene of nematodes. For example, a cell may be engineered to produce a Δ12 hydroxylase, a Δ12 acetylenase, and/or a Δ12 epoxygenase. Such polypeptides may produce fatty acid analogs that inhibit the nematode Δ12 fatty acid desaturase-like polypeptide (i.e., ricinoleic acid, crepenynic acid, and vernolic acid). Such genes may be linked to a root-specific promoter and transformed into a plant, for example. Examples of suitable genes include: *Crepsis palaestina* Δ12 fatty acid epoxygenase (GenBank® Accession No. CAA76156; produces vernolic acid); *Crepis alpina* Δ12 fatty acid acetylenase (GenBank® Accession No. CAA76158; produces crepenynic acid); *Ricinus Communis* oleate 12-hydroxylase (GenBank® Accession No.

AAC49010; produces ricinoleic acid); *Momordica charantia* Δ12 oleic desaturase-like protein (GenBank® Accession No. AAF05916; produces alpha-eleostearic acid); and *Impatiens balsamina* Δ12 oleic acid desaturase-like protein (GenBank® Accession No. AAF05915; produces alpha-eleostearic acid).

Oligonucleotides

Also provided are oligonucleotides that can form stable hybrids with a nucleic acid molecule of the present invention. The oligonucleotides can be about 10 to 200 nucleotides, about 15 to 120 nucleotides, or about 17 to 80 nucleotides in length, e.g., about 10, 20, 30, 40, 50, 60, 80, 100, 120 nucleotides in length. The oligonucleotides can be used as probes to identify nucleic acid molecules, primers to produce nucleic acid molecules, or therapeutic reagents to inhibit nematode fatty acid desaturase-like protein activity or production (e.g., antisense, triplex formation, ribozyme, and/or RNA drug-based reagents). The present invention includes oligonucleotides of RNA (ssRNA and dsRNA), DNA, or derivatives of either. The invention extends to the use of such oligonucleotides to protect non-nematode organisms (for example e.g., plants and animals) from disease by reducing the viability of infecting namatodes, e.g., using a technology described herein. Appropriate oligonucleotide-containing therapeutic compositions can be administered to a non-nematode organism using techniques known to those skilled in the art, including, but not limited to, transgenic expression in plants or animals.

Primer sequences can be used to amplify a fatty acid desaturase-like nucleic acid or fragment thereof. For example, at least 10 cycles of PCR amplification can be used to obtain such an amplified nucleic acid. Primers can be at least about 8–40, 10–30 or 14–25 nucleotides in length, and can anneal to a nucleic acid "template molecule", e.g., a template molecule encoding a fatty acid desaturase-like genetic sequence, or a functional part thereof, or its complementary sequence. The nucleic acid primer molecule can be any nucleotide sequence of at least 10 nucleotides in length derived from, or contained within sequences depicted in SEQ ID NO: 1, 2, 3, 4, 5, 6 and/or 7 and their complements. The nucleic acid template molecule may be in a recombinant form, in a virus particle, bacteriophage particle, yeast cell, animal cell, plant cell, fungal cell, or bacterial cell. A primer can be chemically synthesized by routine methods.

This invention embodies any fatty acid desaturase-like sequences that are used to identify and isolate similar genes from other organisms, including nematodes, prokaryotic organisms, and other eukaryotic organisms, such as other animals and/or plants.

In another embodiment, the invention provides oligonucleotides that are specific for a *M. incognita, H. glycines, D. immitis, S. stercoralis* or *R. axei* fatty acid desaturase-like nucleic acid molecule. Such oligonucleotides can be used in a PCR test to determine if a *M. incognita, H. glycines, D. immitis, S. stercoralis* or *R. axei* nucleic acid is present in a sample, e.g., to monitor a disease caused *M. incognita, H. glycines, D. immitis* or *S. stercoralis*.

Protein Production

Isolated fatty acid desaturase-like proteins from nematodes can be produced in a number of ways, including production and recovery of the recombinant proteins and/or chemical synthesis of the protein. In one embodiment, an isolated nematode fatty acid desaturase-like protein is produced by culturing a cell, e.g., a bacterial, fungal, plant, or animal cell, capable of expressing the protein, under conditions for effective production and recovery of the protein. The nucleic acid can be operably linked to a heterologous promoter, e.g., an inducible promoter or a constitutive promoter. Effective growth conditions are typically, but not necessarily, in liquid media comprising salts, water, carbon, nitrogen, phosphate sources, minerals, and other nutrients, but may be any solution in which fatty acid desaturase-like proteins may be produced.

In one embodiment, recovery of the protein may refer to collecting the growth solution and need not involve additional steps of purification. Proteins of the present invention, however, can be purified using standard purification techniques, such as, but not limited to, affinity chromatography, thermaprecipitation, immunoaffinity chromatography, ammonium sulfate precipitation, ion exchange chromatography, filtration, electrophoresis, hydrophobic interaction chromatography, and others.

The fatty acid desaturase-like polypeptide can be fused to an affinity tag, e.g., a purification handle (e.g., glutathione-S-reductase, hexa-histidine, maltose binding protein, dihydrofolate reductases, or chitin binding protein) or an epitope tag (e.g., c-myc epitope tag, FLAG™ tag, or influenza HA tag). Affinity tagged and epitope tagged proteins can be purified using routine art-known methods.

Antibodies Against Fatty Acid Desaturase-Like Polypeptides

Recombinant fatty acid desaturase-like gene products or derivatives thereof can be used to produce immunologically interactive molecules, such as antibodies, or functional derivatives thereof. Useful antibodies include those that bind to a polypeptide that has substantially the same sequence as the amino acid sequences recited in SEQ ID NO: 8, 9, 10, 11, 12, 13 and/or 14, or that has at least 80% similarity over 50 or more amino acids to these sequences. In a preferred embodiment, the antibody specifically binds to a polypeptide having the amino acid sequence recited in SEQ ID NO: 8, 9, 10, 11, 12, 13 and/or 14. The antibodies can be antibody fragments and genetically engineered antibodies, including single chain antibodies or chimeric antibodies that can bind to more than one epitope. Such antibodies may be polyclonal or monoclonal and may be selected from naturally occurring antibodies or may be specifically raised to a recombinant fatty acid desaturase-like protein.

Antibodies can be derived by immunization with a recombinant or purified fatty acid desaturase-like gene or gene product. As used herein, the term "antibody" refers to an immunoglobulin, or fragment thereof. Examples of antibody fragments include F(ab) and F(ab')$_2$ fragments, particularly functional ones able to bind epitopes. Such fragments can be generated by proteolytic cleavage, e.g., with pepsin, or by genetic engineering. Antibodies can be polyclonal, monoclonal, or recombinant. In addition, antibodies can be modified to be chimeric, or humanized. Further, an antibody can be coupled to a label or a toxin.

Antibodies can be generated against a full-length fatty acid desaturase-like protein, or a fragment thereof, e.g., an antigenic peptide. Such polypeptides can be coupled to an adjuvant to improve immunogenicity. Polyclonal serum is produced by injection of the antigen into a laboratory animal such as a rabbit and subsequent collection of sera. Alternatively, the antigen is used to immunize mice. Lymphocytic cells are obtained from the mice and fused with myelomas to form hybridomas producing antibodies.

Peptides for generating fatty acid desaturase-like antibodies can be about 8, 10, 15, 20, 30 or more amino acid residues in length, e.g., a peptide of such length obtained from SEQ ID NO: 8, 9, 10, 11, 12, 13 and/or 14. Peptides or epitopes can also be selected from regions exposed on the surface of the protein, e.g., hydrophilic or amphipathic regions. An epitope in the vicinity of the active or binding site can be selected such that an antibody binding such an epitope would block access to the active site or prevent binding. Antibodies reactive with, or specific for, any of these regions, or other regions or domains described herein are provided. An antibody to a fatty acid desaturase-like protein can modulate a fatty acid desaturase-like activity.

Monoclonal antibodies, which can be produced by routine methods, are obtained in abundance and in homogenous form from hybridomas formed from the fusion of immortal cell lines (e.g., myelomas) with lymphocytes immunized with fatty acid desaturase-like polypeptides such as those set forth in SEQ ID NO: 8, 9, 10, 11, 12, 13 and/or 14.

In addition, antibodies can be engineered, e.g., to produce a single chain antibody (see, for example, Colcher et al. (1999) *Ann N Y Acad Sci* 880: 263–80; and Reiter (1996) *Clin Cancer Res* 2: 245–52). In still another implementation, antibodies are selected or modified based on screening procedures, e.g., by screening antibodies or fragments thereof from a phage display library.

Antibodies of the present invention have a variety of important uses within the scope of this invention. For example, such antibodies can be used: (i) as therapeutic compounds to passively immunize an animal in order to protect the animal from nematodes susceptible to antibody treatment; (ii) as reagents in experimental assays to detect presence of nematodes; (iii) as tools to screen for expression of the gene product in nematodes, animals, fungi, bacteria, and plants; and/or (iv) as a purification tool of fatty acid desaturase-like protein; (v) as fatty acid desaturase inhibitors/activators that can be expressed or introduced into plants or animals for therapeutic purposes.

An antibody against a fatty acid desaturase-like protein can be produced in a plant cell, e.g., in a transgenic plant or in culture (see, e.g., U.S. Pat. No. 6,080,560).

Antibodies that specifically recognize a *M. incognita, H. glycines, D. immitis, S. stercoralis* or *R. axei* fatty acid desaturase-like proteins can be used to identify a *M. incognita, H. glycines, D. iinmitis, S. stercoralis* or *R. axei* nematodes, and, thus, can be used to monitor a disease caused by *M. incognita, H. glycines, D. immitis* or *S. stercoralis*.

Nucleic Acids Agents

Also featured are isolated nucleic acids that are antisense to nucleic acids encoding nematode fatty acid desaturase-like proteins. An "antisense" nucleic acid includes a sequence that is complementary to the coding strand of a nucleic acid encoding a fatty acid desaturase-like protein. The complementarity can be in a coding region of the coding strand or in a noncoding region, e.g., a 5' or 3' untranslated region, e.g., the translation start site. The antisense nucleic acid can be produced from a cellular promoter (e.g., a RNA polymerase II or III promoter), or can be introduced into a cell, e.g., using a liposome. For example, the antisense nucleic acid can be a synthetic oligonucleotide having a length of about 10, 15, 20, 30, 40, 50, 75, 90, 120 or more nucleotides in length.

An antisense nucleic acid can be synthesized chemically or produced using enzymatic reagents, e.g., a ligase. An antisense nucleic acid can also incorporate modified nucleotides, and artificial backbone structures, e.g., phosphorothioate derivative, and acridine substituted nucleotides.

Ribozymes: The antisense nucleic acid can be a ribozyme. The ribozyme can be designed to specifically cleave RNA, e.g., a fatty acid desaturase-like mRNA. Methods for designing such ribozymes are described in U.S. Pat. No. 5,093,246 or Haselhoff and Gerlach (1988) *Nature* 334:585–591. For example, the ribozyme can be a derivative of Tetrahymena L-19 IVS RNA in which the nucleotide sequence of the active site is modified to be complementary to a fatty acid desaturase-like nucleic acid (see, e.g., Cech et al. U.S. Pat. No. 4,987,071; and Cech et al. U.S. Pat. No. 5,116,742).

Peptide Nucleic acid (PNA): An antisense agent directed against a fatty acid desaturase-like nucleic acid can be a peptide nucleic acid (PNA). See Hyrup et al. (1996) *Bioorganic & Medicinal Chemistry* 4: 5–23) for methods and a description of the replacement of the deoxyribose phosphate backbone for a pseudopeptide backbone. A PNA can specifically hybridize to DNA and RNA under conditions of low ionic strength as a result of its electrostatic properties. The synthesis of PNA oligomers can be performed using standard solid phase peptide synthesis protocols as described in Hyrup et al. (1996) supra and Perry-O'Keefe et al. *Proc. Natl. Acad. Sci.* 93: 14670–675.

RNA Mediated Interference (RNAi): A double stranded RNA (dsRNA) molecule can be used to inactivate expression of a fatty acid desaturase-like gene in a cell by a process known as RNA mediated-interference (RNAi; e.g., Fire et al. (1998) *Nature* 391:806–811, and Gönczy et al. (2000) *Nature* 408:331–336). The dsRNA molecule can have the nucleotide sequence of a fatty acid desaturase-like nucleic acid described herein or a fragment thereof. The molecule can be injected into a cell, or a syncitia, e.g., a nematode gonad as described in Fire et al., supra.

In one embodiment, dsRNA can be introduced by soaking of nematodes. Double-stranded RNA may be introduced to nematodes by directly soaking individual worms in a solution of dsRNA. Soaking of *C. elegans* in a solution of dsRNA can be accomplished essentially as described in Tabar et al. ((1998) *Science* 282:430–1)). Briefly, Hermaphrodite L4-stage *C. elegans* are washed twice in siliconized tubes with approximately 1 ml M9 buffer (5 g/L NaCl, 11.32 g/L $Na_2HPO_4.7H_2O$, 3 g/L $KH_2PO_4$, 1 mM $MgSO_4$). In each wash, the worms are allowed to settle for 10 minutes and most of the supernatant removed. Between five and twenty worms in minimal volume (5–10 ul) are transferred to a fresh siliconized tube and an equal volume of specific dsRNA (resuspended in sterile, RNase-free water) is added. The final concentration of dsRNA is generally between 0.1 and 3.0 mg/ml. Up to 10% (v/v) lipofectin (Gibco-BRL) may be added to the mix. The mixture is incubated for 10 to 30 hours at a constant temperature between 15° and 23° C. The worms are then transferred individually to NGM-agar plates containing a lawn of *E. coli* (such as strain OP50), incubated at constant temperature between 15° and 23° C. and scored daily for phenotypes of the worms and their progeny for at least four consecutive days.

Screening Assays

Another embodiment of the present invention is a method of identifying a compound capable of altering (e.g., inhibiting or enhancing) the activity of fatty acid desaturase-like molecules. This method, also referred to as a "screening assay," herein, includes, but is not limited to, the following procedure: (i) contacting an isolated fatty acid desaturase-like protein with a test inhibitory compound under conditions in which, in the absence of the test compound, the protein has fatty acid desaturase-like activity; and (ii) determining if the test compound alters the fatty acid desaturase-like activity or alters the ability of the fatty acid desaturase to regulate other polypeptides or molecules e.g., the ability of the enzyme to desaturate fatty acids. Suitable inhibitors or activators that alter a nematode fatty acid desaturase-like activity include compounds that interact directly with a nematode fatty acid desaturase-like protein, perhaps but not necessarily, in the active or binding site. They can also interact with other regions of the nematode fatty acid desaturase protein by binding to regions outside of the active site or site responsible for regulation, for example, by allosteric interaction.

In one embodiment, an *M. incognita, H. glycines, D. immitis, S. stercoralis* or *R. axei* fatty acid desaturase-like polypeptide is expressed in a yeast cell, for example in *S. cerevisiae*, as has been described for a *C. elegans* FAT-2-like polypeptide (Peyo-Ndi (2000) *Archives of Biochemistry and Biophysics* 376:399–408). Overall fatty acid composition from wild-type and fatty acid desaturase-harboring yeast can than be assessed using, for example, gas-chromotography-mass spectrometry techniques (GC-MS). Optimally, an increase in Δ12 unsaturated fatty acids would be concomitant with introduction of an *M. incognita, H. glycines, D. immitis, S. stercoralis* or *R. axei* fatty acid desaturase-like polypeptide into the yeast strain. Test compounds can then be added to the yeast strain and fatty acid composition can be measured. A test compound that alters fatty acid composition, particularly decreases Δ12 unsaturated fatty acids in the yeast strain harboring the *M. incognita, H. glycines, D. immitis, S. stercoralis* or *R. axei* fatty acid desaturase-like polypeptides would be considered candidate compounds.

In one embodiment, an *M. incognita, H. glycines, D. immitis, S. stercoralis* or *R. axei* fatty acid desaturase-like polypeptide is expressed in a eukaryotic or plant cell, for example in Chinese hamster ovary cells or rabbit skin cells. Overall fatty acid composition from wild-type and fatty acid desaturase-harboring eukaryotic cells can than be assessed using, for example, gas chromatography-mass spectrometry techniques (GC-MS). Optimally, an increase in Δ12 unsaturated fatty acids would be concomitant with introduction of an *M. incognita, H. glycines, D. immitis, S. stercoralis* or *R. axei* fatty acid desaturase-like polypeptide into the cells. Test compounds can then be added to the eukaryotic cells and fatty acid composition can be measured. A test compound that alters fatty acid composition, particularly decreases Δ12 unsaturated fatty acids in the cells harboring the *M. incognita, H. glycines, D. immitis, S. stercoralis* or *R. axei* fatty acid desaturase-like polypeptides would be considered candidate compounds.

Similarly, a *M. incognita, H. glycines, D. immitis, S. stercoralis* or *R. axei* fatty acid desaturase-like polypeptides can be expressed in plants, for example in soybean, cotton, tobacco, potato, *M. truncatula*, and/or Arabidopsis. Plants used for transformation may have a functional Δ12 fatty acid desaturase gene or may be deficient in Δ12 fatty acid desaturase activity. Relative amounts of fatty acids can be measured and compared. Compounds that alter fatty acid compositions, particularly those that decrease Δ12 unsaturated fatty acids, would be candidate compounds.

Compounds: A test compound can be a large or small molecule, for example, an organic compound with a molecular weight of about 100 to 10,000; 200 to 5,000; 200 to 2000; or 200 to 1,000 daltons. A test compound can be any chemical compound, for example, a small organic molecule, a carbohydrate, a lipid, an amino acid, a polypeptide, a nucleoside, a nucleic acid, or a peptide nucleic acid. Small molecules include, but are not limited to, metabolites, metabolic analogues, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds). Compounds and components for synthesis of compounds can be obtained from a commercial chemical supplier, e.g., Sigma-Aldrich Corp. (St. Louis, Mo.). The test compound or compounds can be naturally occurring, synthetic, or both. A test compound can be the only substance assayed by the method described herein. Alternatively, a collection of test compounds can be assayed either consecutively or concurrently by the methods described herein. A compound may be an analog. Specifically, inhibitors may be analogs of fatty acids, for example, cyclypropenoid analogs of linoleic acid. Epoxy fatty acids (vernolic acid), acetylenic fatty acids (crepenynic acid) and hydroxy fatty acids (ricinoleic acid) may be used as inhibitors. Analogs such as α-elostearic acid with conjugated double bonds may be acceptable inhibitors. These may be expressed in plants (e.g. a Δ12 epoxygenase from *C. palaestina* produces vernolic acid in transgenic *Arabidopsis* (Singh et. al., supra).

Compounds can also act by allosteric inhibition or by preventing the fatty acid desaturase from binding to, and thus, acting on its target, i.e., a fatty acid.

A high-throughput method can be used to screen large libraries of chemicals. Such libraries of candidate compounds can be generated or purchased, e.g., from Chembridge Corp. (San Diego, Calif.). Libraries can be designed to cover a diverse range of compounds. For example, a library can include 10,000, 50,000, or 100,000 or more unique compounds. Merely by way of illustration, a library can be constructed from heterocycles including pyridines, indoles, quinolines, furans, pyrimidines, triazines, pyrroles, imidazoles, naphthalenes, benzimidazoles, piperidines, pyrazoles, benzoxazoles, pyrrolidines, thiphenes, thiazoles, benzothiazoles, and morpholines. It may be cyclypropenoid analogs of linoleic acid, epoxy fatty acids (vernolic acid), acetylenic fatty acids (crepenynic acid), and/or hydroxy fatty acids (ricinoleic acid). Analogs such as α-elostearic acid with conjugated double bonds may be acceptable inhibitors. A library can be designed and synthesized to cover such classes of chemicals, e.g., as described in DeWitt et al. (1993) *Proc. Natl. Acad. Sci. U.S.A.* 90:6909; Erb et al. (1994) *Proc. Natl. Acad. Sci. USA,* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Organism-based Assays: Organisms can be grown in microtiter plates, e.g., 6-well, 32-well, 64-well, 96-well, 384-well plates. In one embodiment, the organism is a nematode. The nematodes can be genetically modified. Non-limiting examples of such modified nematodes include: 1) nematodes or nematode cells (*M. incognita, H. glycines, D. immitis, S. stercoralis, R. axei*, and/or *C. elegans*) having one or more fatty acid desaturase-like genes inactivated (e.g., using RNA mediated interference); 2) nematodes or nematode cells expressing a heterologous fatty acid desaturase-like gene, e.g., a fatty acid desaturase-like gene from another species; and 3) nematodes or nematode cells having one or more endogenous fatty acid desaturase-like genes inactivated and expressing a heterologous fatty acid desaturase-like gene, e.g., a *M. incognita, H. glycines, D. immitis, S. stercoralis* or *R. axei* fatty acid desaturase-like gene as described herein.

A plurality of candidate compounds, e.g., a combinatorial library, can be screened. The library can be provided in a format that is amenable for robotic manipulation, e.g., in microtitre plates. Compounds can be added to the wells of the microtiter plates. Following compound addition and incubation, viability and/or reproductive properties of the nematodes or nematode cells are monitored.

The compounds can also be pooled, and the pools tested. Positive pools are split for subsequent analysis. Regardless of the method, compounds that decrease the viability or reproductive ability of nematodes, nematode cells, or progeny of the nematodes are considered lead compounds.

In another embodiment, the compounds can be tested on a microorganism, (e.g., a yeast and/or bacterium). For example, a *M. incognita, H. glycines, D. immitis, S. stercoralis* or *R. axei* fatty acid desaturase gene can be expressed in *S. cerevisiae*, as has been described for a *C. elegans* FAT-2 like polypeptide (Peyo-Ndi (2000) *Archives of Biochem and Biophysics* 376: 399–408). The generation of such strains is routine in the art. As described above for nematodes and nematode cells, the cell lines can be grown in microtitre plates, each well having a different candidate compound or pool of candidate compounds. Growth is monitored during or after the assay to determine if the compound or pool of compounds is a modulator of a nematode fatty acid desaturase-like polypeptide.

In another embodiment fatty acid composition of the organisms can be determined, using, for example, GC-MS. Fatty acid methyl esters can be formed by a transesterification reaction and extracted. GC-MS can be performed using a Hewlet Packard 6890 gas chromatograph interfaced with a Hewlet Packard 5973 mass selective detector, for example. Retention times of resulting methyl esters can be compared with those of known samples (Cahoon, supra). In another embodiment, ethyl esters can be extracted with hexane and analyzed by GLC through a 50 m by 0.32 mm CP-Wax58-CB fused silica column (Chrompack) (Singh, supra; Lee, supra). In another embodiment, if a *M. incognita, H. glycines, D. immitis, S. stercoralis* or *R. axei* fatty acid desaturase gene is expressed in a microorganism (i.e., yeast), fatty acid methyl esters can be prepared using methanolic HCl as described (Reed et al. (2000) *Plant Physiol.* 122:715–720; Meesapyodsuk, (2000) Biochemistry 39:11948–11954).

In Vitro Activity Assays: The screening assay can be an in vitro activity assay. For example, a nematode fatty acid desaturase-like polypeptide can be purified as described above. The polypeptide can be disposed in an assay container, e.g., a well of a microtitre plate along with an appropriate substrate. A candidate compound can be added to the assay container, and the fatty acid desaturase-like activity is measured. Optionally, the activity is compared to the activity measured in a control container in which no candidate compound is disposed or in which an inert or non-functional compound is disposed. Fatty acid composition can be determined, using, for example, GC-MS. Fatty acid methyl esters can be formed by a transesterification reaction and extracted. GC-MS can be performed using a Hewlet Packard 6890 gas chromatograph interfaced with a Hewlet Packard 5973 mass selective detector, for example. Retention times of resulting methyl esters can be compared with those of known samples (Cahoon, supra). In another embodiment, ethyl esters can be extracted with hexane and analyzed by GLC through a 50 m by 0.32 mm CP-Wax58-CB fused silica column (Chrompack) (Singh, supra; Lee, supra).

In Vitro Binding Assays: The screening assay can also be a cell-free binding assay, e.g., an assay to identify compounds that bind a nematode fatty acid desaturase-like polypeptide. For example, a nematode fatty acid desaturase-like polypeptide can be purified and labeled. The labeled polypeptide is contacted to beads; each bead has a tag detectable by mass spectroscopy, and test compound, e.g., a compound synthesized by combinatorial chemical methods. Beads to which the labeled polypeptide is bound are identified and analyzed by mass spectroscopy. The beads can be generated using "split-and-pool" synthesis. The method can further include a second assay to determine if the compound alters the activity of the fatty acid desaturase-like polypeptide.

Optimization of a Compound: Once a lead compound has been identified, standard principles of medicinal chemistry can be used to produce derivatives of the compound. Derivatives can be screened for improved pharmacological properties, for example, efficacy, pharmacokinetics, stability, solubility, and clearance. The moieties responsible for a compound's activity in the above-described assays can be delineated by examination of structure-activity relationships (SAR) as is commonly practiced in the art. One can modify moieties on a lead compound and measure the effects of the modification on the efficacy of the compound to thereby produce derivatives with increased potency. For an example, see Nagarajan et al. (1988) *J. Antibiot.* 41:1430–8. A modification can include N-acylation, amination, amidation, oxidation, reduction, alkylation, esterification, and hydroxylation. Furthermore, if the biochemical target of the lead compound is known or determined, the structure of the target and the lead compound can inform the design and optimization of derivatives. Molecular modeling software is commercially available (e.g., Molecular Simulations, Inc.). "SAR by NMR," as described in Shuker et al. (1996) *Science* 274:1531–4, can be used to design ligands with increased affinity, by joining lower-affinity ligands.

A preferred compound is one that interferes with the function of a fatty acid desaturase-like polypeptide and that is not substantially toxic to plants, animals, or humans. By "not substantially toxic" it is meant that the compound does not substantially affect the respective animal, or human fatty acid desaturase proteins or fatty acid desaturase activity. Thus, particularly desirable inhibitors of *M. incognita, H. glycines, D. immitis, S. stercoralis* or *R. axei* fatty acid desaturase do not substantially inhibit fatty acid desaturase-like polypeptides or fatty acid desaturase activity of vertebrates, e.g., humans for example. Other desirable compounds do not substantially inhibit to fatty acid desaturase activity of plants.

Standard pharmaceutical procedures can be used to assess the toxicity and therapeutic efficacy of a modulator of a fatty acid desaturase-like activity. The LD50 (the dose lethal to 50% of the population) and the ED50 (the dose therapeutically effective in 50% of the population can be measured in cell cultures, experimental plants (e.g., in laboratory or field studies), or experimental animals. Optionally, a therapeutic index can be determined which is expressed as the ratio: LD50/ED50. High therapeutic indices are indicative of a compound being an effective fatty acid desaturase-like inhibitor, while not causing undue toxicity or side-effects to a subject (e.g., a host plant or host animal).

Alternatively, the ability of a candidate compound to modulate a non-nematode fatty acid desaturase-like polypeptide is assayed, e.g., by a method described herein. For example, the inhibition constant of a candidate compound for a mammalian fatty acid desaturase-like polypeptide can be measured and compared to the inhibition constant for a nematode fatty acid desaturase-like polypeptide.

The aforementioned analyses can be used to identify and/or design a modulator with specificity for nematode fatty acid desaturase-like polypeptide over vertebrate or other animal (e.g., mammalian) fatty acid desaturase-like polypeptides. Suitable nematodes to target are any nematodes with the fatty acid desaturase-like proteins or proteins that can be targeted by a compound that otherwise inhibits, reduces, activates, or generally affects the activity of nematode fatty acid desaturase proteins.

Inhibitors of nematode fatty acid desaturase-like proteins can also be used to identify fatty acid desaturase-like proteins in the nematode or other organisms using procedures known in the art, such as affinity chromatography. For example, a specific antibody may be linked to a resin and a nematode extract passed over the resin, allowing any fatty acid desaturase-like proteins that bind the antibody to bind the resin. Subsequent biochemical techniques familiar to those skilled in the art can be performed to purify and identify bound fatty acid desaturase-like proteins.

Agricultural Compositions

A compound that is identified as a fatty acid desaturase-like polypeptide inhibitor can be formulated as a composition that is applied to plants, soil, or seeds in order to confer nematode resistance. The composition can be prepared in a solution, e.g., an aqueous solution, at a concentration from about 0.005% to 10%, or about 0.01% to 1%, or about 0.1% to 0.5% by weight. The solution can include an organic solvent, e.g., glycerol or ethanol. The composition can be formulated with one or more agriculturally acceptable carriers. Agricultural carriers can include: clay, talc, bentonite, diatomaceous earth, kaolin, silica, benzene, xylene, toluene, kerosene, N-methylpyrrolidone, alcohols (methanol, ethanol, isopropanol, n-butanol, ethylene glycol, propylene glycol, and the like), and ketones (acetone, methylethyl ketone, cyclohexanone, and the like). The formulation can optionally further include stabilizers, spreading agents, wetting extenders, dispersing agents, sticking agents, disintegrators, and other additives, and can be prepared as a liquid, a water-soluble solid (e.g., tablet, powder or granule), or a paste.

Prior to application, the solution can be combined with another desired composition such as another anthelmintic agent, germicide, fertilizer, plant growth regulator and the like. The solution may be applied to the plant tissue, for example, by spraying, e.g., with an atomizer, by drenching, by pasting, or by manual application, e.g., with a sponge. The solution can also be distributed from an airborne source, e.g., an aircraft or other aerial object, e.g., a fixture mounted with an apparatus for spraying the solution, the fixture being of sufficient height to distribute the solution to the desired plant tissues. Alternatively, the composition can be applied to plant tissue from a volatile or airborne source. The source is placed in the vicinity of the plant tissue and the composition is dispersed by diffusion through the atmosphere. The source and the plant tissue to be contacted can be enclosed in an incubator, growth chamber, or greenhouse, or can be in sufficient proximity that they can be outdoors.

If the composition is distributed systemically thorough the plant, the composition can be applied to tissues other than the leaves, e.g., to the stems or roots. Thus, the composition can be distributed by irrigation. The composition can also be injected directly into roots or stems.

A skilled artisan would be able to determine an appropriate dosage for formulation of the active ingredient of the composition. For example, the ED50 can be determined as described above from experimental data. The data can be obtained by experimentally varying the dose of the active ingredient to identify a dosage effective for killing a nematode, while not causing toxicity in the host plant or host animal (i.e. non-nematode animal).

A number of embodiments of the invention have been described. Nevertheless, it will be understood that various modifications may be made without departing from the spirit and scope of the invention. Accordingly, other embodiments are within the scope of the following claims.

What is claimed is:

1. A purified polypeptide comprising an amino acid sequence that is at least 95% identical to the amino acid sequence of SEQ ID NO: 9, wherein the polypeptide has fatty acid desaturase activity.

2. The purified polypeptide of claim 1, wherein the amino acid sequence is at least 98% identical to the amino acid sequence of SEQ ID NO: 9.

3. A purified polypeptide comprising the amino acid sequence of SEQ ID NO: 9.

* * * * *

SEQUENCE LISTING

```
<160> NUMBER OF SEQ ID NOS: 32

<210> SEQ ID NO 1
<211> LENGTH: 1194
<212> TYPE: DNA
<213> ORGANISM: Meloidogyne incognita
<220> FEATURE:
<221> NAME/KEY: CDS
<222> LOCATION: (1)...(1191)

<400> SEQUENCE: 1 atg tct tat ctt gac aca acc aaa aat aat tta aac aat ggg gga tcc       48
Met Ser Tyr Leu Asp Thr Thr Lys Asn Asn Leu Asn Asn Gly Gly Ser
 1               5                  10                  15 aat gat aat ggc aat gct ttt tgc aat gat aat gat ttt gtt ggt aat       96
Asn Asp Asn Gly Asn Ala Phe Cys Asn Asp Asn Asp Phe Val Gly Asn
            20                  25                  30 aat gct gaa tct gtg gtt agt aat gtg gcg gca cct aat gtc gag gaa      144
Asn Ala Glu Ser Val Val Ser Asn Val Ala Ala Pro Asn Val Glu Glu
        35                  40                  45 ttg cga atg tcc gtg cca cca gaa tgc ttc gaa aaa ccc tta att cgt      192
Leu Arg Met Ser Val Pro Pro Glu Cys Phe Glu Lys Pro Leu Ile Arg
    50                  55                  60 tcg atc tct tat tta att ttg gat ttg gta att att tct ggt ctt tat      240
Ser Ile Ser Tyr Leu Ile Leu Asp Leu Val Ile Ile Ser Gly Leu Tyr
```

-continued

| | |
|---|---|
| atg gtt gtt gga att gtt gaa aat tat ttg gga ttt gtt gga ctt tta<br>Met Val Val Gly Ile Val Glu Asn Tyr Leu Gly Phe Val Gly Leu Leu<br>65               70               75               80 | 288 |
| att tgg tat tgg gtt ctc gga atg tat tta tcc tct tta ttt tgt att<br>Ile Trp Tyr Trp Val Leu Gly Met Tyr Leu Ser Ser Leu Phe Cys Ile<br>                   100                 105                 110 | 336 |
| ggg cat gat tgt ggg cac gga act ttt tct tcc tat act tgg gtg aat<br>Gly His Asp Cys Gly His Gly Thr Phe Ser Ser Tyr Thr Trp Val Asn<br>            115                120                125 | 384 |
| gat ttg ttt ggg cat att tct cat gct gtt att atg gtt cca ttc tgg<br>Asp Leu Phe Gly His Ile Ser His Ala Val Ile Met Val Pro Phe Trp<br>130                   135                140 | 432 |
| ccc tgg caa aaa tca cat cga caa cac cat caa tac acg gca cat ttg<br>Pro Trp Gln Lys Ser His Arg Gln His His Gln Tyr Thr Ala His Leu<br>145                   150                155                160 | 480 |
| gat aaa gat aaa gga cac cct tgg gtt aca gaa gag gag tat gaa tca<br>Asp Lys Asp Lys Gly His Pro Trp Val Thr Glu Glu Glu Tyr Glu Ser<br>                   165                 170                175 | 528 |
| agt aat tgg att aaa aaa cat ttt gcc aaa att cct tta tct gga ctt<br>Ser Asn Trp Ile Lys Lys His Phe Ala Lys Ile Pro Leu Ser Gly Leu<br>            180                185                190 | 576 |
| att cgt tgg aac cca ata tac aca att gct gga ctc ccc gat ggt tct<br>Ile Arg Trp Asn Pro Ile Tyr Thr Ile Ala Gly Leu Pro Asp Gly Ser<br>                   195                 200                205 | 624 |
| cat ttt tgg ccg tgg tct aaa tta ttt gag aat aat gtt gat aga att<br>His Phe Trp Pro Trp Ser Lys Leu Phe Glu Asn Asn Val Asp Arg Ile<br>210                   215                220 | 672 |
| aaa tgt gtt gtt agt gtt tct gct tgt ttt cta tgc tct ttt gtt att<br>Lys Cys Val Val Ser Val Ser Ala Cys Phe Leu Cys Ser Phe Val Ile<br>225                   230                235                240 | 720 |
| ctc tac tat atg aat tat aat ttg tgg aac ttt ttt aaa tat tat tat<br>Leu Tyr Tyr Met Asn Tyr Asn Leu Trp Asn Phe Phe Lys Tyr Tyr Tyr<br>                   245                 250                255 | 768 |
| gtg ccg tta atg ttc caa ggt ttc tgg atg gtc ata ata acc ttt tta<br>Val Pro Leu Met Phe Gln Gly Phe Trp Met Val Ile Ile Thr Phe Leu<br>260                   265                270 | 816 |
| caa cat caa gac gag caa att gaa gtt tat gaa gaa ggg act tgg gca<br>Gln His Gln Asp Glu Gln Ile Glu Val Tyr Glu Glu Gly Thr Trp Ala<br>            275                280                285 | 864 |
| ttt atg aaa ggg cag tta cag act gtt gat aga tct ttt gga ttt gga<br>Phe Met Lys Gly Gln Leu Gln Thr Val Asp Arg Ser Phe Gly Phe Gly<br>290                   295                300 | 912 |
| ata gac aaa gca ttg cat cac ata act gac ggt cat gta gcc cat cat<br>Ile Asp Lys Ala Leu His His Ile Thr Asp Gly His Val Ala His His<br>305                   310                315                320 | 960 |
| ttc ttt ttt act cgt att cct cat tat aat tta cct aaa gct acg gaa<br>Phe Phe Phe Thr Arg Ile Pro His Tyr Asn Leu Pro Lys Ala Thr Glu<br>                   325                 330                335 | 1008 |
| gct gtt aaa aag gtt ttg caa aaa tac cct ggc gca tat aaa cat aaa<br>Ala Val Lys Lys Val Leu Gln Lys Tyr Pro Gly Ala Tyr Lys His Lys<br>            340                345                350 | 1056 |
| agt gca tat gac ttt tta att aaa ttt tta tgg tta aat att aaa ttg<br>Ser Ala Tyr Asp Phe Leu Ile Lys Phe Leu Trp Leu Asn Ile Lys Leu<br>                   355                 360                365 | 1104 |
| gac tgt ctt gtt ggt aaa ggt agc ggt tta ctt aaa tat cgt tct act<br>Asp Cys Leu Val Gly Lys Gly Ser Gly Leu Leu Lys Tyr Arg Ser Thr<br>370                   375                380 | 1152 |
| gtc cag aat gat gaa caa ctt aat aat aaa aag gat aaa tag | 1194 |

```
Val Gln Asn Asp Glu Gln Leu Asn Asn Lys Lys Asp Lys
385                 390                 395

<210> SEQ ID NO 2
<211> LENGTH: 1242
<212> TYPE: DNA
<213> ORGANISM: Meloidogyne incognita
<220> FEATURE:
<221> NAME/KEY: CDS
<222> LOCATION: (1)...(1239)

<400> SEQUENCE: 2 atg tct tat att gac aca acc aaa aat aat tta ata aac aat ggt gga      48
Met Ser Tyr Ile Asp Thr Thr Lys Asn Asn Leu Ile Asn Asn Gly Gly
 1               5                  10                  15 tac aat ccc ggc aat att aat gac gat ggc agc agt tct tat cgt ctt      96
Tyr Asn Pro Gly Asn Ile Asn Asp Asp Gly Ser Ser Ser Tyr Arg Leu
             20                  25                  30 ttc aat gat gac agc aaa tct gaa ttt tat ggt ggc aat gct gaa tct     144
Phe Asn Asp Asp Ser Lys Ser Glu Phe Tyr Gly Gly Asn Ala Glu Ser
         35                  40                  45 gcg tct tca aat atc gga gtt ttt aga caa gta cca aac gtt gag gaa     192
Ala Ser Ser Asn Ile Gly Val Phe Arg Gln Val Pro Asn Val Glu Glu
     50                  55                  60 ttg cga atg tca gtg ccc cca gaa tgt ttt gac aag cct tta att cgt     240
Leu Arg Met Ser Val Pro Pro Glu Cys Phe Asp Lys Pro Leu Ile Arg
 65                  70                  75                  80 tca att tct tat tta att ctg gat ttg gta att att tct ggt ctt tat     288
Ser Ile Ser Tyr Leu Ile Leu Asp Leu Val Ile Ile Ser Gly Leu Tyr
                 85                  90                  95 atg gtt gtt gga att gtt gaa aat tat ttg gga ttt gtt gga ctt tta     336
Met Val Val Gly Ile Val Glu Asn Tyr Leu Gly Phe Val Gly Leu Leu
            100                 105                 110 att tgg tat tgg gtt ctc gga atg tat tta tcc tct tta ttt tgt att     384
Ile Trp Tyr Trp Val Leu Gly Met Tyr Leu Ser Ser Leu Phe Cys Ile
        115                 120                 125 ggg cat gat tgt ggg cac gga act ttt tct tcc tat act tgg gtg aat     432
Gly His Asp Cys Gly His Gly Thr Phe Ser Ser Tyr Thr Trp Val Asn
    130                 135                 140 gat ttg ttt ggg cat att tct cat gct gtt att atg gtt cca ttc tgg     480
Asp Leu Phe Gly His Ile Ser His Ala Val Ile Met Val Pro Phe Trp
145                 150                 155                 160 ccc tgg caa aaa tca cat cga caa cac cat caa tac acg gca cat ttg     528
Pro Trp Gln Lys Ser His Arg Gln His His Gln Tyr Thr Ala His Leu
                165                 170                 175 gat aaa gat aaa gga cac cct tgg gtt aca gaa gag gag tat gaa tca     576
Asp Lys Asp Lys Gly His Pro Trp Val Thr Glu Glu Glu Tyr Glu Ser
            180                 185                 190 agt aat tgg att aaa aaa cat ttt gcc aaa att cct tta tct gga ctt     624
Ser Asn Trp Ile Lys Lys His Phe Ala Lys Ile Pro Leu Ser Gly Leu
        195                 200                 205 att cgt tgg aac cca ata tac acg att gct gga ctc ccc gat ggt tct     672
Ile Arg Trp Asn Pro Ile Tyr Thr Ile Ala Gly Leu Pro Asp Gly Ser
    210                 215                 220 cat ttt tgg ccg tgg tct aaa tta ttt gaa aat aat gtt gat aga att     720
His Phe Trp Pro Trp Ser Lys Leu Phe Glu Asn Asn Val Asp Arg Ile
225                 230                 235                 240 aaa tgt gtt gtt agt gtt tct gct tgt ttt cta tgc tct ttt gtt att     768
Lys Cys Val Val Ser Val Ser Ala Cys Phe Leu Cys Ser Phe Val Ile
                245                 250                 255 ctc tac tat atg aat tat aat ttg tgg aac ttt ttt aaa tat tat tat     816
```

-continued

```
Leu Tyr Tyr Met Asn Tyr Asn Leu Trp Asn Phe Phe Lys Tyr Tyr Tyr
                260                 265                 270 gtg ccg tta atg ttc caa ggt ttc tgg atg gtc ata ata acc ttt tta      864
Val Pro Leu Met Phe Gln Gly Phe Trp Met Val Ile Ile Thr Phe Leu
            275                 280                 285 caa cac caa gac gaa caa att gag gtt tat gaa gaa ggg act tgg gca      912
Gln His Gln Asp Glu Gln Ile Glu Val Tyr Glu Glu Gly Thr Trp Ala
        290                 295                 300 ttt atg aaa ggg cag tta cag act gtt gat aga tct ttt gga ttt gga      960
Phe Met Lys Gly Gln Leu Gln Thr Val Asp Arg Ser Phe Gly Phe Gly
305                 310                 315                 320 ata gac aaa gca ttg cat cac ata act gac ggt cat gta gcc cat cat     1008
Ile Asp Lys Ala Leu His His Ile Thr Asp Gly His Val Ala His His
                325                 330                 335 ttc ttt ttt act cgt att cct cat tat aat tta cct aaa gct acg gaa     1056
Phe Phe Phe Thr Arg Ile Pro His Tyr Asn Leu Pro Lys Ala Thr Glu
            340                 345                 350 gct gtt aaa aag gtt ttg caa aaa tac cct ggc gca tat aaa cat aaa     1104
Ala Val Lys Lys Val Leu Gln Lys Tyr Pro Gly Ala Tyr Lys His Lys
        355                 360                 365 agt gca tat gac ttt tta att aaa ttt tta tgg tta aat att aaa ttg     1152
Ser Ala Tyr Asp Phe Leu Ile Lys Phe Leu Trp Leu Asn Ile Lys Leu
370                 375                 380 gac tgt ctt gtt ggt aaa ggt agc ggt tta ctt aaa tat cgt tct act     1200
Asp Cys Leu Val Gly Lys Gly Ser Gly Leu Leu Lys Tyr Arg Ser Thr
                385                 390                 395                 400 gtc cag aat gat gaa caa ctt aat aat aaa aag gat aaa tag             1242
Val Gln Asn Asp Glu Gln Leu Asn Asn Lys Lys Asp Lys
            405                 410

<210> SEQ ID NO 3
<211> LENGTH: 1260
<212> TYPE: DNA
<213> ORGANISM: Meloidogyne incognita
<220> FEATURE:
<221> NAME/KEY: CDS
<222> LOCATION: (1)...(1161)

<400> SEQUENCE: 3 atg tcc cta att tca tca aat aca att gtt gaa aca act aaa aca aat       48
Met Ser Leu Ile Ser Ser Asn Thr Ile Val Glu Thr Thr Lys Thr Asn
1               5                   10                  15 gga aat aca att tct gat tct aac aac aaa att aat tat tcc ttc cct      96
Gly Asn Thr Ile Ser Asp Ser Asn Asn Lys Ile Asn Tyr Ser Phe Pro
            20                  25                  30 aat tta aat gaa ctt cga aat gcg atc cca gca gag tgt ttt gaa aaa     144
Asn Leu Asn Glu Leu Arg Asn Ala Ile Pro Ala Glu Cys Phe Glu Lys
        35                  40                  45 tct cta att cgt tca ctt tct tat tta att ttg gat ttt tta att att     192
Ser Leu Ile Arg Ser Leu Ser Tyr Leu Ile Leu Asp Phe Leu Ile Ile
    50                  55                  60 tat gga ctt tat ttg gtt gtt ggg gtt gtt gag gac aac ttt ggg att     240
Tyr Gly Leu Tyr Leu Val Val Gly Val Val Glu Asp Asn Phe Gly Ile
65                  70                  75                  80 att gga ctt ttg ctt tgg tat tgg gta tta ggt atg ttt tta ttc tct     288
Ile Gly Leu Leu Leu Trp Tyr Trp Val Leu Gly Met Phe Leu Phe Ser
                85                  90                  95 ata ttc gct gtt gga cac gat tgt ggg cac gga act ttt tct tcc tat     336
Ile Phe Ala Val Gly His Asp Cys Gly His Gly Thr Phe Ser Ser Tyr
            100                 105                 110 act tgg gta aat gat ttg ttt ggg cat gtg gca cat gct cct act atg     384
```

```
Thr Trp Val Asn Asp Leu Phe Gly His Val Ala His Ala Pro Thr Met
        115                 120                 125 gtc cct tat tgg cct tgg caa aaa tcc cat aga tta cac cat caa tac    432
Val Pro Tyr Trp Pro Trp Gln Lys Ser His Arg Leu His His Gln Tyr
130                 135                 140 act gca cat ttg gat aaa gat atg agt cat cct tgg ata cct gaa aag    480
Thr Ala His Leu Asp Lys Asp Met Ser His Pro Trp Ile Pro Glu Lys
145                 150                 155                 160 ctt tat tta tct tta aat tgg ata tcc aaa cat tat ctc aaa ttt cct    528
Leu Tyr Leu Ser Leu Asn Trp Ile Ser Lys His Tyr Leu Lys Phe Pro
                165                 170                 175 ttg act ggg ttt gtt agt tgg att cca tta tat aca ata ttt ggt att    576
Leu Thr Gly Phe Val Ser Trp Ile Pro Leu Tyr Thr Ile Phe Gly Ile
            180                 185                 190 ccc gat ggt tct cat ttt tgg cct tgg tct aaa tta ttt gaa aac aat    624
Pro Asp Gly Ser His Phe Trp Pro Trp Ser Lys Leu Phe Glu Asn Asn
        195                 200                 205 act gat aga att aaa tgt gct gtt agt gtt gct gct tgt ttt cta tgt    672
Thr Asp Arg Ile Lys Cys Ala Val Ser Val Ala Ala Cys Phe Leu Cys
210                 215                 220 gcc tat ata gct tta tat tgt tca aat tat aat tta tgg ata ttt ttt    720
Ala Tyr Ile Ala Leu Tyr Cys Ser Asn Tyr Asn Leu Trp Ile Phe Phe
225                 230                 235                 240 aaa tat tat tat att ccg gtt atg ttc caa ggt ttc tgg tta gtt ttg    768
Lys Tyr Tyr Tyr Ile Pro Val Met Phe Gln Gly Phe Trp Leu Val Leu
                245                 250                 255 att act tat tta caa cac cat gac gaa gag act gaa gtt tat gaa gat    816
Ile Thr Tyr Leu Gln His His Asp Glu Glu Thr Glu Val Tyr Glu Asp
            260                 265                 270 gga acg tgg ggg ttt gtg aga ggg cag tta cag aca gtt gat aga tct    864
Gly Thr Trp Gly Phe Val Arg Gly Gln Leu Gln Thr Val Asp Arg Ser
        275                 280                 285 ttt gga ttt gga ata gac aaa gca ttg cat aac ata act gac ggt cat    912
Phe Gly Phe Gly Ile Asp Lys Ala Leu His Asn Ile Thr Asp Gly His
290                 295                 300 gta gcc cat cac ctc ttt ttt acg cgt att cca cat tac aat tta ccc    960
Val Ala His His Leu Phe Phe Thr Arg Ile Pro His Tyr Asn Leu Pro
305                 310                 315                 320 aaa gct act gaa gca gtt aaa aga ata tta acg gaa aaa tac ccg gga   1008
Lys Ala Thr Glu Ala Val Lys Arg Ile Leu Thr Glu Lys Tyr Pro Gly
                325                 330                 335 aca tat aaa tac aaa aaa tcc tat gac ttt tta att gaa ttt ttg tgg   1056
Thr Tyr Lys Tyr Lys Lys Ser Tyr Asp Phe Leu Ile Glu Phe Leu Trp
            340                 345                 350 tta aat att aaa ctg gat tac ctt gtt gga aaa ggt agt ggt tta ctt   1104
Leu Asn Ile Lys Leu Asp Tyr Leu Val Gly Lys Gly Ser Gly Leu Leu
        355                 360                 365 aga tat cga aat aat atc cgg act aat gac caa tct aaa aca aca aaa   1152
Arg Tyr Arg Asn Asn Ile Arg Thr Asn Asp Gln Ser Lys Thr Thr Lys
370                 375                 380 aag aat aat taagacttta atattctcga tgtttttcat tttgttgaat           1201
Lys Asn Asn
385 tttatttttt ctttaattta aatataaaaa ttatttactt aaaaaaaaaa aaaaaaaag  1260
```

<210> SEQ ID NO 4
<211> LENGTH: 1488
<212> TYPE: DNA

```
<221> NAME/KEY: CDS
<222> LOCATION: (85)...(1251)

<400> SEQUENCE: 4
gtttaattac ccaagtttga aacctttgcc gtccctgct ccattttctt ttcctcctcc      60
ttttcatcac attttcgcct cctc atg tcc cct ccc tgc tcc ttt tcc cct     111
                          Met Ser Pro Pro Cys Ser Phe Ser Pro
                            1               5 tcc tcc gcc tcc tct tcc cct gac agt ccc tca gca gaa ggc caa gcc     159
Ser Ser Ala Ser Ser Ser Pro Asp Ser Pro Ser Ala Glu Gly Gln Ala
 10                  15                  20                  25 cag caa aat ggc caa gtt ttg gcc ccc cgt cca ttg ccc acg tgg gag     207
Gln Gln Asn Gly Gln Val Leu Ala Pro Arg Pro Leu Pro Thr Trp Glu
                 30                  35                  40 gaa atc cgt gcc gcg gtg ccc aaa gag tgt ttt gaa aag tct ctc ctt     255
Glu Ile Arg Ala Ala Val Pro Lys Glu Cys Phe Glu Lys Ser Leu Leu
             45                  50                  55 cgt tct ctg tac tat ttg gcc atc gat ttg ctc gtc att ggc ttc ctt     303
Arg Ser Leu Tyr Tyr Leu Ala Ile Asp Leu Leu Val Ile Gly Phe Leu
         60                  65                  70 tac gcc gtt gtg cct ttt gta gag aca aat ttc gga ctg atc gga ctg     351
Tyr Ala Val Val Pro Phe Val Glu Thr Asn Phe Gly Leu Ile Gly Leu
 75                  80                  85 ttt ttc tgg tac tgc ttg ctc ggc atg ttt ttg tcc tct ctg ttt tgc     399
Phe Phe Trp Tyr Cys Leu Leu Gly Met Phe Leu Ser Ser Leu Phe Cys
 90                  95                 100                 105 gtt ggc cat gac tgc ggc cac ggc act ttt tcc gat tgg aca tgg gtc     447
Val Gly His Asp Cys Gly His Gly Thr Phe Ser Asp Trp Thr Trp Val
                110                 115                 120 aac gac att ttc ggc cat att tcc cac gct ttg cta atg gtg ccc ttt     495
Asn Asp Ile Phe Gly His Ile Ser His Ala Leu Leu Met Val Pro Phe
            125                 130                 135 tgg cca tgg caa aaa agc cac cgt caa cat cac caa ttc act tct cat     543
Trp Pro Trp Gln Lys Ser His Arg Gln His His Gln Phe Thr Ser His
        140                 145                 150 gtg gac aag gac aaa ggt cat ccc tgg gtg ttg gaa gat gac tac gaa     591
Val Asp Lys Asp Lys Gly His Pro Trp Val Leu Glu Asp Asp Tyr Glu
    155                 160                 165 ggt ggc gga tgg ctg cga aaa cat ttt gct aag att ccc ttg tcc gga     639
Gly Gly Gly Trp Leu Arg Lys His Phe Ala Lys Ile Pro Leu Ser Gly
170                 175                 180                 185 ctg atc agg tgg aat ccc att tac act gtc gcc ggt ctc ccc gac ggc     687
Leu Ile Arg Trp Asn Pro Ile Tyr Thr Val Ala Gly Leu Pro Asp Gly
                190                 195                 200 tcc cat ttt tgg ccc ttt tct cgg ctg ttc tcc aac aat aca gag cgt     735
Ser His Phe Trp Pro Phe Ser Arg Leu Phe Ser Asn Asn Thr Glu Arg
            205                 210                 215 ttc aaa tgt ctg atc agt tcc tca ctt tgt ctt atc act tct tgg gcc     783
Phe Lys Cys Leu Ile Ser Ser Ser Leu Cys Leu Ile Thr Ser Trp Ala
        220                 225                 230 att ttc gtt ttg ctt gac cac agt ccg tgg gcc ttt ctc aaa tat tat     831
Ile Phe Val Leu Leu Asp His Ser Pro Trp Ala Phe Leu Lys Tyr Tyr
    235                 240                 245 tat gtg ccg ctg atg ttt cag ggc tat tgg atg gtg atc atc aca tat     879
Tyr Val Pro Leu Met Phe Gln Gly Tyr Trp Met Val Ile Ile Thr Tyr
250                 255                 260                 265 ttg caa cat cag gac gag caa atc gag gtg tac gag gag ggc aat tgg     927
Leu Gln His Gln Asp Glu Gln Ile Glu Val Tyr Glu Glu Gly Asn Trp
                270                 275                 280
```

```
gca ttt gtc aag gga cag ctg cag acg tac gat cgc gag tac ggt ttt      975
Ala Phe Val Lys Gly Gln Leu Gln Thr Tyr Asp Arg Glu Tyr Gly Phe
            285                 290                 295 ggc att gat cac gcc atg cat cac att acg gat ggt cac gtg gcg cac     1023
Gly Ile Asp His Ala Met His His Ile Thr Asp Gly His Val Ala His
        300                 305                 310 cat ttc ttc ttc acc cga atc cct cat tat cat ttg cct gag gca acc     1071
His Phe Phe Phe Thr Arg Ile Pro His Tyr His Leu Pro Glu Ala Thr
    315                 320                 325 aaa agc att cgc aaa att atg gaa aaa tac ccg ggg gcg tac aag cgc     1119
Lys Ser Ile Arg Lys Ile Met Glu Lys Tyr Pro Gly Ala Tyr Lys Arg
330                 335                 340                 345 aag tca aac tac gac ttt ctg ctc caa ttt ctg tgg atg aac gtc aaa     1167
Lys Ser Asn Tyr Asp Phe Leu Leu Gln Phe Leu Trp Met Asn Val Lys
                350                 355                 360 ttg gac tgt ttg gtg ggg aaa ggc agc gga ctg ttg aag tat cgg aca     1215
Leu Asp Cys Leu Val Gly Lys Gly Ser Gly Leu Leu Lys Tyr Arg Thr
            365                 370                 375 acg gca cga agg gaa gag agg cag caa aag gag gac taagaaacag          1261
Thr Ala Arg Arg Glu Glu Arg Gln Gln Lys Glu Asp
        380                 385 gagggaggtc aacgacaga acagagagga tgagaggga aaagaaacga gacggaaggg     1321
cgagagacac agaggaagga aaggcgaaaa gaaaaagaaa agtgcaaata tttattaaac   1381
aattaattta ataaatgaaa cacagtttat tgctgttgtt gttatttaaa agtgaatgaa   1441
tgaatacggt ggaaaaaaaa aaaaaaaagt actagtcgac gcgtggc                 1488

<210> SEQ ID NO 5
<211> LENGTH: 1068
<212> TYPE: DNA
<213> ORGANISM: Dirofilaria immitis
<220> FEATURE:
<221> NAME/KEY: CDS
<222> LOCATION: (1)...(867)

<400> SEQUENCE: 5 tat tgt tgc atg ggg atg ttc ggg tca tca ttg ttt gtg gtt ggc cat       48
Tyr Cys Cys Met Gly Met Phe Gly Ser Ser Leu Phe Val Val Gly His
1               5                   10                  15 gat tgt gga cat ggt aca ttt tcc gaa tat acg tgg gtc aac gat ttt       96
Asp Cys Gly His Gly Thr Phe Ser Glu Tyr Thr Trp Val Asn Asp Phe
            20                  25                  30 ttc gga cat att gct cat gct tca ctt ttg gta ccg tat tgg cct tgg      144
Phe Gly His Ile Ala His Ala Ser Leu Leu Val Pro Tyr Trp Pro Trp
        35                  40                  45 caa aag tct cat aga cta cat cat cag tac act tct cat att gac aat      192
Gln Lys Ser His Arg Leu His His Gln Tyr Thr Ser His Ile Asp Asn
    50                  55                  60 gac atg gga cat ccc tgg gtg gtc gaa aaa gat ttc atg aca cgt ggt      240
Asp Met Gly His Pro Trp Val Val Glu Lys Asp Phe Met Thr Arg Gly
65                  70                  75                  80 tgg ata att cgc aat ttt tca aag atc cca ctt tcc ggt ttt att cga      288
Trp Ile Ile Arg Asn Phe Ser Lys Ile Pro Leu Ser Gly Phe Ile Arg
                85                  90                  95 tgg agt ccg att tac aca ata gtt ggt cta cca gac ggc agc cac ttt      336
Trp Ser Pro Ile Tyr Thr Ile Val Gly Leu Pro Asp Gly Ser His Phe
            100                 105                 110 tgg cct tat agt aaa ctt ttc aat aac aat cgc gaa cga gtg aaa tgt      384
Trp Pro Tyr Ser Lys Leu Phe Asn Asn Asn Arg Glu Arg Val Lys Cys
        115                 120                 125
```

```
gtt gtt agt ggt ttg gca tgt gta ttt tgt gct gtg gtg gcc ttt gtt       432
Val Val Ser Gly Leu Ala Cys Val Phe Cys Ala Val Val Ala Phe Val
    130                 135                 140 tta tgt agt tgt agt tgg tat aca ttc atc aaa tat tat tac gtt tcg       480
Leu Cys Ser Cys Ser Trp Tyr Thr Phe Ile Lys Tyr Tyr Tyr Val Ser
145                 150                 155                 160 tta ttg ttt caa ggc tat tgg ctt gtt atc ata act tat cta caa cac       528
Leu Leu Phe Gln Gly Tyr Trp Leu Val Ile Ile Thr Tyr Leu Gln His
                165                 170                 175 aac gat tac agc ata gag gtt tac gag gaa gat tac tgg agt tat gta       576
Asn Asp Tyr Ser Ile Glu Val Tyr Glu Glu Asp Tyr Trp Ser Tyr Val
            180                 185                 190 atg ggg caa gta caa acc att gat cga gtt tat ggt ttt ggt att gat       624
Met Gly Gln Val Gln Thr Ile Asp Arg Val Tyr Gly Phe Gly Ile Asp
        195                 200                 205 aca cta cta cat cat att act gat gga cac gtg gcc cat cat ttc ttc       672
Thr Leu Leu His His Ile Thr Asp Gly His Val Ala His His Phe Phe
    210                 215                 220 ttt aca aaa att cca cat tac cat ttg atg gaa gca aca gcg gca att       720
Phe Thr Lys Ile Pro His Tyr His Leu Met Glu Ala Thr Ala Ala Ile
225                 230                 235                 240 aga aat gtt ttg gaa cct tat aag gca tat cga tgt aaa agc aat tcc       768
Arg Asn Val Leu Glu Pro Tyr Lys Ala Tyr Arg Cys Lys Ser Asn Ser
                245                 250                 255 aat ttt tta ttg gat tat ttg acg ctc aat gta aag tta gaa tat ctt       816
Asn Phe Leu Leu Asp Tyr Leu Thr Leu Asn Val Lys Leu Glu Tyr Leu
            260                 265                 270 att ggt aaa ggc act ggg atc ctt act tat gct aga caa caa aaa gag       864
Ile Gly Lys Gly Thr Gly Ile Leu Thr Tyr Ala Arg Gln Gln Lys Glu
        275                 280                 285 gaa tgatgatttg tcaagttttt tttttttttt tgtaatgttt ttaaatcagt            917
Glu tttgaaaaaa tgagtttgaa actttcatca cttcagtgtt ttacaatgtc aacgattggt     977
ggcatttgta ataagggttt gcttttactg ttatgagttc tggtgtatta gtaataaaag    1037
tttttattcg actaaaaaaa aaaaaaaaaa a                                   1068

<210> SEQ ID NO 6
<211> LENGTH: 1221
<212> TYPE: DNA
<213> ORGANISM: Strongyloides stercoralis
<220> FEATURE:
<221> NAME/KEY: CDS
<222> LOCATION: (28)...(1131)

<400> SEQUENCE: 6
attttattac gtgattatat aatagtt atg tcg tct acc act caa aca aaa acc     54
                               Met Ser Ser Thr Thr Gln Thr Lys Thr
                                 1               5 ctt tta aaa gaa aat aaa caa aaa aaa gaa ttt cca aca ctt gaa gaa       102
Leu Leu Lys Glu Asn Lys Gln Lys Lys Glu Phe Pro Thr Leu Glu Glu
 10                  15                  20                  25 ata aaa aag gct ata cca gct gaa tgt tgg gaa aaa aat gca tta aag       150
Ile Lys Lys Ala Ile Pro Ala Glu Cys Trp Glu Lys Asn Ala Leu Lys
                 30                  35                  40 tct att tct tat ctt gtt ttg gac tat gct ctt ata gct ggt atg tat       198
Ser Ile Ser Tyr Leu Val Leu Asp Tyr Ala Leu Ile Ala Gly Met Tyr
             45                  50                  55 ttt gct tta cca ctt tct gaa ggt tat ggt ggt ttt ctt ggt tta tgt       246
Phe Ala Leu Pro Leu Ser Glu Gly Tyr Gly Gly Phe Leu Gly Leu Cys
         60                  65                  70
```

```
gtt tgg tat tgg tta ata ggt atg ttt gga tca tca ctt ttt att gtt      294
Val Trp Tyr Trp Leu Ile Gly Met Phe Gly Ser Ser Leu Phe Ile Val
     75                  80                  85 gga cat gat tgt ggg cat aca aac ttt tca aac tat aca tgg tta aat      342
Gly His Asp Cys Gly His Thr Asn Phe Ser Asn Tyr Thr Trp Leu Asn
 90                  95                 100                 105 gat ctt tgt ggt cat att gct cat gcc cca att tta gca cca tac tgg      390
Asp Leu Cys Gly His Ile Ala His Ala Pro Ile Leu Ala Pro Tyr Trp
                    110                 115                 120 cca tgg caa aag tct cat aga caa cat cat caa tat aca tca cat tta      438
Pro Trp Gln Lys Ser His Arg Gln His His Gln Tyr Thr Ser His Leu
                125                 130                 135 gaa aaa gat aaa gga cat cct tgg acg act gaa gaa gac tgg gtt act      486
Glu Lys Asp Lys Gly His Pro Trp Thr Thr Glu Glu Asp Trp Val Thr
            140                 145                 150 aaa aat ttc gtg ttt aaa cat ttt gca aaa ctt cca att tct ggt tta      534
Lys Asn Phe Val Phe Lys His Phe Ala Lys Leu Pro Ile Ser Gly Leu
        155                 160                 165 ttt aga tgg aat cca att tat act ggt ctt ggt tta ccc gat gga tca      582
Phe Arg Trp Asn Pro Ile Tyr Thr Gly Leu Gly Leu Pro Asp Gly Ser
170                 175                 180                 185 cat ttt tgg cct tat tca aaa ctt ttt aca aca aca aca gaa cgt att      630
His Phe Trp Pro Tyr Ser Lys Leu Phe Thr Thr Thr Thr Glu Arg Ile
                    190                 195                 200 caa tgt gtt att tct gga tta gca tgt ctt ttc tgt gct gga att gct      678
Gln Cys Val Ile Ser Gly Leu Ala Cys Leu Phe Cys Ala Gly Ile Ala
                205                 210                 215 ctt cac ctt aat gat tat tca att tat aac ttt ata aaa tat tat tat      726
Leu His Leu Asn Asp Tyr Ser Ile Tyr Asn Phe Ile Lys Tyr Tyr Tyr
            220                 225                 230 att cca tgt atg ttc caa gga ttt tgg tta gtt att att aca tat ctt      774
Ile Pro Cys Met Phe Gln Gly Phe Trp Leu Val Ile Ile Thr Tyr Leu
        235                 240                 245 caa cat caa tca gaa aca att gaa gtt tat gaa gaa gga agc tgg aat      822
Gln His Gln Ser Glu Thr Ile Glu Val Tyr Glu Glu Gly Ser Trp Asn
250                 255                 260                 265 tat gtt aga gga caa ctt caa aca att gat aga act tat gga ttt ggt      870
Tyr Val Arg Gly Gln Leu Gln Thr Ile Asp Arg Thr Tyr Gly Phe Gly
                    270                 275                 280 att gat aca att ctt cat cat ata tct gat ggt cat gtt gct cat cat      918
Ile Asp Thr Ile Leu His His Ile Ser Asp Gly His Val Ala His His
                285                 290                 295 ttc ttc ttt aca aga att cct cat tat cat ttg atg aaa gct acc aaa      966
Phe Phe Phe Thr Arg Ile Pro His Tyr His Leu Met Lys Ala Thr Lys
            300                 305                 310 gca att caa aat gtt ctt aaa gat tat cca gga gca tat aaa aga aag     1014
Ala Ile Gln Asn Val Leu Lys Asp Tyr Pro Gly Ala Tyr Lys Arg Lys
        315                 320                 325 aca aat tat gat ttt gtt ttt gaa tat ctt aaa tta aac att att ctt     1062
Thr Asn Tyr Asp Phe Val Phe Glu Tyr Leu Lys Leu Asn Ile Ile Leu
330                 335                 340                 345 gaa tat ctt act ggt aaa ggt tca gga gtt ctc caa tat cca aat gca     1110
Glu Tyr Leu Thr Gly Lys Gly Ser Gly Val Leu Gln Tyr Pro Asn Ala
                    350                 355                 360 aaa aag gct aat aaa gca tat taaaagggtt aattaatata aatataaaaa        1161
Lys Lys Ala Asn Lys Ala Tyr
                365 aaacagtata tactgattct ttcaaataaa ggcaatagtt ataaaaaaaa aaaaaaaaa    1221
```

```
<210> SEQ ID NO 7
<211> LENGTH: 1232
<212> TYPE: DNA
<213> ORGANISM: Rhabditella axei
<220> FEATURE:
<221> NAME/KEY: CDS
<222> LOCATION: (25)...(1146)

<400> SEQUENCE: 7
```

| | | | | | | | | | | | | | | |
|---|---|---|---|---|---|---|---|---|---|---|---|---|---|---| gtttaattac ccaagtttga gggt atg acg gtt gct act cag ctt aac gcc      51
                          Met Thr Val Ala Thr Gln Leu Asn Ala
                          1               5 aag aag gcg aat ttg gag aaa gca gat gta ccg aac ctc ccc tca gtg     99
Lys Lys Ala Asn Leu Glu Lys Ala Asp Val Pro Asn Leu Pro Ser Val
 10              15                  20                  25 ggt gac atc aga aag gct att ccc cca gag tgt ttt aag aag gat gcc    147
Gly Asp Ile Arg Lys Ala Ile Pro Pro Glu Cys Phe Lys Lys Asp Ala
             30                  35                  40 ata aaa tct att cga tat tta att cag gat att ctc att cta gtc ggt    195
Ile Lys Ser Ile Arg Tyr Leu Ile Gln Asp Ile Leu Ile Leu Val Gly
             45                  50                  55 ttc tat att gct ctt cct tac gtc gaa ctc tat ctc ggc tgg atc ggt    243
Phe Tyr Ile Ala Leu Pro Tyr Val Glu Leu Tyr Leu Gly Trp Ile Gly
             60                  65                  70 ctg ttt gct tgg tat tgg gcc att gga att gcc ggc tgt tct ctg ttc    291
Leu Phe Ala Trp Tyr Trp Ala Ile Gly Ile Ala Gly Cys Ser Leu Phe
 75                  80                  85 atc atc ggt cat gac tgc gga cac ggc tct ttc tcc gac tac gtg tgg    339
Ile Ile Gly His Asp Cys Gly His Gly Ser Phe Ser Asp Tyr Val Trp
 90                  95                 100                 105 ttg aat gac ctg tgt gga cac att gct cat gct ccc atc ctc gct cct    387
Leu Asn Asp Leu Cys Gly His Ile Ala His Ala Pro Ile Leu Ala Pro
                110                 115                 120 tac tgg cca tgg cag aag agt cac aga caa cat cat cag tac act tct    435
Tyr Trp Pro Trp Gln Lys Ser His Arg Gln His His Gln Tyr Thr Ser
             125                 130                 135 cat ctg gaa aag gac aag ggt cat cca tgg gtc act caa aaa gac ttt    483
His Leu Glu Lys Asp Lys Gly His Pro Trp Val Thr Gln Lys Asp Phe
             140                 145                 150 gag gac aga act act atc gag aga tat ttc tcc atg att cct ttg tct    531
Glu Asp Arg Thr Thr Ile Glu Arg Tyr Phe Ser Met Ile Pro Leu Ser
 155                 160                 165 gga tgg ctg aga tgg aac ccc atc tac aca gtc gtt ggt ctt tcc gat    579
Gly Trp Leu Arg Trp Asn Pro Ile Tyr Thr Val Val Gly Leu Ser Asp
170                 175                 180                 185 gga agt cac ttt tgg cca tgg tct cgt ctg ttc aca acg act gaa gat    627
Gly Ser His Phe Trp Pro Trp Ser Arg Leu Phe Thr Thr Thr Glu Asp
                190                 195                 200 aga gta aaa tgt gcc atc agc gga ttg gct tgt ctt ttc tgt ggt tca    675
Arg Val Lys Cys Ala Ile Ser Gly Leu Ala Cys Leu Phe Cys Gly Ser
             205                 210                 215 gtt gcc ttc tat ctg gct gac tat tct gtc tac aac tgg gtc aaa tat    723
Val Ala Phe Tyr Leu Ala Asp Tyr Ser Val Tyr Asn Trp Val Lys Tyr
             220                 225                 230 tac ttc att cct ctt ctc ttc caa ggt ctt ttc ttg gtt atc atc acc    771
Tyr Phe Ile Pro Leu Leu Phe Gln Gly Leu Phe Leu Val Ile Ile Thr
 235                 240                 245 tat ctg caa cat cag aat gaa gac att gag gta tac gag aac gac gaa    819
Tyr Leu Gln His Gln Asn Glu Asp Ile Glu Val Tyr Glu Asn Asp Glu
250                 255                 260                 265

```
tgg tct ttc gta aga gga caa act caa acc atc gac aga ttc tgg ggt     867
Trp Ser Phe Val Arg Gly Gln Thr Gln Thr Ile Asp Arg Phe Trp Gly
        270                 275                 280 ttc gga ctt gac aca atc atg cac cac ata act gac ggt cat gtc gcc     915
Phe Gly Leu Asp Thr Ile Met His His Ile Thr Asp Gly His Val Ala
285                 290                 295 cat cac ttc ttc ttc aca gcc att cct cac tac aac ctc cta aaa gcc     963
His His Phe Phe Phe Thr Ala Ile Pro His Tyr Asn Leu Leu Lys Ala
            300                 305                 310 aca gaa ccg ata aag aag gtt ctg gaa cct ctg aaa gac act cca tac    1011
Thr Glu Pro Ile Lys Lys Val Leu Glu Pro Leu Lys Asp Thr Pro Tyr
        315                 320                 325 ggc tac aag agc aaa gtc aac tac gac ttt ttg ttc gaa tac ttc aaa    1059
Gly Tyr Lys Ser Lys Val Asn Tyr Asp Phe Leu Phe Glu Tyr Phe Lys
330                 335                 340                 345 tcc aac ttc ctt ttt gat tat ttg gtt cct aag agc aaa gga gtt ctt    1107
Ser Asn Phe Leu Phe Asp Tyr Leu Val Pro Lys Ser Lys Gly Val Leu
            350                 355                 360 caa tat cgt gtc ggt gtt gag aag tct cga aag atc caa taatcacatt    1156
Gln Tyr Arg Val Gly Val Glu Lys Ser Arg Lys Ile Gln
        365                 370 aaaactcctt ctggcgggta cctttctttc tcacttacca ataaatgttg gttagttaaa    1216
aaaaaaaaaa aaaaa                                                     1232

<210> SEQ ID NO 8
<211> LENGTH: 397
<212> TYPE: PRT
<213> ORGANISM: Meloidogyne incognita

<400> SEQUENCE: 8

Met Ser Tyr Leu Asp Thr Thr Lys Asn Asn Leu Asn Asn Gly Gly Ser
 1               5                  10                  15

Asn Asp Asn Gly Asn Ala Phe Cys Asn Asp Asn Asp Phe Val Gly Asn
            20                  25                  30

Asn Ala Glu Ser Val Val Ser Asn Val Ala Ala Pro Asn Val Glu Glu
        35                  40                  45

Leu Arg Met Ser Val Pro Pro Glu Cys Phe Glu Lys Pro Leu Ile Arg
    50                  55                  60

Ser Ile Ser Tyr Leu Ile Leu Asp Leu Val Ile Ser Gly Leu Tyr
65                  70                  75                  80

Met Val Val Gly Ile Val Glu Asn Tyr Leu Gly Phe Val Gly Leu Leu
                85                  90                  95

Ile Trp Tyr Trp Val Leu Gly Met Tyr Leu Ser Ser Leu Phe Cys Ile
            100                 105                 110

Gly His Asp Cys Gly His Gly Thr Phe Ser Ser Tyr Thr Trp Val Asn
        115                 120                 125

Asp Leu Phe Gly His Ile Ser His Ala Val Ile Met Val Pro Phe Trp
    130                 135                 140

Pro Trp Gln Lys Ser His Arg Gln His Gln Tyr Thr Ala His Leu
145                 150                 155                 160

Asp Lys Asp Lys Gly His Pro Val Thr Glu Glu Tyr Glu Ser
                165                 170                 175

Ser Asn Trp Ile Lys Lys His Phe Ala Lys Ile Pro Leu Ser Gly Leu
            180                 185                 190

Ile Arg Trp Asn Pro Ile Tyr Thr Ile Ala Gly Leu Pro Asp Gly Ser
        195                 200                 205
```

```
His Phe Trp Pro Trp Ser Lys Leu Phe Glu Asn Asn Val Asp Arg Ile
    210                 215                 220
Lys Cys Val Val Ser Val Ser Ala Cys Phe Leu Cys Ser Phe Val Ile
225                 230                 235                 240
Leu Tyr Tyr Met Asn Tyr Asn Leu Trp Asn Phe Phe Lys Tyr Tyr Tyr
                245                 250                 255
Val Pro Leu Met Phe Gln Gly Phe Trp Met Val Ile Ile Thr Phe Leu
            260                 265                 270
Gln His Gln Asp Glu Gln Ile Glu Val Tyr Glu Glu Gly Thr Trp Ala
        275                 280                 285
Phe Met Lys Gly Gln Leu Gln Thr Val Asp Arg Ser Phe Gly Phe Gly
    290                 295                 300
Ile Asp Lys Ala Leu His His Ile Thr Asp Gly His Val Ala His His
305                 310                 315                 320
Phe Phe Phe Thr Arg Ile Pro His Tyr Asn Leu Pro Lys Ala Thr Glu
                325                 330                 335
Ala Val Lys Lys Val Leu Gln Lys Tyr Pro Gly Ala Tyr Lys His Lys
            340                 345                 350
Ser Ala Tyr Asp Phe Leu Ile Lys Phe Leu Trp Leu Asn Ile Lys Leu
        355                 360                 365
Asp Cys Leu Val Gly Lys Gly Ser Gly Leu Leu Lys Tyr Arg Ser Thr
    370                 375                 380
Val Gln Asn Asp Glu Gln Leu Asn Asn Lys Lys Asp Lys
385                 390                 395

<210> SEQ ID NO 9
<211> LENGTH: 413
<212> TYPE: PRT
<213> ORGANISM: Meloidogyne incognita

<400> SEQUENCE: 9

Met Ser Tyr Ile Asp Thr Thr Lys Asn Asn Leu Ile Asn Asn Gly Gly
1               5                   10                  15
Tyr Asn Pro Gly Asn Ile Asn Asp Asp Gly Ser Ser Ser Tyr Arg Leu
            20                  25                  30
Phe Asn Asp Asp Ser Lys Ser Glu Phe Tyr Gly Gly Asn Ala Glu Ser
        35                  40                  45
Ala Ser Ser Asn Ile Gly Val Phe Arg Gln Val Pro Asn Val Glu Glu
    50                  55                  60
Leu Arg Met Ser Val Pro Pro Glu Cys Phe Asp Lys Pro Leu Ile Arg
65                  70                  75                  80
Ser Ile Ser Tyr Leu Ile Leu Asp Leu Val Ile Ile Ser Gly Leu Tyr
                85                  90                  95
Met Val Val Gly Ile Val Glu Asn Tyr Leu Gly Phe Val Gly Leu Leu
            100                 105                 110
Ile Trp Tyr Trp Val Leu Gly Met Tyr Leu Ser Ser Leu Phe Cys Ile
        115                 120                 125
Gly His Asp Cys Gly His Gly Thr Phe Ser Ser Tyr Thr Trp Val Asn
    130                 135                 140
Asp Leu Phe Gly His Ile Ser His Ala Val Ile Met Val Pro Phe Trp
145                 150                 155                 160
Pro Trp Gln Lys Ser His Arg Gln His His Gln Tyr Thr Ala His Leu
                165                 170                 175
Asp Lys Asp Lys Gly His Pro Trp Val Thr Glu Glu Tyr Glu Ser
            180                 185                 190
```

Ser Asn Trp Ile Lys Lys His Phe Ala Lys Ile Pro Leu Ser Gly Leu
            195                 200                 205

Ile Arg Trp Asn Pro Ile Tyr Thr Ile Ala Gly Leu Pro Asp Gly Ser
210                 215                 220

His Phe Trp Pro Trp Ser Lys Leu Phe Glu Asn Asn Val Asp Arg Ile
225                 230                 235                 240

Lys Cys Val Val Ser Val Ser Ala Cys Phe Leu Cys Ser Phe Val Ile
            245                 250                 255

Leu Tyr Tyr Met Asn Tyr Asn Leu Trp Asn Phe Phe Lys Tyr Tyr Tyr
            260                 265                 270

Val Pro Leu Met Phe Gln Gly Phe Trp Met Val Ile Thr Phe Leu
            275                 280                 285

Gln His Gln Asp Glu Gln Ile Glu Val Tyr Glu Glu Gly Thr Trp Ala
            290                 295                 300

Phe Met Lys Gly Gln Leu Gln Thr Val Asp Arg Ser Phe Gly Phe Gly
305                 310                 315                 320

Ile Asp Lys Ala Leu His His Ile Thr Asp Gly His Val Ala His His
            325                 330                 335

Phe Phe Phe Thr Arg Ile Pro His Tyr Asn Leu Pro Lys Ala Thr Glu
            340                 345                 350

Ala Val Lys Lys Val Leu Gln Lys Tyr Pro Gly Ala Tyr Lys His Lys
            355                 360                 365

Ser Ala Tyr Asp Phe Leu Ile Lys Phe Leu Trp Leu Asn Ile Lys Leu
            370                 375                 380

Asp Cys Leu Val Gly Lys Gly Ser Gly Leu Leu Lys Tyr Arg Ser Thr
385                 390                 395                 400

Val Gln Asn Asp Glu Gln Leu Asn Asn Lys Lys Asp Lys
                    405                 410

<210> SEQ ID NO 10
<211> LENGTH: 387
<212> TYPE: PRT
<213> ORGANISM: Meloidogyne incognita

<400> SEQUENCE: 10

Met Ser Leu Ile Ser Ser Asn Thr Ile Val Glu Thr Thr Lys Thr Asn
1               5                   10                  15

Gly Asn Thr Ile Ser Asp Ser Asn Asn Lys Ile Asn Tyr Ser Phe Pro
            20                  25                  30

Asn Leu Asn Glu Leu Arg Asn Ala Ile Pro Ala Glu Cys Phe Glu Lys
        35                  40                  45

Ser Leu Ile Arg Ser Leu Ser Tyr Leu Ile Leu Asp Phe Leu Ile Ile
    50                  55                  60

Tyr Gly Leu Tyr Leu Val Val Gly Val Val Glu Asp Asn Phe Gly Ile
65                  70                  75                  80

Ile Gly Leu Leu Leu Trp Tyr Trp Val Leu Gly Met Phe Leu Phe Ser
                85                  90                  95

Ile Phe Ala Val Gly His Asp Cys Gly His Gly Thr Phe Ser Ser Tyr
            100                 105                 110

Thr Trp Val Asn Asp Leu Phe Gly His Val Ala His Ala Pro Thr Met
        115                 120                 125

Val Pro Tyr Trp Pro Trp Gln Lys Ser His Arg Leu His His Gln Tyr
    130                 135                 140

Thr Ala His Leu Asp Lys Asp Met Ser His Pro Trp Ile Pro Glu Lys

```
                145                 150                 155                 160
Leu Tyr Leu Ser Leu Asn Trp Ile Ser Lys His Tyr Leu Lys Phe Pro
                165                 170                 175

Leu Thr Gly Phe Val Ser Trp Ile Pro Leu Tyr Thr Ile Phe Gly Ile
                180                 185                 190

Pro Asp Gly Ser His Phe Trp Pro Trp Ser Lys Leu Phe Glu Asn Asn
                195                 200                 205

Thr Asp Arg Ile Lys Cys Ala Val Ser Val Ala Ala Cys Phe Leu Cys
        210                 215                 220

Ala Tyr Ile Ala Leu Tyr Cys Ser Asn Tyr Asn Leu Trp Ile Phe Phe
225                 230                 235                 240

Lys Tyr Tyr Tyr Ile Pro Val Met Phe Gln Gly Phe Trp Leu Val Leu
                245                 250                 255

Ile Thr Tyr Leu Gln His His Asp Glu Thr Glu Val Tyr Glu Asp
                260                 265                 270

Gly Thr Trp Gly Phe Val Arg Gly Gln Leu Gln Thr Val Asp Arg Ser
                275                 280                 285

Phe Gly Phe Gly Ile Asp Lys Ala Leu His Asn Ile Thr Asp Gly His
        290                 295                 300

Val Ala His His Leu Phe Phe Thr Arg Ile Pro His Tyr Asn Leu Pro
305                 310                 315                 320

Lys Ala Thr Glu Ala Val Lys Arg Ile Leu Thr Glu Lys Tyr Pro Gly
                325                 330                 335

Thr Tyr Lys Tyr Lys Lys Ser Tyr Asp Phe Leu Ile Glu Phe Leu Trp
                340                 345                 350

Leu Asn Ile Lys Leu Asp Tyr Leu Val Gly Lys Gly Ser Gly Leu Leu
                355                 360                 365

Arg Tyr Arg Asn Asn Ile Arg Thr Asn Asp Gln Ser Lys Thr Thr Lys
                370                 375                 380

Lys Asn Asn
385

<210> SEQ ID NO 11
<211> LENGTH: 389
<212> TYPE: PRT
<213> ORGANISM: Heterodera glycines

<400> SEQUENCE: 11

Met Ser Pro Pro Cys Ser Phe Ser Pro Ser Ala Ser Ser Ser Pro
1                   5                   10                  15

Asp Ser Pro Ser Ala Glu Gly Gln Ala Gln Gln Asn Gly Gln Val Leu
                20                  25                  30

Ala Pro Arg Pro Leu Pro Thr Trp Glu Glu Ile Arg Ala Ala Val Pro
            35                  40                  45

Lys Glu Cys Phe Glu Lys Ser Leu Leu Arg Ser Leu Tyr Tyr Leu Ala
        50                  55                  60

Ile Asp Leu Leu Val Ile Gly Phe Leu Tyr Ala Val Val Pro Phe Val
65                  70                  75                  80

Glu Thr Asn Phe Gly Leu Ile Gly Leu Phe Phe Trp Tyr Cys Leu Leu
                85                  90                  95

Gly Met Phe Leu Ser Ser Leu Phe Cys Val Gly His Asp Cys Gly His
                100                 105                 110

Gly Thr Phe Ser Asp Trp Thr Trp Val Asn Asp Ile Phe Gly His Ile
                115                 120                 125
```

```
Ser His Ala Leu Leu Met Val Pro Phe Trp Pro Trp Gln Lys Ser His
130                 135                 140

Arg Gln His His Gln Phe Thr Ser His Val Asp Lys Asp Lys Gly His
145                 150                 155                 160

Pro Trp Val Leu Glu Asp Asp Tyr Glu Gly Gly Gly Trp Leu Arg Lys
                165                 170                 175

His Phe Ala Lys Ile Pro Leu Ser Gly Leu Ile Arg Trp Asn Pro Ile
            180                 185                 190

Tyr Thr Val Ala Gly Leu Pro Asp Gly Ser His Phe Trp Pro Phe Ser
        195                 200                 205

Arg Leu Phe Ser Asn Asn Thr Glu Arg Phe Lys Cys Leu Ile Ser Ser
    210                 215                 220

Ser Leu Cys Leu Ile Thr Ser Trp Ala Ile Phe Val Leu Leu Asp His
225                 230                 235                 240

Ser Pro Trp Ala Phe Leu Lys Tyr Tyr Val Pro Leu Met Phe Gln
                245                 250                 255

Gly Tyr Trp Met Val Ile Ile Thr Tyr Leu Gln His Gln Asp Glu Gln
                260                 265                 270

Ile Glu Val Tyr Glu Glu Gly Asn Trp Ala Phe Val Lys Gly Gln Leu
            275                 280                 285

Gln Thr Tyr Asp Arg Glu Tyr Gly Phe Gly Ile Asp His Ala Met His
        290                 295                 300

His Ile Thr Asp Gly His Val Ala His His Phe Phe Thr Arg Ile
305                 310                 315                 320

Pro His Tyr His Leu Pro Glu Ala Thr Lys Ser Ile Arg Lys Ile Met
                325                 330                 335

Glu Lys Tyr Pro Gly Ala Tyr Lys Arg Lys Ser Asn Tyr Asp Phe Leu
                340                 345                 350

Leu Gln Phe Leu Trp Met Asn Val Lys Leu Asp Cys Leu Val Gly Lys
            355                 360                 365

Gly Ser Gly Leu Leu Lys Tyr Arg Thr Thr Ala Arg Arg Glu Glu Arg
    370                 375                 380

Gln Gln Lys Glu Asp
385

<210> SEQ ID NO 12
<211> LENGTH: 289
<212> TYPE: PRT
<213> ORGANISM: Dirofilaria immitis

<400> SEQUENCE: 12

Tyr Cys Cys Met Gly Met Phe Gly Ser Ser Leu Phe Val Val Gly His
1               5                   10                  15

Asp Cys Gly His Gly Thr Phe Ser Glu Tyr Thr Trp Val Asn Asp Phe
            20                  25                  30

Phe Gly His Ile Ala His Ala Ser Leu Leu Val Pro Tyr Trp Pro Trp
        35                  40                  45

Gln Lys Ser His Arg Leu His His Gln Tyr Thr Ser His Ile Asp Asn
    50                  55                  60

Asp Met Gly His Pro Trp Val Glu Lys Asp Phe Met Thr Arg Gly
65                  70                  75                  80

Trp Ile Ile Arg Asn Phe Ser Lys Ile Pro Leu Ser Gly Phe Ile Arg
                85                  90                  95

Trp Ser Pro Ile Tyr Thr Ile Val Gly Leu Pro Asp Gly Ser His Phe
            100                 105                 110
```

-continued

Trp Pro Tyr Ser Lys Leu Phe Asn Asn Asn Arg Glu Arg Val Lys Cys
            115                 120                 125

Val Val Ser Gly Leu Ala Cys Val Phe Cys Ala Val Val Ala Phe Val
        130                 135                 140

Leu Cys Ser Cys Ser Trp Tyr Thr Phe Ile Lys Tyr Tyr Val Ser
145                 150                 155                 160

Leu Leu Phe Gln Gly Tyr Trp Leu Val Ile Ile Thr Tyr Leu Gln His
                165                 170                 175

Asn Asp Tyr Ser Ile Glu Val Tyr Glu Glu Asp Tyr Trp Ser Tyr Val
            180                 185                 190

Met Gly Gln Val Gln Thr Ile Asp Arg Val Tyr Gly Phe Gly Ile Asp
        195                 200                 205

Thr Leu Leu His His Ile Thr Asp Gly His Val Ala His His Phe Phe
        210                 215                 220

Phe Thr Lys Ile Pro His Tyr His Leu Met Glu Ala Thr Ala Ala Ile
225                 230                 235                 240

Arg Asn Val Leu Glu Pro Tyr Lys Ala Tyr Arg Cys Lys Ser Asn Ser
                245                 250                 255

Asn Phe Leu Leu Asp Tyr Leu Thr Leu Asn Val Lys Leu Glu Tyr Leu
            260                 265                 270

Ile Gly Lys Gly Thr Gly Ile Leu Thr Tyr Ala Arg Gln Gln Lys Glu
        275                 280                 285

Glu

<210> SEQ ID NO 13
<211> LENGTH: 368
<212> TYPE: PRT
<213> ORGANISM: Strongyloides stercoralis

<400> SEQUENCE: 13

Met Ser Ser Thr Thr Gln Thr Lys Thr Leu Leu Lys Glu Asn Lys Gln
1               5                   10                  15

Lys Lys Glu Phe Pro Thr Leu Glu Glu Ile Lys Lys Ala Ile Pro Ala
            20                  25                  30

Glu Cys Trp Glu Lys Asn Ala Leu Lys Ser Ile Ser Tyr Leu Val Leu
        35                  40                  45

Asp Tyr Ala Leu Ile Ala Gly Met Tyr Phe Ala Leu Pro Leu Ser Glu
    50                  55                  60

Gly Tyr Gly Gly Phe Leu Gly Leu Cys Val Trp Tyr Trp Leu Ile Gly
65                  70                  75                  80

Met Phe Gly Ser Ser Leu Phe Ile Val Gly His Asp Cys Gly His Thr
                85                  90                  95

Asn Phe Ser Asn Tyr Thr Trp Leu Asn Asp Leu Cys Gly His Ile Ala
            100                 105                 110

His Ala Pro Ile Leu Ala Pro Tyr Trp Pro Trp Gln Lys Ser His Arg
        115                 120                 125

Gln His His Gln Tyr Thr Ser His Leu Glu Lys Asp Lys Gly His Pro
    130                 135                 140

Trp Thr Thr Glu Glu Asp Trp Val Thr Lys Asn Phe Val Phe Lys His
145                 150                 155                 160

Phe Ala Lys Leu Pro Ile Ser Gly Leu Phe Arg Trp Asn Pro Ile Tyr
                165                 170                 175

Thr Gly Leu Gly Leu Pro Asp Gly Ser His Phe Trp Pro Tyr Ser Lys
            180                 185                 190

-continued

```
Leu Phe Thr Thr Thr Glu Arg Ile Gln Cys Val Ile Ser Gly Leu
        195                 200                 205

Ala Cys Leu Phe Cys Ala Gly Ile Ala Leu His Leu Asn Asp Tyr Ser
210                 215                 220

Ile Tyr Asn Phe Ile Lys Tyr Tyr Ile Pro Cys Met Phe Gln Gly
225                 230                 235                 240

Phe Trp Leu Val Ile Ile Thr Tyr Leu Gln His Gln Ser Glu Thr Ile
                    245                 250                 255

Glu Val Tyr Glu Glu Gly Ser Trp Asn Tyr Val Arg Gly Gln Leu Gln
                260                 265                 270

Thr Ile Asp Arg Thr Tyr Gly Phe Gly Ile Asp Thr Ile Leu His His
            275                 280                 285

Ile Ser Asp Gly His Val Ala His His Phe Phe Thr Arg Ile Pro
        290                 295                 300

His Tyr His Leu Met Lys Ala Thr Lys Ala Ile Gln Asn Val Leu Lys
305                 310                 315                 320

Asp Tyr Pro Gly Ala Tyr Lys Arg Lys Thr Asn Tyr Asp Phe Val Phe
                325                 330                 335

Glu Tyr Leu Lys Leu Asn Ile Ile Leu Glu Tyr Leu Thr Gly Lys Gly
                340                 345                 350

Ser Gly Val Leu Gln Tyr Pro Asn Ala Lys Lys Ala Asn Lys Ala Tyr
                355                 360                 365

<210> SEQ ID NO 14
<211> LENGTH: 374
<212> TYPE: PRT
<213> ORGANISM: Rhabditella axei

<400> SEQUENCE: 14

Met Thr Val Ala Thr Gln Leu Asn Ala Lys Lys Ala Asn Leu Glu Lys
1               5                   10                  15

Ala Asp Val Pro Asn Leu Pro Ser Val Gly Asp Ile Arg Lys Ala Ile
                20                  25                  30

Pro Pro Glu Cys Phe Lys Lys Asp Ala Ile Lys Ser Ile Arg Tyr Leu
            35                  40                  45

Ile Gln Asp Ile Leu Ile Leu Val Gly Phe Tyr Ile Ala Leu Pro Tyr
50                  55                  60

Val Glu Leu Tyr Leu Gly Trp Ile Gly Leu Phe Ala Trp Tyr Trp Ala
65                  70                  75                  80

Ile Gly Ile Ala Gly Cys Ser Leu Phe Ile Ile Gly His Asp Cys Gly
                85                  90                  95

His Gly Ser Phe Ser Asp Tyr Val Trp Leu Asn Asp Leu Cys Gly His
                100                 105                 110

Ile Ala His Ala Pro Ile Leu Ala Pro Tyr Trp Pro Trp Gln Lys Ser
            115                 120                 125

His Arg Gln His His Gln Tyr Thr Ser His Leu Glu Lys Asp Lys Gly
130                 135                 140

His Pro Trp Val Thr Gln Lys Asp Phe Glu Asp Arg Thr Thr Ile Glu
145                 150                 155                 160

Arg Tyr Phe Ser Met Ile Pro Leu Ser Gly Trp Leu Arg Trp Asn Pro
                165                 170                 175

Ile Tyr Thr Val Val Gly Leu Ser Asp Gly Ser His Phe Trp Pro Trp
                180                 185                 190

Ser Arg Leu Phe Thr Thr Thr Glu Asp Arg Val Lys Cys Ala Ile Ser
```

-continued

```
                195                 200                 205
Gly Leu Ala Cys Leu Phe Cys Gly Ser Val Ala Phe Tyr Leu Ala Asp
    210                 215                 220

Tyr Ser Val Tyr Asn Trp Val Lys Tyr Phe Ile Pro Leu Leu Phe
225                 230                 235                 240

Gln Gly Leu Phe Leu Val Ile Ile Thr Tyr Leu Gln His Gln Asn Glu
                245                 250                 255

Asp Ile Glu Val Tyr Glu Asn Asp Glu Trp Ser Phe Val Arg Gly Gln
                260                 265                 270

Thr Gln Thr Ile Asp Arg Phe Trp Gly Phe Gly Leu Asp Thr Ile Met
            275                 280                 285

His His Ile Thr Asp Gly His Val Ala His His Phe Phe Thr Ala
        290                 295                 300

Ile Pro His Tyr Asn Leu Leu Lys Ala Thr Glu Pro Ile Lys Lys Val
305                 310                 315                 320

Leu Glu Pro Leu Lys Asp Thr Pro Tyr Gly Tyr Lys Ser Lys Val Asn
                325                 330                 335

Tyr Asp Phe Leu Phe Glu Tyr Phe Lys Ser Asn Phe Leu Phe Asp Tyr
            340                 345                 350

Leu Val Pro Lys Ser Lys Gly Val Leu Gln Tyr Arg Val Gly Val Glu
            355                 360                 365

Lys Ser Arg Lys Ile Gln
    370
```

<210> SEQ ID NO 15
<211> LENGTH: 22
<212> TYPE: DNA
<213> ORGANISM: Artificial Sequence
<220> FEATURE:
<223> OTHER INFORMATION: primer

<400> SEQUENCE: 15
gtaatacgac tcactatagg gc                                              22

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
aattaaccct cactaaaggg                                                 20

<210> SEQ ID NO 17
<211> LENGTH: 22
<212> TYPE: DNA
<213> ORGANISM: Artificial Sequence
<220> FEATURE:
<223> OTHER INFORMATION: primer

<400> SEQUENCE: 17
gggtttaatt acccaagttt ga                                              22

<210> SEQ ID NO 18
<211> LENGTH: 50
<212> TYPE: DNA
<213> ORGANISM: Artificial Sequence
<220> FEATURE:
<223> OTHER INFORMATION: primer

```
<400> SEQUENCE: 18
gagagagaga gagagagaga actagtctcg agtttttttt tttttttttt          50

<210> SEQ ID NO 19
<211> LENGTH: 19
<212> TYPE: DNA
<213> ORGANISM: Artificial Sequence
<220> FEATURE:
<223> OTHER INFORMATION: primer

<400> SEQUENCE: 19
aagttccgtg cccacaatc                                            19

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
gccaaaaatg agaaccatcg                                           20

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
atgtcttatc ttgacacaac                                           20

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
ctatttatcc tttttattat                                           20

<210> SEQ ID NO 23
<211> LENGTH: 22
<212> TYPE: DNA
<213> ORGANISM: Artificial Sequence
<220> FEATURE:
<223> OTHER INFORMATION: primer

<400> SEQUENCE: 23
tctatattcg ctgttggaca cg                                        22

<210> SEQ ID NO 24
<211> LENGTH: 17
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)...(17)
<223> OTHER INFORMATION: n = A,T,C or G

<400> SEQUENCE: 24
gtrtadatng grttcca                                              17
```

```
<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
ctggtactgc ttgctcggca                                                    20

<210> SEQ ID NO 26
<211> LENGTH: 23
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)...(23)
<223> OTHER INFORMATION: n = A,T,C or G

<400> SEQUENCE: 26
aaraaraart grtgngcnac rtg                                                23

<210> SEQ ID NO 27
<211> LENGTH: 17
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)...(17)
<223> OTHER INFORMATION: n = A,T,C or G

<400> SEQUENCE: 27
atgggnatgt tyggntc                                                       17

<210> SEQ ID NO 28
<211> LENGTH: 19
<212> TYPE: DNA
<213> ORGANISM: Artificial Sequence
<220> FEATURE:
<223> OTHER INFORMATION: primer

<400> SEQUENCE: 28
gtacaaacca ttgatcgag                                                     19

<210> SEQ ID NO 29
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)...(24)
<223> OTHER INFORMATION: n = A,T,C or G

<400> SEQUENCE: 29
gayggntctc ayttytggcc ntgg                                               24

<210> SEQ ID NO 30
<211> LENGTH: 20
<212> TYPE: DNA
<213> ORGANISM: Artificial Sequence
<220> FEATURE:
```

-continued

<223> OTHER INFORMATION: primer

<400> SEQUENCE: 30
ctctatcttc agtcgttgtg                                                     20

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
ggttatcatc acctatctgc                                                     20

<210> SEQ ID NO 32
<211> LENGTH: 376
<212> TYPE: PRT
<213> ORGANISM: Caenorhabditis elegans

<400> SEQUENCE: 32

```
Met Thr Ile Ala Thr Lys Val Asn Thr Asn Lys Lys Asp Leu Asp Thr
  1               5                  10                  15

Ile Lys Val Pro Glu Leu Pro Ser Val Ala Val Lys Ala Ala Ile
             20                  25                  30

Pro Glu His Cys Phe Val Lys Asp Pro Leu Thr Ser Ile Ser Tyr Leu
         35                  40                  45

Ile Lys Asp Tyr Val Leu Leu Ala Gly Leu Tyr Phe Ala Val Pro Tyr
 50                  55                  60

Ile Glu His Tyr Leu Gly Trp Ile Gly Leu Leu Gly Trp Tyr Trp Ala
 65                  70                  75                  80

Met Gly Ile Val Gly Ser Ala Leu Phe Cys Val Gly His Asp Cys Gly
                 85                  90                  95

His Gly Ser Phe Ser Asp Tyr Glu Trp Leu Asn Asp Leu Cys Gly His
                100                 105                 110

Leu Ala His Ala Pro Ile Leu Ala Pro Phe Trp Pro Trp Gln Lys Ser
            115                 120                 125

His Arg Gln His His Gln Tyr Thr Ser His Val Glu Lys Asp Lys Gly
        130                 135                 140

His Pro Trp Val Thr Glu Glu Asp Tyr Asn Asn Arg Thr Ala Ile Glu
145                 150                 155                 160

Lys Tyr Phe Ala Val Ile Pro Ile Ser Gly Trp Leu Arg Trp Asn Pro
                165                 170                 175

Ile Tyr Thr Ile Val Gly Leu Pro Asp Gly Ser His Phe Trp Pro Trp
            180                 185                 190

Ser Arg Leu Phe Glu Thr Thr Glu Asp Arg Val Lys Cys Ala Val Ser
        195                 200                 205

Gly Val Ala Cys Ala Ile Cys Ala Tyr Ile Ala Phe Val Leu Cys Asp
    210                 215                 220

Tyr Ser Val Tyr Thr Phe Val Lys Tyr Tyr Ile Pro Leu Leu Phe
225                 230                 235                 240

Gln Gly Leu Ile Leu Val Ile Ile Thr Tyr Leu Gln His Gln Asn Glu
                245                 250                 255

Asp Ile Glu Val Tyr Glu Ala Asp Glu Trp Gly Phe Val Arg Gly Gln
            260                 265                 270

Thr Gln Thr Ile Asp Arg His Trp Gly Phe Gly Leu Asp Asn Ile Met
        275                 280                 285
```

-continued

```
His Asn Ile Thr Asn Gly His Val Ala His His Phe Phe Thr Lys
    290             295             300
Ile Pro His Tyr His Leu Leu Glu Ala Thr Pro Ala Ile Lys Lys Ala
305             310             315             320
Leu Glu Pro Leu Lys Asp Thr Gln Tyr Gly Tyr Lys Arg Glu Val Asn
            325             330             335
Tyr Asn Trp Phe Phe Lys Tyr Leu His Tyr Asn Val Thr Leu Asp Tyr
            340             345             350
Leu Thr His Lys Ala Lys Gly Val Leu Gln Tyr Arg Ser Gly Val Glu
        355             360             365
Ala Ala Lys Ala Lys Lys Ala Gln
    370             375
```